US008569505B2

(12) United States Patent
Codd et al.

(10) Patent No.: US 8,569,505 B2
(45) Date of Patent: Oct. 29, 2013

(54) AMINOTETRALIN-DERIVED UREA MODULATORS OF VANILLOID VR1 RECEPTOR

(75) Inventors: Ellen Codd, Blue Bell, PA (US); Scott L. Dax, Landenberg, PA (US); Michele Jetter, Norristown, PA (US); Mark McDonnell, Lansdale, PA (US); James J. McNally, Souderton, PA (US); Mark Youngman, Warminster, PA (US)

(73) Assignee: Janssen Pharmaceutica, NV (BE)

( * ) Notice: Subject to any disclaimer, the term of this patent is extended or adjusted under 35 U.S.C. 154(b) by 291 days.

(21) Appl. No.: 12/692,128

(22) Filed: Jan. 22, 2010

(65) Prior Publication Data

US 2010/0125140 A1 May 20, 2010

Related U.S. Application Data

(60) Continuation of application No. 11/877,220, filed on Oct. 23, 2007, now Pat. No. 7,678,812, which is a division of application No. 11/045,956, filed on Jan. 28, 2005, now abandoned, which is a division of application No. 10/438,477, filed on May 15, 2003, now Pat. No. 6,984,647.

(60) Provisional application No. 60/381,575, filed on May 17, 2002.

(51) Int. Cl.
C07D 217/02 (2006.01)
C07C 275/28 (2006.01)

(52) U.S. Cl.
USPC ........... 546/139; 546/143; 546/146; 546/159; 546/176; 564/26; 564/47; 564/48

(58) Field of Classification Search
None
See application file for complete search history.

(56) References Cited

U.S. PATENT DOCUMENTS

| 6,140,354 | A | 10/2000 | Dax et al. |
|---|---|---|---|
| 6,169,116 | B1 | 1/2001 | Swoboda |
| 6,201,025 | B1 | 3/2001 | Dax et al. |
| 6,984,647 | B2 | 1/2006 | Dax et al. |
| 7,678,812 | B2 * | 3/2010 | Codd et al. ............ 514/307 |
| 2003/0158188 | A1 | 8/2003 | Lee et al. |
| 2003/0158198 | A1 | 8/2003 | Lee et al. |
| 2003/0236280 | A1 | 12/2003 | Codd et al. |

FOREIGN PATENT DOCUMENTS

| EP | 0064964 B1 | 8/1984 |
|---|---|---|
| EP | 0335375 B1 | 10/1989 |
| TW | 171389 | 1/1990 |
| WO | WO 00/51970 | 9/2000 |
| WO | WO 02/08221 A2 | 1/2002 |
| WO | WO 02/16317 A1 | 2/2002 |
| WO | WO 02/16318 A1 | 2/2002 |
| WO | WO 02/16319 A1 | 2/2002 |
| WO | 02/33411 A1 | 4/2002 |
| WO | WO 03/014064 A1 | 2/2003 |
| WO | WO 03/049702 A2 | 6/2003 |
| WO | WO 03/059904 A1 | 7/2003 |
| WO | WO 03/062209 A2 | 7/2003 |
| WO | WO 03/068749 A1 | 8/2003 |

OTHER PUBLICATIONS

West, Anthony R., "Solid State Chemistry and its Applications", Wiley, New York, 1988, pp. 358 & 365.*
Agrawal, K.C., et al., "Potential Antitumor Agents. A Series of 5-Substituted 1-Formylisoquinoline Thiosemicarbazones," *J. Med Chem.*, 1968, pp. 700-703, vol. 11.
Bamberger, E. et al. "Ueber beta-tetrahydrophtylamin" *Chem Ber.*, 1988, pp. 847-860, vol. 21, XP009016746.
Garcia-Martinez, C. et al., "Attenuation of Thermal Nociception and Hyperalgesia by VRI Blockers," *PNAS*, 2002, pp. 2374-2379, vol. 99, No. 4.
Grant, E.R., "Simultaneous Intracellular Calcium and Sodium Flux Imaging in Human Vanilloid Receptor 1 (VR1)-Transfected Human Embryonic Kidney Cells: A Method to Resolve Ionic Dependence of VR1-Mediated Cell Death," *J. Pharm. Research Inst.*, 2002, pp. 9-17, vol. 300, No. 1.
Lee, J. et al. "N-(3-Acyloxy-2-Benzylpropyl)-N'-Dihydroxy tetrahydrobenzazepine and Tetrahydroisoquionline Thiourea Analogs as Vanilloid Receptor Ligands". *BioOrganic & Med. Chem. Elsevier Science Ltd*, 2001, vol. 9, pp. 1713-1720, GB, XP002244787.
Sims, J.J.; et al., "Improvement of A B-Tetralone Synthesis: 5-, 6-, 7- and 8-Methyl-B-Tetralones," *Tetrahedron Letters*, 1971, pp. 951-954, No. 14.
Trivedi, B.K. et al. "A series of conformationally and sterically constrained analogs of N-phenyl-N-aralkylurea acat inhibitors." *BioOrganic & Medicinal Chemistry Letters*, 1995, vol. 5, No., pp. 2229-22334, Oxford, GB XP004135289.
Walpole, C.S.J. et al., "The Discovery of Capsazepine, the First Competitive Antagonist of the Sensory Neuron Excitants Capasaicin and Resiniferatoxin," *J. Med. Chem.*, 1994, pp. 1942-1954, vol. 37.
PCT International Search Report dated Sep. 17, 2003 for PCT Application No. PCT/US03/15254, which relates to U.S. Appl. No. 10/438,477 dated May 15, 2003.
Martinez-Garcia, C. et al., "Attenuation of thermal nociception and hyperalgesia by VR1 blockers." *PNAS.*, 2002, pp. 2374-2379, vol. 99, No. 4.
Gould P.L., "Salt Selection for Basic Drugs.", International J. Pharm., 1986, pp. 201-217, vol. 33.
Berge et al., "Pharmaceutical Salts.", J. Pharm. Sci., 1977, pp. 1-19, vol. 66(1).
Still et al., "Rapid Chromatographic Technique for Preparative Separations with Moderate Resolution.", J. Org. Chem., 1978, pp. 2923-2925, vol. 43(14).

* cited by examiner

*Primary Examiner* — Zinna Northington Davis

(57) ABSTRACT

This invention is directed to vanilloid receptor VR1 ligands. More particularly, this invention relates to β-aminotetralin-derived ureas that are potent antagonists or agonists of VR1 which are useful for the treatment and prevention of inflammatory and other pain conditions in mammals.

52 Claims, 3 Drawing Sheets

AMINOTETRALIN-DERIVED UREA MODULATORS OF VANILLOID VR1 RECEPTOR

CROSS-REFERENCE TO RELATED APPLICATIONS

This application is a continuation of U.S. application Ser. No. 11/877,220, filed on Oct. 23, 2007, now U.S. Pat. No. 7,678,812, which is a continuation of U.S. application Ser. No. 11/045,956, filed on Jan. 28, 2005, now abandoned, which is a divisional of application Ser. No. 10/438,477, filed on May 15, 2003, now U.S. Pat. No. 6,984,647, which claims the benefit of Ser. No. 60/381,575, filed on May 17, 2002, which are hereby incorporated by reference in their entireties.

STATEMENT REGARDING FEDERALLY SPONSORED RESEARCH OR DEVELOPMENT

The research and development of the invention described below was not federally sponsored.

BACKGROUND OF THE INVENTION

This invention is directed to novel vanilloid receptor VR1 ligands. More particularly, this invention relates to novel β-aminotetralin-derived ureas that are potent antagonists or agonists of VR1 and exhibit activity in animal models of hyperalgesia and colitis, and are useful for the treatment and prevention of pain conditions in humans including arthritis, and for the treatment of irritable-bowel syndrome and associated conditions.

Noxious chemical, thermal and mechanical stimuli excite peripheral nerve endings of small diameter sensory neurons (nociceptors) in sensory ganglia (e. g., dorsal root, nodose and trigeminal ganglia) and initiate signals that are perceived as pain. These neurons are crucial for the detection of harmful or potentially harmful stimuli (heat) and tissue damage (local tissue acidosis and/or stretch) that arise from changes in the extracellular space during inflammatory or ischaemic conditions (Wall, P. D., and Melzack, R., *Textbook of Pain,* 1994, New York: Churchill Livingstone). Nociceptors transduce noxious stimuli into membrane depolarization that triggers action potential, conducts the action potential from the sensory sites to the synapses in the CNS, and conversion of action potentials invokes a perception of pain, discomfort, and appropriate mechanical/physical protective reflexes. At the molecular level, nociception is carried out by ion channels or receptors. Plant derived vanilloid compounds (capsaicin and its ultrapotent analog, resiniferatoxin, etc.) are known to selectively depolarize nociceptors and elicit sensations of burning pain—the sensation that is typically obtained by hot chili peppers. Therefore, capsaicin mimics the action of physiological/endogenous stimuli that activates the "nociceptive pathway". Recent advances in pain biology have identified receptors for vanilloids, protons (i.e., acidic solutions), and for heat. Because nociceptors are involved with unwanted pain and inflammatory conditions in human beings and animals, modulation of their nociceptive pathway is important in palliative and other therapies.

Walpole and colleagues at Sandoz reported on the first competitive antagonist of the sensory neuron excitants capsaicin and resiniferatoxin (Walpole, C. S. J. et. al., *J. Med. Chem.* 1994, 37, 1942). Subsequently, capsazepine has been shown to be a vanilloid receptor antagonist. Capsazepine, however, is not aminotetralin-derived. Jee Woo Lee and colleagues at Pacific Corporation disclosed thiocarbamic acid derived VR1 antagonists in WO0216317A1 and vanilloid receptor modulators in WO0216318A1 and WO00216319A1 but these applications do not disclose or describe α-substituted β-aminotetralins. Hutchinson and colleagues at Neurogen describe a diaryl piperazinyl ureas and related compounds as capsaicin receptor ligands in WO02082212A1 but aminotetralins are not covered. Scientists at the Universidad Miguel Hernandez in Alicante, the Universidad de Valencia and the Consejo Superior de Investigaciones Cientificas (CSIC) in Barcelona have used a combinatorial chemistry-based approach to discover compounds that modulate the vanilloid VR1 receptor and have disclosed two trialkylglycine-based compounds as noncompetitive VR1 channel blockers (Garcia-Martinez, C. et al. Proc Natl Acad Sci USA 2002, 99(4): 2374) but none are aminotetralin-derived.

U.S. Pat. Nos. 6,140,354 and 6,201,025 by Dax et. al. teach the synthesis of N-acylated and N-alkylated α-substituted β-aminotetralins but do not describe the synthesis of ureido β-aminotetralins. U.S. Pat. No. 6,169,116 B1 by Swoboda describes β-aminotetralins and their pharmaceutical uses but does not describe the synthesis of α-substituted β-aminotetralins and does not describe the synthesis of ureido β-aminotetralins. European patent application 0064964 by Arvidsson teaches the synthesis of N-alkylated α-alkyl-β-aminotetralins in which the alkyl substituent in the α-position is hydrogen or $C_{1-6}$alkyl but does not describe the synthesis of β-aminotetralins substituted with groups other than hydrogen or $C_{1-6}$alkyl in α-position nor describe the synthesis of ureido β-aminotetralins.

Thus, there is a need for potent modulators of VR, and in particular, for novel β-aminotetralin-derived ureas that exhibit potent binding affinity for the human and rat VR1 ion channel. There is also a need for novel β-amino-tetralin-derived ureas that act as potent functional antagonists and/or agonists of the human and rat VR1 ion channel. Finally, there is a need for novel β-aminotetralin-derived ureas that bind with high affinity to VR1 and also act as potent functional antagonists of the human and rat VR1 ion channel.

SUMMARY OF THE INVENTION

The present invention is directed to compositions comprising a compound of Formula (I):

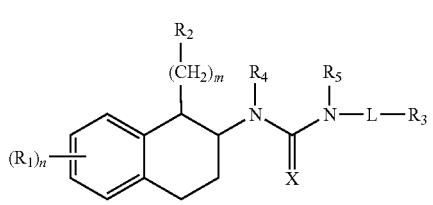

Formula (I)

wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is an integer from 0 to 3;

$R_2$ is independently selected from the group consisting of hydrogen; hydroxy; $C_{1-8}$alkanyl; $C_{2-8}$alkenyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Preferred embodiments of the present invention are those in which: (1) $R_1$ is a substituent independently selected from the group consisting of hydrogen, hydroxy, fluoro, chloro, bromo, and $C_{1-8}$alkanyloxy; (2) $R_1$ is a substituent independently selected from the group consisting of fluoro, chloro, bromo, $C_{1-8}$alkanyloxy, (3) $R_2$ is independently selected from the group consisting of hydrogen, $C_{2-8}$alkenyl, $C_{2-8}$alkenyl, $C_{1-8}$alkylidenyl, $C_{1-8}$alkylidynyl, $C_{3-8}$cycloalkanyl, phenyl (optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl), naphthyl (optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl), and a heteroaryl optionally substituted with one to three substituents independently selected from the group consisting of $C_{1-8}$alkanyl and halogen wherein the heteroaryl is pyridyl, pyrimidyl, furyl, thienyl or imidazolyl; (4) L is a direct bond or $C_{1-8}$alkanylene; and (5) $R_3$ is selected from the group consisting of naphthyl substituted with hydroxyl; quinolinyl optionally substituted with one or more substituents selected from the group consisting of methyl and chloro, quinolinyl-N-oxide, isoquinolinyl optionally substituted with one or more substituents selected from the group consisting of methyl and chloro and isoquinolinyl-N-oxide.

Finally, the present invention is directed to pharamceutical compositions containing compounds of Formula (I), as well as to methods of treatment of diseases and conditions by administration of these compositions, and also to pharmaceutical kits containing them.

DETAILED DESCRIPTION OF THE INVENTION

Figure 1:
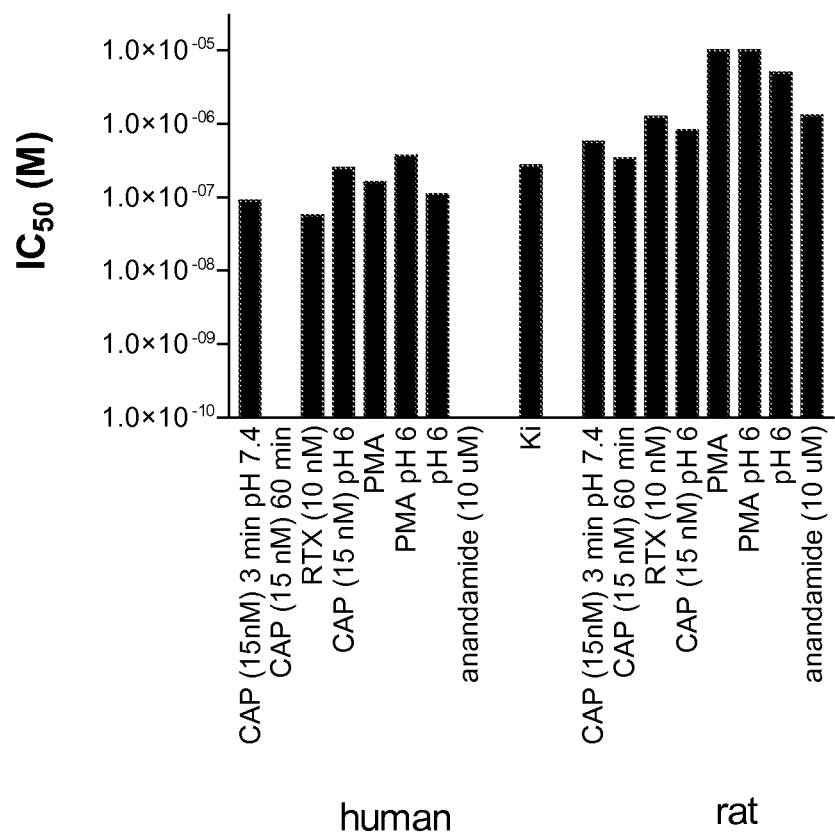
FIG. 1 shows the $IC_{50}$ values of the competitive vanilloid antagonist capsazepine for inhibition of calcium flux induced by a number of different stimuli known to activate VR1.

As used herein, the following underlined terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms.

"Fluorinated alkyl" refers to a saturated branched or straight chain hydrocarbon radical derived by removal of 1 hydrogen atom from the parent alkane; the parent alkane contains from 1 to 6 carbon atoms with 1 or more hydrogen atoms substituted with fluorine atoms up to and including substitution of all hydrogen atoms with fluorine. Preferred fluorinated alkyls include trifluoromethyl substituted alkyls and perfluorinated alkyls; more preferred fluorinated alkyls include trifluoromethyl, perfluoroethyl, 2,2,2-trifluoroethyl, perfluoropropyl, 3,3,3-trifluoroprop-1-yl, 3,3,3-trifluoroprop-2-yl, 1,1,1,3,3,3-hexafluoroprop-2-yl; a particularly preferred fluorinated alkyl is trifluoromethyl.

"Fluorinated alkanyloxy" refers to a radical derived from a fluorinated alkyl radical attached to an oxygen atom with the oxygen atom having one open valence for attachment to a parent structure.

"Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1- en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are $(C_{1-8})$ alkyl, with $(C_{1-3})$ being particularly preferred.]

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred embodiments, the alkanyl groups are $(C_{1-8})$ alkanyl, with $(C_{1-3})$ being particularly preferred.

"Alkenyl:" refers to an unsaturated branched, straight-chain or cyclic monovalent hydrocarbon radical having at least one carbon—carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is $(C_{2-8})$ alkenyl, with $(C_{2-3})$ being particularly preferred.

"Alkynyl:" refers to an unsaturated branched, straight-chain or cyclic monovalent hydrocarbon radical having at least one carbon—carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is $(C_{2-8})$ alkynyl, with $(C_{2-3})$ being particularly preferred.

"Alkyldiyl:" refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methylprop-2-en-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkyndiyl is used. In preferred embodiments, the alkyldiyl group is $(C_{1-8})$ alkyldiyl, with $(C_{1-8})$ being particularly preferred. Also preferred are saturated acyclic alkandiyl radicals in which the radical centers are at the terminal carbons, e.g., methandiyl; ethan-1,2-diyl; propan-1,3-diyl; butan-1,4-diyl; and the like (also referred to as alkylenos, as defined infra).

"Vic Alkyldiyl:" refers to a saturated or unsaturated, branched, straight-chain or cyclic hydrocarbon radical having two adjacent monovalent radical centers derived by the removal of one hydrogen atom from each of two adjacent carbon atoms of a parent alkane, alkene or alkyne. The two monovalent radical centers can form bonds with the same or different atom(s). Typical vic alkyldiyls include, but are not limited to vic ethyldiyls such as ethan-1,2-diyl, ethen-1,2-diyl; vic propyldiyls such as propan-1,2-diyl, cyclopropan-1,2-diyl, prop-1-en-1,2-diyl, prop-2-en-1,2-diyl, cycloprop-1-en-1,2-diyl, etc.; vic butyldiyls such as butan-1,2-diyl, 2-methyl-propan-1,2-diyl, cyclobutan-1,2-diyl, but-1-en-1,2-diyl, cyclobut-1-en-1,2-diyl, buta-1,3-dien-1,2-diyl, cyclobuta-1,3-dien-1,2-diyl, but-3-yn-1,2-diyl, etc.; and the like. Where specific levels of saturation are intended, the nomenclature vic alkandiyl, vic alkendiyl and/or vic alkyndiyl is used. In preferred embodiments, the vic alkyldiyl group is $(C_{2-8})$ vic alkyldiyl, with $(C_{2-3})$ being particularly preferred.

"Gem Alkyldiyl:" refers to a saturated or unsaturated, branched, straight-chain or cyclic hydrocarbon radical having one divalent radical center derived by the removal of two hydrogen atoms from a single carbon atom of a parent alkane, alkene or alkyne. The divalent radical center forms bonds with two different atoms. Typical gem alkyldiyls include, but are not limited to gem methanyldiyl; gem ethyldiyls such as ethan-1,1-diyl, ethen-1,1-diyl; gem propyldiyls such as propan-1,1-diyl, propan-2,2-diyl, cyclopropan-1,1-diyl, prop-1-en-1,1-diyl, cycloprop-2-en-1,1-diyl, prop-2-yn-1,1-diyl, etc.; butyldiyls such as butan-1,1-diyl, butan-2,2-diyl, 2-methyl-propan-1,2-diyl, cyclobutan-1,1-diyl, but-1-en-1,1-diyl, 2-methyl-prop-1-en-1,1-diyl, 2-methyl-prop-2-en-1,1-diyl, cyclobut-2-en-1,1-diyl, buta-1,3-dien-1,1-diyl, etc.; and the like. Where specific levels of saturation are intended, the nomenclature gem alkandiyl, gem alkendiyl and/or gem alkyndiyl is used. In preferred embodiments, the gem alkyldiyl group is $(C_{1-6})$ gem alkyldiyl, with $(C_{1-3})$ being particularly preferred.

"Alkyleno:" refers to a saturated or unsaturated, straight-chain or branched acyclic bivalent hydrocarbon bridge radical derived by the removal of one hydrogen atom from each of the two terminal carbon atoms of an acyclic parent alkane, alkene or alkyne. Typical alkyleno groups include, but are not limited to, methano; ethylenos such as ethano, etheno, ethyno; propylenos such as propano, propeno, prop-1,2-dieno, propyno, etc.; butylenos such as butano, 2-methyl-propano, but-1-eno, but-2-eno, 2-methyl-prop-1-eno, 2-methanylidene-propano, but-1,3-dieno, but-1-yno, but-2-yno, but-1,3-diyno, etc.; and the like. Where specific levels of saturation are intended, the nomenclature alkano, alkeno and/or alkyno is used. In preferred embodiments, the alkyleno group is $(C_{1-8})$ alkyleno, with $(C_{1-3})$ being particularly preferred. Also preferred are straight-chain saturated alkano radicals, e.g., methano, ethano, propano, butano, and the like.

"Alkylidene:" refers to a saturated or unsaturated, branched, straight-chain or cyclic divalent hydrocarbon radical derived by removal of two hydrogen atoms from the same carbon atom of a parent alkane, alkene or alkyne. The divalent radical center forms a double bond with a single atom. Typical alkylidene radicals include, but are not limited to, methanylidene, ethylidenes such as ethanylidene, ethenylidene; propylidenes such as propan-1-ylidene, propan-2-ylidene, cyclopropan-1-ylidene, prop-1-en-1-ylidene, prop-2-en-1-ylidene, cycloprop-2-en-1-ylidene, etc.; butylidenes such as butan-1-ylidene, butan-2-ylidene, 2-methyl-propan-1-ylidene, cyclobutan-1-ylidene, but-1-en-1-ylidene, but-2-en-1-ylidene, but-3-en-1-ylidene, buta-1,3-dien-1-ylidene; cyclobut-2-en-1-ylidene, etc.; and the like. Where specific levels of saturation are intended, the nomenclature alkanylidene, alkenylidene and/or alkynylidene is used. In preferred embodiments, the alkylidene group is $(C_{1-8})$ alkylidene, with $(C_{1-3})$ being particularly preferred. Also preferred are acyclic saturated alkanylidene radicals in which the divalent radical is at a terminal carbon, e.g., methanylidene, ethan-1-ylidene, propan-1-ylidene, butan-1-ylidene, 2-methyl-propan-1-ylidene, and the like.

"Alkylidyne:" refers to a saturated or unsaturated, branched or straight-chain trivalent hydrocarbon radical derived by removal of three hydrogen atoms from the same carbon atom of a parent alkane, alkene or alkyne. The trivalent radical center forms a triple bond with a single atom. Typical alkylidyne radicals include, but are not limited to, methanylidyne; ethanylidyne; propylidynes such as propan-1-ylidyne, prop-2-en-1-ylidyne, prop-2-yn-1-ylidyne; butylidynes such as butan-1-ylidyne, 2-methyl-propan-1-ylidyne, but-2-en-1-ylidyne, but-3-en-1-ylidyne, buta-2,3-dien-1-ylidyne, but-2-yn-1-ylidyne, but-3-yn-1-ylidyne, etc.; and the like. Where specific levels of saturation are intended, the nomenclature alkanylidyne, alkenylidyne and/or alkynylidyne is used. In preferred embodiments, the alkylidyne group is $(C_{1-8})$ alkylidyne, with $(C_{1-3})$ being particularly preferred. Also preferred are saturated alkanylidyne radicals, e.g., methanylidyne, ethanylidyne, propan-1-ylidyne, butan-1-ylidyne, 2-methyl-propan-1-ylidyne, and the like.

"Heteroalkyl, Heteroalkanyl, Heteroalkenyl, Heteroalkynyl, Heteroalkylidene, Heteroalkylidyne, Heteroalkyldiyl, Vic Heteralkyldiyl, Gem Heteroalkyldiyl, Heteroalkyleno and Heteroalkyldiylidene:" refer to alkyl, alkanyl, alkenyl, alkynyl, alkylidene, alkylidyne, alkyldiyl, vic alkyldiyl, gem alkyldiyl, alkyleno and alkyldiylidene radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkyl, heteroalkanyl, heteroalkenyl, heteroalkynyl, heteroalkylidene, heteroalkylidyne, heteroalkyldiyl, vic heteroalkyldiyl, gem heteroalkyldiyl, heteroalkyleno and heteroalkyldiylidene radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimmino (—NR'—NR'—), azino (=N—N=), azo (—N=N—), azoxy (—N—O—N—), azimino (—NR'—N=N—), phosphano (—PH—), $\lambda^4$-sulfano (—SH$_2$—), sulfonyl (—S(O)$_2$—), and the like, where each R' is independently hydrogen or $(C_1$-$C_6)$ alkyl.

"Parent Aromatic Ring System:" refers to an unsaturated cyclic or polycyclic ring system having a conjugated π electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like "Aryl:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is $(C_{5-20})$ aryl, with $(C_{5-10})$ being particularly preferred. Particularly preferrec aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. [In preferred embodiments, the arylalkyl group is $(C_{6-26})$ arylalkyl, e.g., the alkanyl, alkenyl or alkynyl moiety of the arylalkyl group is $(C_{1-6})$ and the aryl moiety is $(C_{5-20})$. In particularly preferred embodiments the arylalkyl group is $(C_{6-13})$, e.g., the alkanyl, alkenyl or alkynyl moiety of the arylalkyl group is $(C_{1-3})$ and the aryl moiety is $(C_{5-10})$. Even more preferred arylalkyl groups are phenylalkanyls.

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyl; ethanyloxy; propanyloxy groups such as propan-1-yloxy ($CH_3CH_2CH_2O$—), propan-2-yloxy ($(CH_3)_2CHO$—), cyclopropan-1-yloxy, etc.; butyanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are $(C_{1-8})$ alkanyloxy groups, with $(C_{1-3})$ being particularly preferred.

"Parent Heteroaromatic Ring System:" refers to a parent aromatic ring system in which one or more carbon atoms are each independently replaced with a heteroatom. Typical heteratoms to replace the carbon atoms include, but are not limited to, N, P, O, S, Si etc. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred. Specific preferred heteroaryls for the present invention are quinoline, isoquinoline, pyridine, pyrimidine, furan, thiophene and imidazole.

"Substituted:" refers to a radical in which one or more hydrogen atoms are each independently replaced with the same or different substituent(s). Typical substituents include, but are not limited to, —X, —R, —O⁻, =O, —OR, —O—OR, —SR, —S⁻, =S, —NRR, =NR, —CX$_3$, —CN, —OCN, —SCN, —NCO, —NCS, —NO, —NO$_2$, =N$_2$, —N$_3$, —NHOH, —S(O)$_2$O⁻, —S(O)$_2$OH, —S(O)$_2$R, —P(O)(O⁻)$_2$, —P(O)(OH)$_2$, —C(O)R, —C(O)X, —C(S)R, —C(S)X, —C(O)OR, —C(O)O⁻, —C(S)OR, —C(O)SR, —C(S)SR, —C(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, C$_{1-8}$alkyl, C$_{1-8}$alkanyloxy, fluorinated alkanyloxy, fluorinated alkyl, C$_{1-8}$alkylthio, C$_{3-8}$cycloalkyl, C$_{3-8}$cycloalkanyloxy, nitro, amino, C$_{1-8}$alkylamino, C$_{1-8}$dialkylamino, C$_{3-8}$cycloalkylamino, cyano, carboxy, C$_{1-7}$alkanyloxycarbonyl, C$_{1-7}$alkylcarbonyloxy, formyl, carbamoyl, phenyl, aroyl, carbamoyl, amidino, (C$_{1-8}$alkylamino)carbonyl, (arylamino)carbonyl and aryl(C$_{1-8}$alkyl)carbonyl, "Aroyl" refers to arylacyl substituents.

"Acyl" refers to alkylcarbonyl substituents.

With reference to substituents, the term "independently" means that when more than one of such substituent is possible, such substituents may be the same or different from each other.

Throughout this disclosure, the terminal portion of the designated side chain is described first, followed by the adjacent functionality toward the point of attachment. Thus, for example, a "phenylC$_{1-6}$alkanylaminocarbonylC$_{1-6}$alkyl" substituent refers to a group of the formula

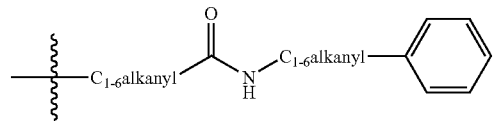

The present invention is directed to compositions comprising a compound of Formula (I):

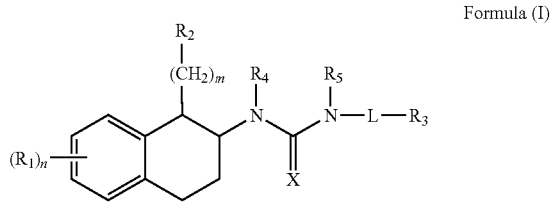

Formula (I)

wherein R$_1$ independently may be absent or an optionally substituted substituent selected from alkyl, heteroalkyl, aryl (preferably 5-10 membered aryl), arylalkyl, halogen, nitro, amino, cyano, carboxy, carbamoyl, aroyl, amidino, and acyl; n is an integer from 1 to 3; m is an integer from 0 to 3; R$_2$ may be absent or an optionally substituted substituent selected from alkyl, heteroalkyl, aryl (preferably 5-10 membered aryl), heteroaryl (preferably 5-10 membered heteroaryl), alkylidenyl, heteroalkylidenyl, alkylidynyl, heteroalkylidynyl, arylalkyl, halogen, nitro, amino, and cyano; L is a direct bond, alkyldiyl or heteroalkyldiyl; R$_3$ is aryl (preferably 5-10 membered aryl) or heteroaryl (preferably 5-10 membered heteroaryl); R$_4$ and R$_5$ are hydrogen, alkyl, or heteroalkyl; X is O or S; and enantiomers, diastereomers, tautomers, solvates, and pharmaceutically acceptable salts thereof.

In particular, the present invention is directed to compounds of Formula (I) wherein:

R$_1$ is a substituent independently selected from the group consisting of hydrogen; hydroxy; halogen; C$_{1-8}$alkanyl optionally substituted with one or more substituents independently selected from the group consisting of halogen, fluorinated alkanyl and C$_{1-8}$alkanyloxy; C$_{1-8}$alkanyloxy optionally substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cycloalkanylamino; cyano; carboxy; C$_{1-7}$alkanyloxycarbonyl; C$_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; (C$_{1-8}$alkanylamino)carbonyl; (arylamino)carbonyl and aryl(C$_{1-8}$alkanyl)carbonyl;

n is an integer from 1 to 3;

m is an integer from 0 to 3;

R$_2$ is independently selected from the group consisting of hydrogen; hydroxy; C$_{1-8}$alkanyl; C$_{2-8}$alkenyl; C$_{1-8}$alkylidenyl; C$_{1-8}$alkylidynyl; ; fluoro; chloro; C$_{3-8}$cycloalkanyl; phenyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-8}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Preferred embodiments of the present invention are those in which: (1) $R_1$ is a substituent independently selected from the group consisting of hydrogen, hydroxy, fluoro, chloro, bromo, and $C_{1-8}$alkanyloxy; (2) $R_1$ is a substituent independently selected from the group consisting of fluoro, chloro, bromo, $C_{1-8}$alkanyloxy, (3) $R_2$ is independently selected from the group consisting of hydrogen, $C_{2-8}$alkenyl, $C_{1-8}$alkylidenyl, $C_{1-8}$alkylidynyl, $C_{3-8}$cycloalkanyl, phenyl (optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl), naphthyl (optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl), and a heteroaryl optionally substituted with one to three substituents independently selected from the group consisting of $C_{1-8}$alkanyl and halogen wherein the heteroaryl is pyridyl, pyrimidyl, furyl, thienyl or imidazolyl; (4) L is a direct bond or $C_{1-8}$alkandiyl; (5) $R_3$ is selected from the group consisting of naphthyl substituted with hydroxyl; quinolinyl and isoquinolinyl; and (6) any combination of (1) to (5) preceding. Thus, preferred embodiments of the present invention are as described below.

An embodiment of the present invention is directed to compositions comprising a compound of Formula (I) wherein:

$R_1$ is a substituent independently selected from the group consisting of hydrogen; hydroxy; fluoro; chloro; and $C_{1-8}$alkanyloxy;

n is an integer from 1 to 3;

m is an integer from 0 to 3;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-8}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Another embodiment of the present invention is directed to compositions comprising a compound of Formula (I) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is an integer from 0 to 3;

$R_2$ is independently selected from the group consisting of hydrogen; $C_{2-8}$alkenyl; $C_{1-8}$alkylidenyl; $C_{1-8}$alkylidynyl; $C_{3-8}$cycloalkanyl; phenyl optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, fluorinated alkanyl; naphthyl optionally substituted with one to three substituents independently selected from the group consisting of fluoro, chloro, bromo, hydroxy, $C_{1-8}$alkanyl, $C_{1-8}$alkanyloxy, phenyl ($C_{1-8}$)alkanyloxy, fluorinated alkanyl; and a heteroaryl optionally substituted with one to three substituents independently selected from the group consisting of $C_{1-6}$alkanyl and halogen wherein said heteroaryl is pyridyl, pyrimidyl, furyl, thienyl or imidazolyl;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Still another embodiment of the present invention is directed to compositions comprising a compound of Formula (I) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$al-kanylamino)carbonyl; (arylamino)carbonyl and aryl($C_{1-8}$alkanyl)carbonyl;

n is an integer from 1 to 3;

m is an integer from 0 to 3;

$R_2$ is independently selected from the group consisting of hydrogen; $C_{2-8}$alkenyl; $C_{1-8}$alkylidenyl; $C_{1-8}$alkylidynyl; $C_{3-8}$cycloalkanyl; phenyl optionally substituted with one to three substituents independently selected from the group consisting of fluoro, chloro, bromo, $C_{1-8}$alkanyloxy, phenyl ($C_{1-8}$)alkanyloxy and fluorinated alkanyl; naphthyl optionally substituted with one to three substituents independently selected from the group consisting of fluoro, chloro, bromo, $C_{1-8}$alkanyloxy, phenyl($C_{1-8}$)alkanyloxy and fluorinated alkanyl; pyridyl; pyrimidyl; furyl; thienyl and imidazolyl.

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Furthermore, another embodiment of the present invention is directed to compositions comprising a compound of Formula (I) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is an integer from 0 to 3;

$R_2$ is independently selected from the group consisting of $C_{2-8}$alkenyl; $C_{1-8}$alkylidenyl; $C_{1-8}$alkylidynyl; $C_{3-8}$cycloalkanyl; phenyl optionally substituted with one to three substituents independently selected from the group consisting of fluoro, chloro, bromo, and fluorinated alkanyl.

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

An embodiment of the present invention is directed to compositions comprising a compound of Formula (I) wherein:

$R_1$ is a substituent independently selected from the group consisting of fluoro; chloro; $C_{1-8}$alkanyloxy;

n is an integer from 1 to 3;

m is an integer from 0 to 3;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-8}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl,quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Another embodiment of the present invention is directed to compositions comprising a compound of Formula (I) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is 1;

m is an integer from 0 to 3;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Still yet another embodiment of the present invention is directed to compositions comprising a compound of Formula (I) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is an integer from 0 to 1;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-8}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Another embodiment of the present invention is directed to compositions comprising a compound of Formula (I) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is 1;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Another embodiment of the present invention is directed to compositions comprising a compound of Formula (I) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is an integer from 0 to 3;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-8}$alkanyl and halogen wherein said heteroaryl is pyridyl, pyrimidyl, furyl, thienyl or imidazolyl; pyrrolidino; and piperidino;

L is a direct bond or $C_{1-8}$alkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Yet another embodiment of the present invention is directed to compositions comprising a compound of Formula (I) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is an integer from 0 to 3;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Still yet another embodiment of the present invention is directed to compositions comprising a compound of Formula (I) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is an integer from 0 to 3;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl substituted with one to three substituents independently selected from the group consisting of $C_{1-8}$alkanyl, fluoro, chloro, bromo, $C_{1-8}$alkanyloxy, hydroxy, fluorinated alkanyl, nitro, amino, di($C_{1-8}$)alkanylamino, $C_{1-8}$alkanylamino and cyano; naphthyl substituted with one to three substituents independently selected from the group consisting of $C_{1-8}$alkanyl, fluoro, chloro, bromo, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, fluoro and chloro, wherein said heteroaryl is quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Furthermore, another embodiment of the present invention is directed to compositions comprising a compound of Formula (I) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is an integer from 0 to 3;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl substituted with one to three substituents independently selected from the group consisting of $C_{1-8}$alkanyloxy and hydroxy; naphthyl substituted with one to three substituents independently selected from the group consisting of $C_{1-8}$alkanyloxy and hydroxy; and heteroaryl optionally substituted with one to three substituents independently selected from the group consisting of $C_{1-8}$alkanyl and chloro wherein said heteroaryl is quinolinyl-N-oxide, isoquinolinyl, isoquinolinyl-N-oxide, pyridyl and pyridyl-N-oxide;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Another embodiment of the present invention is directed to compositions comprising a compound of Formula (I) wherein $R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is an integer from 0 to 3;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of naphthyl substituted with hydroxyl; quinolinyl optionally substituted with one or more substituents selected from the group consisting of methyl and chloro, quinolinyl-N-oxide, isoquinolinyl optionally substituted with one or more substituents selected from the group consisting of methyl and chloro and isoquinolinyl-N-oxide;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Another embodiment of the present invention is directed to compositions comprising a compound of Formula (I) wherein:

$R_1$ is a substituent independently selected from the group consisting of hydrogen; hydroxy; halogen; $C_{1-8}$alkanyl optionally independently substituted with one or more substituents independently selected from the group consisting of halogen, fluorinated alkanyl and $C_{1-8}$alkanyloxy; $C_{1-8}$alkanyloxy optionally independently substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is an integer from 0 to 3;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is 2-hydroxynaphth-8-yl, isoquinolin-5-yl and isoquinolinyl-5-yl-N-oxide;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Yet another embodiment of the present invention is directed to compositions comprising a compound of Formula (I) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;
m is an integer from 0 to 3;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-8}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is hydrogen;

$R_5$ is selected from the group consisting of hydrogen and $C_{1-8}$alkanyl;

X is selected from the group consisting of O and S; and enantiomers, diastereomers, tautomers, solvates, and pharmaceutically acceptable salts thereof.

Still yet another embodiment of the present invention is directed to compositions comprising a compound of Formula (I) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;
m is an integer from 0 to 3;

$R_2$ is independently selected from the group consisting of hydrogen;

hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

R₄ is selected from the group consisting of hydrogen and C$_{1-8}$alkanyl;

R₅ is hydrogen;

X is selected from the group consisting of O and S; and enantiomers, diastereomers, tautomers, solvates, and pharmaceutically acceptable salts thereof.

Furthermore, another embodiment of the present invention is directed to compositions comprising a compound of Formula (I) wherein:

R₁ is a substituent independently selected from the group consisting of hydrogen; hydroxy; halogen; C$_{1-8}$alkanyl optionally substituted with one or more substituents independently selected from the group consisting of halogen, fluorinated alkanyl and C$_{1-8}$alkanyloxy; C$_{1-8}$alkanyloxy optionally substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cycloalkanylamino; cyano; carboxy; C$_{1-7}$alkanyloxycarbonyl; C$_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; (C$_{1-8}$alkanylamino)carbonyl; (arylamino)carbonyl and aryl(C$_{1-8}$alkanyl)carbonyl;

n is an integer from 1 to 3;

m is an integer from 0 to 3;

R₂ is independently selected from the group consisting of hydrogen; hydroxy; C$_{1-8}$alkanyl; C$_{2-8}$alkenyl; C$_{1-8}$alkylidenyl; C$_{1-8}$alkylidynyl; fluoro; chloro; C$_{3-8}$cycloalkanyl; phenyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; naphthyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; phenoxy optionally substituted with one to three substituents independently selected from the group consisting of halogen, hydroxy, C$_{1-8}$alkanyl, C$_{1-8}$alkanyloxy, fluorinated alkanyl, cyano and nitro; and heteroaryl optionally substituted with one to three substituents independently selected from the group consisting of C$_{1-6}$alkanyl and halogen wherein said heteroaryl is pyridyl, pyrimidyl, furyl, thienyl or imidazolyl; pyrrolidino; and piperidino;

L is a direct bond, C$_{1-8}$alkandiyl, C$_{2-8}$alkendiyl, C$_{2-8}$alkyndiyl, or C$_{3-8}$cycloalkandiyl;

R₃ is selected from the group consisting of phenyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; naphthyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; and heteroaryl optionally substituted with one to three substituents independently selected from the group consisting of C$_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

R₄ is selected from the group consisting of hydrogen and C$_{1-8}$alkanyl;

R₅ is selected from the group consisting of hydrogen and C$_{1-8}$alkanyl;

X is O; and enantiomers, diastereomers, tautomers, solvates, and pharmaceutically acceptable salts thereof.

Another embodiment of the present invention is directed to compositions comprising a compound of Formula (Ia):

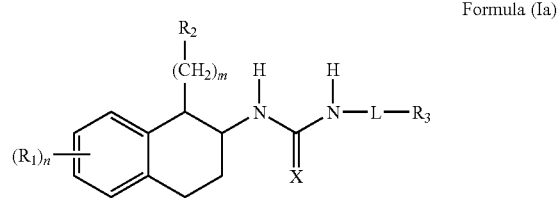

Formula (Ia)

the compound selected from the group consisting of:

a compound of formula (Ia) wherein R₁ is 6-F, R₂ is 3-Pyridinyl, m is 1, L is —CH₂—, R₃ is (3-OMe-4-OH)Ph, and X is S;

a compound of formula (Ia) wherein R₁ is 6-OMe, R₂ is H, m is 0, L is —CH₂—, R₃ is (3-OMe-4-OH)Ph, and X is S;

a compound of formula (Ia) wherein R₁ is 6-OMe, R₂ is Ph, m is 1, L is —CH₂—, R₃ is (3-OMe-4-OH)Ph, and X is S;

a compound of formula (Ia) wherein R₁ is H, R₂ is 3-Pyridinyl, m is 1, L is —CH₂—, R₃ is (3-OMe-4-(Methoxymethyleneoxy)Ph, and X is S;

a compound of formula (Ia) wherein R₁ is H, R₂ is 3-Pyridinyl, m is 1, L is —CH₂—, R₃ is (3-OMe-4-OH)Ph, and X is S;

a compound of formula (Ia) wherein R₁ is 6-OMe, R₂ is 3-Pyridinyl, m is 1, L is —CH₂—, R₃ is (3-OMe-4-OH)Ph, and X is S;

a compound of formula (Ia) wherein R₁ is 6-OMe, R₂ is —CH=CH₂, m is 1, L is —CH₂—, R₃ is (3-OMe-4-(Methoxymethyleneoxy)Ph, and X is S;

a compound of formula (Ia) wherein R₁ is 6-OMe, R₂ is 4-Imidazolyl, m is 1, L is —CH₂—, R₃ is (3-OMe-4-OH)Ph, and X is S;

a compound of formula (Ia) wherein R₁ is 6-OMe, R₂ is Ph, m is 1, L is —CH₂—, R₃ is (3,4-methylenedioxy)Ph, and X is O;

a compound of formula (Ia) wherein R₁ is 6-OMe, R₂ is Ph, m is 1, L is —CH₂—, R₃ is (3,4-diOMe)Ph, and X is O;

a compound of formula (Ia) wherein R₁ is 6-OMe, R₂ is Ph, m is 1, L is —CH₂—, R₃ is (4-tBu)Ph, and X is O;

a compound of formula (Ia) wherein R₁ is 6-OMe, R₂ is Ph, m is 1, L is —CH₂CH₂—, R₃ is (4-Cl)Ph, and X is O;

a compound of formula (Ia) wherein R₁ is 6-OMe, R₂ is Ph, m is 1, L is —CH₂CH₂—, R₃ is (3,4-diOMe)Ph, and X is O;

a compound of formula (Ia) wherein R₁ is 6-OMe, R₂ is Ph, m is 1, L is —CH₂—, R₃ is (3,4-methylenedioxy)Ph, and X is S;

a compound of formula (Ia) wherein R₁ is 6-OMe, R₂ is Ph, m is 1, L is —CH₂—, R₃ is (3,4-diOMe)Ph, and X is S;

a compound of formula (Ia) wherein R₁ is 6-OMe, R₂ is Ph, m is 1, L is —CH₂—, R₃ is (4-tBu)Ph, and X is S;

a compound of formula (Ia) wherein R₁ is 6-OMe, R₂ is Ph, m is 1, L is —CH₂—, R₃ is (4-Cl)Ph, and X is S;

a compound of formula (Ia) wherein R₁ is 6-OMe, R₂ is Ph, m is 1, L is —CH₂CH₂—, R₃ is (3,4-diOMe)Ph, and X is S;

a compound of formula (Ia) wherein $R_1$ is 6-OMe, $R_2$ is Ph, m is 1, L is —CH$_2$—, $R_3$ is (3-OMe-4-OH)Ph, and X is O;

a compound of formula (Ia) wherein $R_1$ is 6-OMe, $R_2$ is Ph, m is 1, L is —CH=CH-Q, $R_3$ is (3-OMe-4-OH)Ph, and X is O;

a compound of formula (Ia) wherein $R_1$ is H, $R_2$ is Ph, m is 1, L is —CH$_2$—, $R_3$ is (3-OMe-4-(Methoxymethyleneoxy)Ph, and X is S;

a compound of formula (Ia) wherein $R_1$ is H, $R_2$ is Ph, m is 1, L is —CH$_2$—, $R_3$ is (3-OMe-4-OH)Ph, and X is S;

a compound of formula (Ia) wherein $R_1$ is 6-OMe, $R_2$ is Ph, m is 1, L is —CH$_2$—, $R_3$ is (4-N(Me)(C$_5$H$_{11}$))Ph, and X is O;

a compound of formula (Ia) wherein $R_1$ is 6-OMe, $R_2$ is Ph, m is 1, L is —CH$_2$—, $R_3$ is (4-[N(Me)(cyclohexyl)])Ph, and X is O;

a compound of formula (Ia) wherein $R_1$ is 6-F, $R_2$ is Ph, m is 1, L is —CH$_2$—, $R_3$ is (3,4-diOMe)Ph, and X is S;

a compound of formula (Ia) wherein $R_1$ is 6-OMe, $R_2$ is Ph, m is 1, L is —CH$_2$—, $R_3$ is (4-CF$_3$)Ph, and X is O;

a compound of formula (Ia) wherein $R_1$ is 6-OMe, $R_2$ is Ph, m is 1, L is —CH$_2$—, $R_3$ is (3,4-diCl)Ph, and X is O;

a compound of formula (Ia) wherein $R_1$ is 6-OMe, $R_2$ is Ph, m is 1, L is —CH$_2$CH$_2$—, $R_3$ is (3,4-diCl)Ph, and X is O;

a compound of formula (Ia) wherein $R_1$ is 6-OMe, $R_2$ is Ph, m is 1, L is —CH$_2$—, $R_3$ is (4-CF$_3$)Ph, and X is S;

a compound of formula (Ia) wherein $R_1$ is 6-OMe, $R_2$ is Ph, m is 1, L is —CH$_2$—, $R_3$ is (3,4-diCl)Ph, and X is S;

a compound of formula (Ia) wherein $R_1$ is 6-OMe, $R_2$ is Ph, m is 1, L is —CH$_2$CH$_2$—, $R_3$ is (3,4-diCl)Ph, and X is S;

a compound of formula (Ia) wherein $R_1$ is 6-OMe, $R_2$ is Ph, m is 1, L is a direct bond, $R_3$ is 5-isoquinolinyl, and X is O;

a compound of formula (Ia) wherein $R_1$ is 6-OMe, $R_2$ is Ph, m is 1, L is a direct bond, $R_3$ is 3-quinolinyl, and X is O;

a compound of formula (Ia) wherein $R_1$ is 6-OMe, $R_2$ is Ph, m is 1, L is a direct bond, $R_3$ is 8-(2-naphtholyl), and X is O;

a compound of formula (Ia) wherein $R_1$ is H, $R_2$ is H, m is 0, L is a direct bond, $R_3$ is 5-isoquinolinyl, and X is O;

a compound of formula (Ia) wherein $R_1$ is 6-F, $R_2$ is H, m is 0, L is a direct bond, $R_3$ is 5-isoquinolinyl, and X is O;

a compound of formula (Ia) wherein $R_1$ is 6-F, $R_2$ is Ph, m is 1, L is a direct bond, $R_3$ is 5-isoquinolinyl, and X is O;

a compound of formula (Ia) wherein $R_1$ is 6-Br, $R_2$ is Ph, m is 1, L is a direct bond, $R_3$ is 5-isoquinolinyl, and X is O;

a compound of formula (Ia) wherein $R_1$ is 6,7-diOMe, $R_2$ is Ph, m is 1, L is a direct bond, $R_3$ is 5-isoquinolinyl, and X is O;

a compound of formula (Ia) wherein $R_1$ is 7-Cl, $R_2$ is Ph, m is 1, L is a direct bond, $R_3$ is 5-isoquinolinyl, and X is O;

a compound of formula (Ia) wherein $R_1$ is 5-Cl, $R_2$ is Ph, m is 1, L is a direct bond, $R_3$ is 5-isoquinolinyl, and X is O;

a compound of formula (Ia) wherein $R_1$ is H, $R_2$ is Ph, m is 1, L is a direct bond, $R_3$ is 5-isoquinolinyl, and X is O;

a compound of formula (Ia) wherein $R_1$ is 6-OMe, $R_2$ is (3-Cl)Ph, m is 1, L is a direct bond, $R_3$ is 5-isoquinolinyl, and X is O;

a compound of formula (Ia) wherein $R_1$ is 6-OMe, $R_2$ is 3-Pyridinyl, m is 1, L is a direct bond, $R_3$ is 5-isoquinolinyl, and X is O;

a compound of formula (Ia) wherein $R_1$ is 6-OMe, $R_2$ is (3-Cl)Ph, m is 1, L is a direct bond, $R_3$ is 5-isoquinolinyl, and X is O;

a compound of formula (Ia) wherein $R_1$ is 6-OMe, $R_2$ is 3-Pyridinyl, m is 1, L is a direct bond, $R_3$ is 5-isoquinolinyl, and X is O;

a compound of formula (Ia) wherein $R_1$ is 6,7-diOMe, $R_2$ is Ph, m is 1, L is a direct bond, $R_3$ is 5-isoquinolinyl, and X is O;

a compound of formula (Ia) wherein $R_1$ is 6-OMe, $R_2$ is (2-Cl)Ph, m is 1, L is a direct bond, $R_3$ is 5-isoquinolinyl, and X is O;

a compound of formula (Ia) wherein $R_1$ is 6-OMe, $R_2$ is (4-Cl)Ph, m is 1, L is a direct bond, $R_3$ is 5-isoquinolinyl, and X is O;

a compound of formula (Ia) wherein $R_1$ is 6-OMe, $R_2$ is H, m is 0, L is a direct bond, $R_3$ is 5-isoquinolinyl, and X is O;

a compound of formula (Ia) wherein $R_1$ is 6-OMe, $R_2$ is (2-Cl)Ph, m is 1, L is a direct bond, $R_3$ is 5-isoquinolinyl, and X is O;

a compound of formula (Ia) wherein $R_1$ is 6-OMe, $R_2$ is (2-CF$_3$)Ph, m is 1, L is a direct bond, $R_3$ is 5-isoquinolinyl, and X is O;

a compound of formula (Ia) wherein $R_1$ is 6-OMe, $R_2$ is (3-CF$_3$)Ph, m is 1, L is a direct bond, $R_3$ is 5-isoquinolinyl, and X is O;

a compound of formula (Ia) wherein $R_1$ is 6-OMe, $R_2$ is (4-CF$_3$)Ph, m is 1, L is a direct bond, $R_3$ is 5-isoquinolinyl, and X is O;

a compound of formula (Ia) wherein $R_1$ is 6-OH, $R_2$ is Ph, m is 1, L is a direct bond, $R_3$ is 5-isoquinolinyl, and X is O;

a compound of formula (Ia) wherein $R_1$ is H, $R_2$ is —CH=CH$_2$, m is 1, L is a direct bond, $R_3$ is 5-isoquinolinyl, and X is O;

a compound of formula (Ia) wherein $R_1$ is 6-Br, $R_2$ is H, m is 0, L is a direct bond, $R_3$ is 5-isoquinolinyl, and X is O;

a compound of formula (Ia) wherein $R_1$ is 6-Cl, $R_2$ is H, m is 0, L is a direct bond, $R_3$ is 5-isoquinolinyl, and X is O;

a compound of formula (Ia) wherein $R_1$ is 6-F, $R_2$ is Ph, m is 1, L is —CH$_2$—, $R_3$ is 5-isoquinolinyl, and X is O;

a compound of formula (Ia) wherein $R_1$ is 7-Cl, $R_2$ is H, m is 0, L is a direct bond, $R_3$ is 5-isoquinolinyl, and X is O;

a compound of formula (Ia) wherein $R_1$ is 8-Cl, $R_2$ is Ph, m is 1, L is a direct bond, $R_3$ is 5-isoquinolinyl, and X is O;

a compound of formula (Ia) wherein $R_1$ is 6-OMe, $R_2$ is (4-CN)Ph, m is 1, L is a direct bond, $R_3$ is 5-isoquinolinyl, and X is O;

a compound of formula (Ia) wherein $R_1$ is 6-OMe, $R_2$ is (4-Br)Ph, m is 1, L is a direct bond, $R_3$ is 5-isoquinolinyl, and X is O;

a compound of formula (Ia) wherein $R_1$ is 6-Cl, $R_2$ is CN, m is 1, L is a direct bond, $R_3$ is 5-isoquinolinyl, and X is O;

a compound of formula (Ia) wherein $R_1$ is 6,7-diF, $R_2$ is Ph, m is 1, L is a direct bond, $R_3$ is 5-isoquinolinyl, and X is O;

a compound of formula (Ia) wherein $R_1$ is 6-F, $R_2$ is Ph, m is 1, L is a direct bond, $R_3$ is 8-(2-naphtholyl), and X is O;

a compound of formula (Ia) wherein $R_1$ is 6-OMe, $R_2$ is —CH=CH$_2$, m is 1, L is a direct bond, $R_3$ is 5-isoquinolinyl, and X is O;

a compound of formula (Ia) wherein $R_1$ is 6-F, $R_2$ is —CH=CH$_2$, m is 1, L is a direct bond, $R_3$ is 5-isoquinolinyl, and X is O;

a compound of formula (Ia) wherein $R_1$ is 6-OMe, $R_2$ is (4-OMe)Ph, m is 1, L is a direct bond, $R_3$ is 5-isoquinolinyl, and X is O;

a compound of formula (Ia) wherein $R_1$ is 6-F, $R_2$ is Cyclopropyl, m is 1, L is a direct bond, $R_3$ is 5-isoquinolinyl, and X is O;

a compound of formula (Ia) wherein $R_1$ is 6-OMe, $R_2$ is (4-OMe)Ph, m is 1, L is a direct bond, $R_3$ is 5-isoquinolinyl, and X is O;

a compound of formula (Ia) wherein $R_1$ is 6-OMe, $R_2$ is (2-OMe)Ph, m is 1, L is a direct bond, $R_3$ is 5-isoquinolinyl, and X is O;

a compound of formula (Ia) wherein $R_1$ is 6-OMe, $R_2$ is (4-Benzyloxy)Ph, m is 1, L is a direct bond, $R_3$ is 5-isoquinolinyl, and X is O;

a compound of formula (Ia) wherein $R_1$ is 6-OMe, $R_2$ is Ph, m is 1, L is —$CH_2$—, $R_3$ is 4-Pyridinyl, and X is O;

a compound of formula (Ia) wherein $R_1$ is 6-F, $R_2$ is 2-Thienyl, m is 1, L is a direct bond, $R_3$ is 5-isoquinolinyl, and X is O;

a compound of formula (Ia) wherein $R_1$ is 6-OMe, $R_2$ is (2,6-diF)Ph, m is 1, L is a direct bond, $R_3$ is 5-isoquinolinyl, and X is O;

a compound of formula (Ia) wherein $R_1$ is 6-OMe, $R_2$ is —$CH_2$=$CH_2$, m is 1, L is —$CH_2$—, $R_3$ is (3-OMe-4-OH)Ph, and X is S;

a compound of formula (Ia) wherein $R_1$ is 7-F, $R_2$ is Ph, m is 1, L is —$CH_2$—, $R_3$ is (3-OMe-4-OH)Ph, and X is S;

a compound of formula (Ia) wherein $R_1$ is 5-F, $R_2$ is Ph, m is 1, L is —$CH_2$—, $R_3$ is (3-OMe-4-OH)Ph, and X is S;

a compound of formula (Ia) wherein $R_1$ is H, $R_2$ is Ph, m is 1, L is —$CH_2$—, $R_3$ is (3-OMe-4-OH)Ph, and X is S;

a compound of formula (Ia) wherein $R_1$ is H, $R_2$ is H, m is 1, L is —$CH_2$—, $R_3$ is (3-OMe-4-OH)Ph, and X is S;

a compound of formula (Ia) wherein $R_1$ is 6-F, $R_2$ is H, m is 1, L is —$CH_2$—, $R_3$ is (3-OMe-4-OH)Ph, and X is S;

a compound of formula (Ia) wherein $R_1$ is H, $R_2$ is Cyclopropyl, m is 1, L is —$CH_2$—, $R_3$ is (3-OMe-4-OH)Ph, and X is S;

a compound of formula (Ia) wherein $R_1$ is H, $R_2$ is 3-thienyl, m is 1, L is —$CH_2$—, $R_3$ is (3-OMe-4-OH)Ph, and X is S;

a compound of formula (Ia) wherein $R_1$ is H, $R_2$ is 2-thienyl, m is 1, L is —$CH_2$—, $R_3$ is (3-OMe-4-OH)Ph, and X is S;

a compound of formula (Ia) wherein $R_1$ is H, $R_2$ is 3-furyl, m is 1, L is —$CH_2$—, $R_3$ is (3-OMe-4-OH)Ph, and X is S;

a compound of formula (Ia) wherein $R_1$ is H, $R_2$ is 2-furyl, m is 1, L is —$CH_2$—, $R_3$ is (3-OMe-4-OH)Ph, and X is S;

a compound of formula (Ia) wherein $R_1$ is H, $R_2$ is 4-pyridinyl, m is 1, L is —$CH_2$—, $R_3$ is (3-OMe-4-OH)Ph, and X is S;

a compound of formula (Ia) wherein $R_1$ is H, $R_2$ is 3-pyridinyl, m is 1, L is —$CH_2$—, $R_3$ is (3-OMe-4-OH)Ph, and X is S;

a compound of formula (Ia) wherein $R_1$ is H, $R_2$ is Ph, m is 1, L is —$CH_2CH_2$—, $R_3$ is (3-OMe-4-OH)Ph, and X is S;

a compound of formula (Ia) wherein $R_1$ is H, $R_2$ is Ph, m is 1, L is —$CH_2CH(Me)$-, $R_3$ is (3-OMe-4-OH)Ph, and X is S;

a compound of formula (Ia) wherein $R_1$ is H, $R_2$ is Ph, m is 1, L is —$CH(Me)CH_2$—, $R_3$ is (3-OMe-4-OH)Ph, and X is S;

a compound of formula (Ia) wherein $R_1$ is H, $R_2$ is Ph, m is 1, L is —$CH_2CH_2$—, $R_3$ is (3-OMe-4-$OCH_2CH_2NH_2$)Ph, and X is S;

a compound of formula (Ia) wherein $R_1$ is H, $R_2$ is Ph, m is 1, L is —$CH_2CH(Me)$-, $R_3$ is (3-OMe-4-$OCH_2CH_2NH_2$)Ph, and X is S;

a compound of formula (Ia) wherein $R_1$ is H, $R_2$ is Ph, m is 1, L is —$CH(Me)CH_2$—, $R_3$ is (3-OMe-4-$OCH_2CH_2NH_2$)Ph, and X is S;

a compound of formula (Ia) wherein $R_1$ is 6-OMe, $R_2$ is Ph, m is 1, L is —$CH_2$—, $R_3$ is 4-pyridinyl, and X is S;

a compound of formula (Ia) wherein $R_1$ is 6-F, $R_2$ is Ph, m is 1, L is —$CH_2$—, $R_3$ is 4-pyridinyl, and X is S;

a compound of formula (Ia) wherein $R_1$ is 6-Cl, $R_2$ is Ph, m is 1, L is —$CH_2$—, $R_3$ is 4-pyridinyl, and X is S;

a compound of formula (Ia) wherein $R_1$ is 6,7-diF, $R_2$ is Ph, m is 1, L is —$CH_2$—, $R_3$ is 4-pyridinyl, and X is S;

a compound of formula (Ia) wherein $R_1$ is 7-Cl, $R_2$ is Ph, m is 1, L is —$CH_2$—, $R_3$ is 4-pyridinyl, and X is S;

a compound of formula (Ia) wherein $R_1$ is 5-Cl, $R_2$ is Ph, m is 1, L is —$CH_2$—, $R_3$ is 4-pyridinyl, and X is S;

a compound of formula (Ia) wherein $R_1$ is 8-Cl, $R_2$ is Ph, m is 1, L is —$CH_2$—, $R_3$ is 4-pyridinyl, and X is S;

a compound of formula (Ia) wherein $R_1$ is 6-OMe, $R_2$ is (4-OMe)Ph, m is 1, L is —$CH_2$—, $R_3$ is 4-pyridinyl, and X is S;

a compound of formula (Ia) wherein $R_1$ is 6-OMe, $R_2$ is (3-OMe)Ph, m is 1, L is —$CH_2$—, $R_3$ is 4-pyridinyl, and X is S;

a compound of formula (Ia) wherein $R_1$ is 6-OMe, $R_2$ is (2-OMe)Ph, m is 1, L is —$CH_2$—, $R_3$ is 4-pyridinyl, and X is S;

a compound of formula (Ia) wherein $R_1$ is 6,7-diOMe, $R_2$ is —$CH_2$=$CH_2$, m is 1, L is —$CH_2$—, $R_3$ is 4-pyridinyl, and X is S;

a compound of formula (Ia) wherein $R_1$ is 6-F, $R_2$ is cyclopropyl, m is 1, L is —$CH_2$—, $R_3$ is 4-pyridinyl, and X is S;

a compound of formula (Ia) wherein $R_1$ is 6-t-Bu, $R_2$ is (4-t-Bu)Ph, m is 1, L is —$CH_2$—, $R_3$ is 4-pyridinyl, and X is S;

a compound of formula (Ia) wherein $R_1$ is 6-$CF_3$, $R_2$ is (4-$CF_3$)Ph, m is 1, L is —$CH_2$—, $R_3$ is 4-pyridinyl, and X is S;

a compound of formula (Ia) wherein $R_1$ is H, $R_2$ is Ph, m is 1, L is —$CH_2$—, $R_3$ is 3-pyridinyl, and X is S;

a compound of formula (Ia) wherein $R_1$ is 8-F, $R_2$ is Ph, m is 1, L is —$CH_2$—, $R_3$ is 2-pyridinyl, and X is S;

a compound of formula (Ia) wherein $R_1$ is H, $R_2$ is Ph, m is 1, L is —$CH_2CH_2$—, $R_3$ is 4-pyridinyl, and X is S;

a compound of formula (Ia) wherein $R_1$ is H, $R_2$ is Ph, m is 1, L is —$CH_2CH_2$—, $R_3$ is 3-pyridinyl, and X is S;

a compound of formula (Ia) wherein $R_1$ is H, $R_2$ is Ph, m is 1, L is —$CH_2CH_2$—, $R_3$ is 2-pyridinyl, and X is S;

a compound of formula (Ia) wherein $R_1$ is H, $R_2$ is Ph, m is 1, L is —$CH_2$—, $R_3$ is (2-OMe-3-OH)-5-thienyl, and X is S;

a compound of formula (Ia) wherein $R_1$ is 6,7-diF, $R_2$ is Ph, m is 1, L is a direct bond, $R_3$ is 5-isoquinolinyl, and X is O;

a compound of formula (Ia) wherein $R_1$ is 8-Cl, $R_2$ is Ph, m is 1, L is a direct bond, $R_3$ is 5-isoquinolinyl, and X is O;

a compound of formula (Ia) wherein $R_1$ is 6-OMe, $R_2$ is (2-OMe)Ph, m is 1, L is a direct bond, $R_3$ is 5-isoquinolinyl, and X is O;

a compound of formula (Ia) wherein $R_1$ is 6,7-diOMe, $R_2$ is —$CH_2$=$CH_2$, m is 1, L is a direct bond, $R_3$ is 5-isoquinolinyl, and X is O;

a compound of formula (Ia) wherein $R_1$ is 6-t-Bu, $R_2$ is (4-t-Bu)Ph, m is 1, L is a direct bond, $R_3$ is 5-isoquinolinyl, and X is O;

a compound of formula (Ia) wherein $R_1$ is 6-$CF_3$, $R_2$ is (4-$CF_3$)Ph, m is 1, L is a direct bond, $R_3$ is 5-isoquinolinyl, and X is O;

a compound of formula (Ia) wherein $R_1$ is 6-F, $R_2$ is (4-Cl)Ph, m is 1, L is a direct bond, $R_3$ is 5-isoquinolinyl, and X is O;

a compound of formula (Ia) wherein $R_1$ is 6-F, $R_2$ is (3-Cl)Ph, m is 1, L is a direct bond, $R_3$ is 5-isoquinolinyl, and X is O;

a compound of formula (Ia) wherein $R_1$ is 6-F, $R_2$ is (2-Cl)Ph, m is 1, L is a direct bond, $R_3$ is 5-isoquinolinyl, and X is O;

a compound of formula (Ia) wherein $R_1$ is H, $R_2$ is (4-$CF_3$)Ph, m is 1, L is a direct bond, $R_3$ is 5-isoquinolinyl, and X is O;

a compound of formula (Ia) wherein $R_1$ is H, $R_2$ is (3-$CF_3$)Ph, m is 1, L is a direct bond, $R_3$ is 5-isoquinolinyl, and X is O;

a compound of formula (Ia) wherein $R_1$ is H, $R_2$ is (2-$CF_3$)Ph, m is 1, L is a direct bond, $R_3$ is 5-isoquinolinyl, and X is O;

a compound of formula (Ia) wherein $R_1$ is H, $R_2$ is (3-OMe-4-OH)Ph, m is 1, L is a direct bond, $R_3$ is 5-isoquinolinyl, and X is O;

a compound of formula (Ia) wherein $R_1$ is H, $R_2$ is (3-OH-4-OMe)Ph, m is 1, L is a direct bond, $R_3$ is 5-isoquinolinyl, and X is O;

a compound of formula (Ia) wherein $R_1$ is 6-OMe-7-OH, $R_2$ is Ph, m is 1, L is a direct bond, $R_3$ is 5-isoquinolinyl, and X is O;

a compound of formula (Ia) wherein $R_1$ is 6-OH-7-OMe, $R_2$ is Ph, m is 1, L is a direct bond, $R_3$ is 5-isoquinolinyl, and X is O;

a compound of formula (Ia) wherein $R_1$ is 6-Me, $R_2$ is Ph, m is 1, L is a direct bond, $R_3$ is 5-isoquinolinyl, and X is O;

a compound of formula (Ia) wherein $R_1$ is 6-C($Me_2$)$CH_2$Me, $R_2$ is Ph, m is 1, L is a direct bond, $R_3$ is 5-isoquinolinyl, and X is O;

a compound of formula (Ia) wherein $R_1$ is 6-$NO_2$, $R_2$ is Ph, m is 1, L is a direct bond, $R_3$ is 5-isoquinolinyl, and X is O;

a compound of formula (Ia) wherein $R_1$ is 6-$OSO_3$Me, $R_2$ is Ph, m is 1, L is a direct bond, $R_3$ is 5-isoquinolinyl, and X is O;

a compound of formula (Ia) wherein $R_1$ is 6-$NHSO_2$Ph, $R_2$ is Ph, m is 1, L is a direct bond, $R_3$ is 5-isoquinolinyl, and X is O;

a compound of formula (Ia) wherein $R_1$ is 6-$CO_2$H, $R_2$ is Ph, m is 1, L is a direct bond, $R_3$ is 5-isoquinolinyl, and X is O;

a compound of formula (Ia) wherein $R_1$ is 6-C(O)$NH_2$, $R_2$ is Ph, m is 1, L is a direct bond, $R_3$ is 5-isoquinolinyl, and X is O;

a compound of formula (Ia) wherein $R_1$ is 6-C(O)$NMe_2$, $R_2$ is Ph, m is 1, L is a direct bond, $R_3$ is 5-isoquinolinyl, and X is O;

a compound of formula (Ia) wherein $R_1$ is 6-C(O)NHMe, $R_2$ is Ph, m is 1, L is a direct bond, $R_3$ is 5-isoquinolinyl, and X is O;

a compound of formula (Ia) wherein $R_1$ is 6-$CO_2$Ph, $R_2$ is Ph, m is 1, L is a direct bond, $R_3$ is 5-isoquinolinyl, and X is O;

a compound of formula (Ia) wherein $R_1$ is 6-cyclohexyl, $R_2$ is Ph, m is 1, L is a direct bond, $R_3$ is 5-isoquinolinyl, and X is O;

a compound of formula (Ia) wherein $R_1$ is 6-Ph, $R_2$ is Ph, m is 1, L is a direct bond, $R_3$ is 5-isoquinolinyl, and X is O;

a compound of formula (Ia) wherein $R_1$ is 6-NHC(O)($CH_2$)$_4$—CH=CH—CH(Me)$_2$, $R_2$ is Ph, m is 1, L is a direct bond, $R_3$ is 5-isoquinolinyl, and X is O;

a compound of formula (Ia) wherein $R_1$ is H, $R_2$ is 2-pyridinyl, m is 1, L is a direct bond, $R_3$ is 5-isoquinolinyl, and X is O;

a compound of formula (Ia) wherein $R_1$ is H, $R_2$ is 3-pyridinyl, m is 1, L is a direct bond, $R_3$ is 5-isoquinolinyl, and X is O;

a compound of formula (Ia) wherein $R_1$ is H, $R_2$ is 4-pyridinyl, m is 1, L is a direct bond, $R_3$ is 5-isoquinolinyl, and X is O;

a compound of formula (Ia) wherein $R_1$ is H, $R_2$ is 3-thienyl, m is 1, L is a direct bond, $R_3$ is 5-isoquinolinyl, and X is O;

a compound of formula (Ia) wherein $R_1$ is H, $R_2$ is 3-furyl, m is 1, L is a direct bond, $R_3$ is 5-isoquinolinyl, and X is O;

a compound of formula (Ia) wherein $R_1$ is H, $R_2$ is 2-furyl, m is 1, L is a direct bond, $R_3$ is 5-isoquinolinyl, and X is O;

a compound of formula (Ia) wherein $R_1$ is 6-F, $R_2$ is Ph, m is 1, L is a direct bond, $R_3$ is 3-hydroxynaphth-8-yl, and X is O;

a compound of formula (Ia) wherein $R_1$ is 6-F, $R_2$ is Ph, m is 1, L is a direct bond, $R_3$ is 1-hydroxynaphth-8-yl, and X is O;

a compound of formula (Ia) wherein $R_1$ is 6-F, $R_2$ is Ph, m is 1, L is a direct bond, $R_3$ is 4-hydroxynaphth-8-yl, and X is O;

a compound of formula (Ia) wherein $R_1$ is 6-F, $R_2$ is Ph, m is 1, L is a direct bond, $R_3$ is 5-hydroxynaphth-8-yl, and X is O;

a compound of formula (Ia) wherein $R_1$ is 6-F, $R_2$ is Ph, m is 1, L is a direct bond, $R_3$ is 3-chloro-2-hydroxynaphth-8-yl, and X is O;

a compound of formula (Ia) wherein $R_1$ is 6-F, $R_2$ is Ph, m is 1, L is a direct bond, $R_3$ is 2,3-dihydroxynaphth-8-yl, and X is O;

a compound of formula (Ia) wherein $R_1$ is 6-F, $R_2$ is Ph, m is 1, L is a direct bond, $R_3$ is 5-quinolinyl, and X is O;

a compound of formula (Ia) wherein $R_1$ is 6-F, $R_2$ is Ph, m is 1, L is a direct bond, $R_3$ is 5-cinnolinyl, and X is O;

a compound of formula (Ia) wherein $R_1$ is 6-F, $R_2$ is Ph, m is 1, L is a direct bond, $R_3$ is 3-Me-5-quinolinyl, and X is O;

a compound of formula (Ia) wherein $R_1$ is 6-F, $R_2$ is Ph, m is 1, L is a direct bond, $R_3$ is 4-(1,8-naphthyridinyl), and X is O;

a compound of formula (Ia) wherein $R_1$ is 6-F, $R_2$ is Ph, m is 1, L is a direct bond, $R_3$ is 5-quinazolinyl, and X is O;

a compound of formula (Ia) wherein $R_1$ is 6-F, $R_2$ is Ph, m is 1, L is a direct bond, $R_3$ is 2-OH-5-quinolinyl, and X is O;

a compound of formula (Ia) wherein $R_1$ is 6-F, $R_2$ is Ph, m is 1, L is a direct bond, $R_3$ is 3-OH-5-quinolinyl, and X is O;

a compound of formula (Ia) wherein $R_1$ is 6-F, $R_2$ is Ph, m is 1, L is a direct bond, $R_3$ is 3-F-5-quinolinyl, and X is O;

a compound of formula (Ia) wherein $R_1$ is 6-F, $R_2$ is Ph, m is 1, L is a direct bond, $R_3$ is 3-Cl-5-quinolinyl, and X is O;

a compound of formula (Ia) wherein $R_1$ is 6-F, $R_2$ is Ph, m is 1, L is a direct bond, $R_3$ is 2-OH-3-Cl-5-quinolinyl, and X is O;

a compound of formula (Ia) wherein $R_1$ is 6-F, $R_2$ is —$CH_2$=$CH_2$, m is 1, L is a direct bond, $R_3$ is 5-quinolinyl, and X is O;

a compound of formula (Ia) wherein $R_1$ is 6-F, $R_2$ is —$CH_2CH_3$, m is 1, L is a direct bond, $R_3$ is 5-quinolinyl, and X is O;

a compound of formula (Ia) wherein $R_1$ is 6-F, $R_2$ is Ph, m is 1, L is a direct bond, $R_3$ is 8-Cl-5-quinolinyl, and X is O;

a compound of formula (Ia) wherein $R_1$ is H, $R_2$ is 2-naphthyl, m is 1, L is a direct bond, $R_3$ is 5-isoquinolinyl, and X is O;

a compound of formula (Ia) wherein $R_1$ is 6-F, $R_2$ is Ph, m is 1, L is a direct bond, $R_3$ is 1,3-diMe-5-isoquinolinyl, and X is O;

a compound of formula (Ia) wherein $R_1$ is 6-F, $R_2$ is Ph, m is 1, L is a direct bond, $R_3$ is 8-Cl-5-isoquinolinyl, and X is O;

a compound of formula (Ia) wherein $R_1$ is 6-F, $R_2$ is Ph, m is 1, L is a direct bond, $R_3$ is 1,3-diMe-8-Cl-5-isoquinolinyl, and X is O;

a compound of formula (Ia) wherein $R_1$ is 6-F, $R_2$ is Ph, m is 1, L is —$CH_2$—, $R_3$ is 5-isoquinolinyl, and X is O;

a compound of formula (Ia) wherein $R_1$ is 6-F, $R_2$ is Ph, m is 1, L is a direct bond, $R_3$ is 3-quinolinyl, and X is O;

a compound of formula (Ia) wherein $R_1$ is 6-F, $R_2$ is Ph, m is 1, L is a direct bond, $R_3$ is 3-quinolinyl, and X is O;

a compound of formula (Ia) wherein $R_1$ is 6-F, $R_2$ is Ph, m is 1, L is a direct bond, $R_3$ is 3-quinolinyl, and X is O;

a compound of formula (Ia) wherein $R_1$ is 6-OH-7-OMe, $R_2$ is Ph, m is 1, L is a direct bond, $R_3$ is 3-quinolinyl, and X is O;

a compound of formula (Ia) wherein $R_1$ is 6,7-diOH, $R_2$ is Ph, m is 1, L is a direct bond, $R_3$ is 3-quinolinyl, and X is O;

a compound of formula (Ia) wherein $R_1$ is 6-OMe-7-OH, $R_2$ is Ph, m is 1, L is a direct bond, $R_3$ is 3-quinolinyl, and X is O;

a compound of formula (Ia) wherein $R_1$ is H, $R_2$ is Ph, m is 1, L is a direct bond, $R_3$ is 3-quinolinyl, and X is O;

a compound of formula (Ia) wherein $R_1$ is 6-F, $R_2$ is Ph, m is 1, L is a direct bond, $R_3$ is 1-Cl-5-isoquinolinyl, and X is O;

a compound of formula (Ia) wherein $R_1$ is 6-F, $R_2$ is Ph, m is 1, L is a direct bond, $R_3$ is 1-Me-5-isoquinolinyl, and X is O;

a compound of formula (Ia) wherein $R_1$ is 6-F, $R_2$ is Ph, m is 1, L is a direct bond, $R_3$ is 3-Me-5-isoquinolinyl, and X is O;

a compound of formula (Ia) wherein $R_1$ is 6-Br, $R_2$ is Ph, m is 1, L is a direct bond, $R_3$ is 8-isoquinolinyl, and X is O;

a compound of formula (Ia) wherein $R_1$ is 6-F, $R_2$ is 2-furyl, m is 1, L is a direct bond, $R_3$ is 5-isoquinolinyl, and X is O;

a compound of formula (Ia) wherein $R_1$ is 6-OMe, $R_2$ is Ph, m is 1, L is a direct bond, $R_3$ is 5-isoquinolinyl, and X is O;

a compound of formula (Ia) wherein $R_1$ is 6-F, $R_2$ is Ph, m is 1, L is a direct bond, $R_3$ is 4-Cl-5-isoquinolinyl, and X is O;

a compound of formula (Ia) wherein $R_1$ is 6-F, $R_2$ is Ph, m is 1, L is a direct bond, $R_3$ is 5-isoquinolinyl-N-oxide, and X is O;

a compound of formula (Ia) wherein $R_1$ is 6-Cl, $R_2$ is Ph, m is 1, L is a direct bond, $R_3$ is 5-isoquinolinyl, and X is O;

a compound of formula (Ia) wherein $R_1$ is 6-F, $R_2$ is 3-furanyl, m is 1, L is a direct bond, $R_3$ is 5-isoquinolinyl, and X is O;

a compound of formula (Ia) wherein $R_1$ is 6-$OCH_3$, $R_2$ is 3-thienyl, m is 1, L is a direct bond, $R_3$ is 5-isoquinolinyl, and X is O a compound of formula (Ia) wherein $R_1$ is 6-$OCH_3$, $R_2$ is 2,4 di-F Ph, m is 1, L is a direct bond, $R_3$ is 5-isoquinolinyl, and X is O;

a compound of formula (Ia) wherein $R_1$ is 6-$OCH_3$, $R_2$ is 2,4 di-F Ph, m is 1, L is a direct bond, $R_3$ is 5-isoquinolinyl, and X is O;

a compound of formula (Ia) wherein $R_1$ is 6-$OCH_3$, $R_2$ is Ph, m is 1, L is a direct bond, $R_3$ is 5-isoquinolinyl, and X is O;

a compound of formula (Ia) wherein $R_1$ is 6-F, $R_2$ is Ph, m is 1, L is a direct bond, $R_3$ is 5-isoquinolinyl, and X is O;

a compound of formula (Ia) wherein $R_1$ is 6-Cl, $R_2$ is Ph, m is 1, L is a direct bond, $R_3$ is 5-isoquinolinyl, and X is O;

a compound of formula (Ia) wherein $R_1$ is 6-F, $R_2$ is Ph, m is 1, L is a direct bond, $R_3$ is 5-isoquinolinyl-N-oxide, and X is O;

a compound of formula (Ia) wherein $R_1$ is 6-F, $R_2$ is Ph, m is 1, L is a direct bond, $R_3$ is 4-Cl-5-isoquinolinyl, and X is O;

a compound of formula (Ia) wherein $R_1$ is 6-F, $R_2$ is Ph, m is 1, L is a direct bond, $R_3$ is 4-Cl-5-isoquinolinyl, and X is O;

a compound of formula (Ia) wherein $R_1$ is 6-F, $R_2$ is Ph, m is 1, L is a direct bond, $R_3$ is 3-methyl-5-isoquinolinyl, and X is O;

a compound of formula (Ia) wherein $R_1$ is 6-F, $R_2$ is Ph, m is 1, L is a direct bond, $R_3$ is 1-methyl-5-isoquinolinyl, and X is O;

a compound of formula (Ia) wherein $R_1$ is 6-F, $R_2$ is Ph, m is 1, L is a direct bond, $R_3$ is 1-Cl-5-isoquinolinyl, and X is O;

a compound of formula (Ia) wherein $R_1$ is 6-Cl, $R_2$ is Ph, m is 1, L is a direct bond, $R_3$ is 5-isoquinolinyl-N-oxide, and X is O;

a compound of formula (Ia) wherein $R_1$ is 6-F, $R_2$ is 4-$CF_3$ Ph, m is 1, L is a direct bond, $R_3$ is 5-isoquinolinyl, and X is O;

a compound of formula (Ia) wherein $R_1$ is 6-F, $R_2$ is Ph, m is 1, L is a direct bond, $R_3$ is 1,3-diCl-5-isoquinolinyl, and X is O;

a compound of formula (Ia) wherein $R_1$ is 6-F, $R_2$ is Ph, m is 1, L is a direct bond, $R_3$ is 1,3-diCl-5-isoquinolinyl, and X is O;

a compound of formula (Ia) wherein $R_1$ is 6-F, $R_2$ is Ph, m is 1, L is a direct bond, $R_3$ is 8-Cl-5-isoquinolinyl, and X is O;

a compound of formula (Ia) wherein $R_1$ is 6-F, $R_2$ is Ph, m is 1, L is a direct bond, $R_3$ is 1-piperidinyl-5-isoquinolinyl, and X is O;

a compound of formula (Ia) wherein $R_1$ is 6-F, $R_2$ is Ph, m is 1, L is a direct bond, $R_3$ is 1-$OCH_3$-5-isoquinolinyl, and X is O;

a compound of formula (Ia) wherein $R_1$ is 6-F, $R_2$ is Ph, m is 1, L is a direct bond, $R_3$ is 1-F-5-isoquinolinyl, and X is O;

a compound of formula (Ia) wherein $R_1$ is 6-F, $R_2$ is Ph, m is 1, L is a direct bond, $R_3$ is 1-N,N-dimethyl-5-isoquinolinyl, and X is O;

a compound of formula (Ia) wherein $R_1$ is 6-Cl, $R_2$ is nil, m is nil, $R_3$ is 1—$CH_3$-5-isoquinolinyl, and X is O;

a compound of formula (Ia) wherein $R_1$ is 6-Cl, $R_2$ is nil, m is nil, $R_3$ is 1-Cl-5-isoquinolinyl, and X is O;

a compound of formula (Ia) wherein $R_1$ is 6-F, $R_2$ is 3-$CF_3$ Ph, m is 1, L is a direct bond, $R_3$ is 5-isoquinolinyl, and X is O;

a compound of formula (Ia) wherein $R_1$ is 6-F, $R_2$ is 3-$CF_3$ Ph, m is 1, L is a direct bond, $R_3$ is 5-isoquinolinyl-N-oxide, and X is O;

a compound of formula (Ia) wherein $R_1$ is 6-F, $R_2$ is 3-$CF_3$ Ph, m is 1, L is a direct bond, $R_3$ is 5-isoquinolinyl-N-oxide, and X is O;

a compound of formula (Ia) wherein $R_1$ is 6-F, $R_2$ is spiro-2-indanyl, L is a direct bond, $R_3$ is 5-isoquinolinyl, and X is O;

a compound of formula (Ia) wherein $R_1$ is 6-F, $R_2$ is 4-Cl, 3-$CF_3$ Ph, m is 1, L is a direct bond, $R_3$ is 5-isoquinolinyl, and X is O;and a compound of formula (Ia) wherein $R_1$ is 6-Cl, $R_2$ is Ph, m is 1, L is a direct bond, $R_3$ is 1—$CH_3$-5-isoquinolinyl, and X is O.

Preferred compounds of Formula (Ia) are selected from the group consisting of:

a compound of formula (Ia) wherein $R_1$ is 6-OMe, $R_2$ is Ph, m is 1, L is —$CH_2$—, $R_3$ is (3-OMe-4-OH)Ph, and X is S;

a compound of formula (Ia) wherein $R_1$ is H, $R_2$ is 3-Pyridinyl, m is 1, L is —$CH_2$—, $R_3$ is (3-OMe-4-OH)Ph, and X is S;

a compound of formula (Ia) wherein $R_1$ is 6-OMe, $R_2$ is Ph, m is 1, L is —$CH_2$—, $R_3$ is (3-OMe-4-OH)Ph, and X is O;

a compound of formula (Ia) wherein $R_1$ is H, $R_2$ is Ph, m is 1, L is —$CH_2$—, $R_3$ is (3-OMe-4-OH)Ph, and X is S;

a compound of formula (Ia) wherein $R_1$ is 6-F, $R_2$ is Ph, m is 1, L is —$CH_2$—, $R_3$ is (3,4-diOMe)Ph, and X is S;

a compound of formula (Ia) wherein $R_1$ is 6-OMe, $R_2$ is Ph, m is 1, L is a direct bond, $R_3$ is 5-isoquinolinyl, and X is O;

a compound of formula (Ia) wherein $R_1$ is 6-OMe, $R_2$ is Ph, m is 1, L is a direct bond, $R_3$ is 8-(2-naphtholyl), and X is O;

a compound of formula (Ia) wherein $R_1$ is H, $R_2$ is H, m is 0, L is a direct bond, $R_3$ is 5-isoquinolinyl, and X is O;

a compound of formula (Ia) wherein $R_1$ is 6-F, $R_2$ is H, m is 0, L is a direct bond, $R_3$ is 5-isoquinolinyl, and X is O;

a compound of formula (Ia) wherein $R_1$ is 6-F, $R_2$ is Ph, m is 1, L is a direct bond, $R_3$ is 5-isoquinolinyl, and X is O;

a compound of formula (Ia) wherein $R_1$ is 6-Br, $R_2$ is Ph, m is 1, L is a direct bond, $R_3$ is 5-isoquinolinyl, and X is O;

a compound of formula (Ia) wherein $R_1$ is 6,7-diOMe, $R_2$ is Ph, m is 1, L is a direct bond, $R_3$ is 5-isoquinolinyl, and X is O;

a compound of formula (Ia) wherein $R_1$ is 7-Cl, $R_2$ is Ph, m is 1, L is a direct bond, $R_3$ is 5-isoquinolinyl, and X is O;

a compound of formula (Ia) wherein $R_1$ is 5-Cl, $R_2$ is Ph, m is 1, L is a direct bond, $R_3$ is 5-isoquinolinyl, and X is O;

a compound of formula (Ia) wherein $R_1$ is H, $R_2$ is Ph, m is 1, L is a direct bond, $R_3$ is 5-isoquinolinyl, and X is O;

a compound of formula (Ia) wherein $R_1$ is 6-OMe, $R_2$ is (3-Cl)Ph, m is 1, L is a direct bond, $R_3$ is 5-isoquinolinyl, and X is O;

a compound of formula (Ia) wherein $R_1$ is 6,7-diOMe, $R_2$ is Ph, m is 1, L is a direct bond, $R_3$ is 5-isoquinolinyl, and X is O;

a compound of formula (Ia) wherein $R_1$ is 6-OMe, $R_2$ is (2-Cl)Ph, m is 1, L is a direct bond, $R_3$ is 5-isoquinolinyl, and X is O;

a compound of formula (Ia) wherein $R_1$ is 6-OMe, $R_2$ is (4-Cl)Ph, m is 1, L is a direct bond, $R_3$ is 5-isoquinolinyl, and X is O;

a compound of formula (Ia) wherein $R_1$ is 6-OMe, $R_2$ is H, m is 0, L is a direct bond, $R_3$ is 5-isoquinolinyl, and X is O;

a compound of formula (Ia) wherein $R_1$ is 6-OMe, $R_2$ is (2-$CF_3$)Ph, m is 1, L is a direct bond, $R_3$ is 5-isoquinolinyl, and X is O;

a compound of formula (Ia) wherein $R_1$ is 6-OMe, $R_2$ is (3-$CF_3$)Ph, m is 1, L is a direct bond, $R_3$ is 5-isoquinolinyl, and X is O;

a compound of formula (Ia) wherein $R_1$ is 6-OMe, $R_2$ is (4-$CF_3$)Ph, m is 1, L is a direct bond, $R_3$ is 5-isoquinolinyl, and X is O;

a compound of formula (Ia) wherein $R_1$ is H, $R_2$ is —CH=$CH_2$, m is 1, L is a direct bond, $R_3$ is 5-isoquinolinyl, and X is O;

a compound of formula (Ia) wherein $R_1$ is 6-Br, $R_2$ is H, m is 0, L is a direct bond, $R_3$ is 5-isoquinolinyl, and X is O;

a compound of formula (Ia) wherein $R_1$ is 6-Cl, $R_2$ is H, m is 0, L is a direct bond, $R_3$ is 5-isoquinolinyl, and X is O;

a compound of formula (Ia) wherein $R_1$ is 6-F, $R_2$ is Ph, m is 1, L is —$CH_2$—, $R_3$ is 5-isoquinolinyl, and X is O;

a compound of formula (Ia) wherein $R_1$ is 7-Cl, $R_2$ is H, m is 0, L is a direct bond, $R_3$ is 5-isoquinolinyl, and X is O;

a compound of formula (Ia) wherein $R_1$ is 8-Cl, $R_2$ is Ph, m is 1, L is a direct bond, $R_3$ is 5-isoquinolinyl, and X is O;

a compound of formula (Ia) wherein $R_1$ is 6-OMe, $R_2$ is (4-CN)Ph, m is 1, L is a direct bond, $R_3$ is 5-isoquinolinyl, and X is O;

a compound of formula (Ia) wherein $R_1$ is 6-OMe, $R_2$ is (4-Br)Ph, m is 1, L is a direct bond, $R_3$ is 5-isoquinolinyl, and X is O;

a compound of formula (Ia) wherein $R_1$ is 6,7-diF, $R_2$ is Ph, m is 1, L is a direct bond, $R_3$ is 5-isoquinolinyl, and X is O;

a compound of formula (Ia) wherein $R_1$ is 6-OMe, $R_2$ is —CH=$CH_2$, m is 1, L is a direct bond, $R_3$ is 5-isoquinolinyl, and X is O;

a compound of formula (Ia) wherein $R_1$ is 6-F, $R_2$ is —CH=$CH_2$, m is 1, L is a direct bond, $R_3$ is 5-isoquinolinyl, and X is O;

a compound of formula (Ia) wherein $R_1$ is 6-OMe, $R_2$ is (4-OMe)Ph, m is 1, L is a direct bond, $R_3$ is 5-isoquinolinyl, and X is O;

a compound of formula (Ia) wherein $R_1$ is 6-OMe, $R_2$ is (2-OMe)Ph, m is 1, L is a direct bond, $R_3$ is 5-isoquinolinyl, and X is O;

a compound of formula (Ia) wherein $R_1$ is 6-F, $R_2$ is 2-Thienyl, m is 1, L is a direct bond, $R_3$ is 5-isoquinolinyl, and X is O.

More preferred compounds of Formula (Ia) are selected from the group consisting of:

a compound of formula (Ia) wherein $R_1$ is 6-F, $R_2$ is Ph, m is 1, L is a direct bond, $R_3$ is 5-isoquinolinyl, and X is O;

a compound of formula (Ia) wherein $R_1$ is 6-Br, $R_2$ is Ph, m is 1, L is a direct bond, $R_3$ is 5-isoquinolinyl, and X is O;

a compound of formula (Ia) wherein $R_1$ is 5-Cl, $R_2$ is Ph, m is 1, L is a direct bond, $R_3$ is 5-isoquinolinyl, and X is O;

a compound of formula (Ia) wherein $R_1$ is H, $R_2$ is Ph, m is 1, L is a direct bond, $R_3$ is 5-isoquinolinyl, and X is O;

a compound of formula (Ia) wherein $R_1$ is 6-Br, $R_2$ is H, m is 0, L is a direct bond, $R_3$ is 5-isoquinolinyl, and X is O;

a compound of formula (Ia) wherein $R_1$ is 6-Cl, $R_2$ is H, m is 0, L is a direct bond, $R_3$ is 5-isoquinolinyl, and X is O;

a compound of formula (Ia) wherein $R_1$ is 6-F, $R_2$ is Ph, m is 1, L is —$CH_2$—, $R_3$ is 5-isoquinolinyl, and X is O;

a compound of formula (Ia) wherein $R_1$ is 7-Cl, $R_2$ is H, m is 0, L is a direct bond, $R_3$ is 5-isoquinolinyl, and X is O;

a compound of formula (Ia) wherein $R_1$ is 6,7-diF, $R_2$ is Ph, m is 1, L is a direct bond, $R_3$ is 5-isoquinolinyl, and X is O;

a compound of formula (Ia) wherein $R_1$ is 6-F, $R_2$ is —CH=$CH_2$, m is 1, L is a direct bond, $R_3$ is 5-isoquinolinyl, and X is O;

a compound of formula (Ia) wherein $R_1$ is 6-F, $R_2$ is 2-Thienyl, m is 1, L is a direct bond, $R_3$ is 5-isoquinolinyl, and X is O.

Still other more preferred compounds of Formula (Ia) are selected from the group consisting of:

a compound of formula (Ia) wherein $R_1$ is 6-OMe, $R_2$ is Ph, m is 1, L is —$CH_2$—, $R_3$ is (3-OMe-4-OH)Ph, and X is S;

a compound of formula (Ia) wherein $R_1$ is 6-OMe, $R_2$ is (3-Cl)Ph, m is 1, L is a direct bond, $R_3$ is 5-isoquinolinyl, and X is O;

a compound of formula (Ia) wherein $R_1$ is 6-OMe, $R_2$ is (2-Cl)Ph, m is 1, L is a direct bond, $R_3$ is 5-isoquinolinyl, and X is O;

a compound of formula (Ia) wherein $R_1$ is 6-OMe, $R_2$ is (2-$CF_3$)Ph, m is 1, L is a direct bond, $R_3$ is 5-isoquinolinyl, and X is O;

a compound of formula (Ia) wherein $R_1$ is 6-OMe, $R_2$ is (3-$CF_3$)Ph, m is 1, L is a direct bond, $R_3$ is 5-isoquinolinyl, and X is O;

a compound of formula (Ia) wherein $R_1$ is 6-OMe, $R_2$ is (4-$CF_3$)Ph, m is 1, L is a direct bond, $R_3$ is 5-isoquinolinyl, and X is O;

a compound of formula (Ia) wherein $R_1$ is 6-OMe, $R_2$ is (4-Br)Ph, m is 1, L is a direct bond, $R_3$ is 5-isoquinolinyl, and X is O;

a compound of formula (Ia) wherein $R_1$ is 6-OMe, $R_2$ is (4-OMe)Ph, m is 1, L is a direct bond, $R_3$ is 5-isoquinolinyl, and X is O;

The compounds of the present invention may also be present in the form of pharmaceutically acceptable salts. For use in medicine, the salts of the compounds of this invention refer to non-toxic "pharmaceutically acceptable salts" (Ref. *International J. Pharm.*, 1986, 33, 201-217; *J. Pharm. Sci.*, 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present in vention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

A therapeutically effective amount for use of the instant compounds or a pharmaceutical composition thereof comprises a dose range of from about 0.001 mg to about 1,000 mg, in particular from about 0.1 mg to about 500 mg or, more particularly from about 1 mg to about 250 mg of active ingredient per day for an average (70 kg) human.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as vanilloid receptor modulators is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

As modulators of the vanilloid VR1 ion channel, the compounds of Formula (I) are useful in methods for treating or preventing a disease or condition in a mammal which disease or condition is affected by the modulation of one or more vanilloid receptors. Such methods comprises administering to a mammal in need of such treatment or prevention a therapeutically effective amount of a compound, salt or solvate of Formula (I). In particular, the compounds of Formula (I) are useful for in methods for preventing or treating a chronic- or acute-pain causing diseases or conditions and pulmonary dysfunction, and more particualry, in treating diseases or conditions that cause inflammatory pain, burning pain, itch or urinary incontinence, and chronic obstructive pulmonary disease.

By way of example only, the compounds of Formula (I) are useful for treating diseases and conditions selected from the group consisting of osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, urinary tract infection, cough, asthma, chronic obstructive pulmonary disease, rhinitis, contact dermatitis/hypersensitivity, itch, eczema, anxiety, panic disorders, pharyngitis, mucositis, enteritis, cellulites, peripheral neuropathy, bilateral peripheral neuropathy, diabetic neuropathy, postherpetic neuralgia, trigeminal neuralgia, causalgia, sciatic neuritis, mandibular joint neuralgia, peripheral neuritis, polyneuritis, stump pain, phantom limb pain, bony fractures, post-operative ileus, irritable bowel syndrome, inflammatory bowel diseases such as Crohn's Disease and ulcerative colitis, cholecystitis, pancreatitis, postmastectomy pain syndrome, oral neuropathic pain, Charcot's pain, reflex sympathetic dystrophy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, sinus headache, tension headache, labor, childbirth, intestinal gas, menstruation, cancer, and trauma.

While the present invention comprises compositions comprising one or more of the compounds of Formula (I), the present invention also comprises compositions comprising intermediates used in the manufacture of compounds of Formula (I).

General Synthetic Methods

Representative compounds of the present invention can be synthesized in accordance with the general synthetic methods described below and are illustrated in the schemes that follows. Since the schemes are an illustration, the invention should not be construed as being limited by the chemical reactions and conditions expressed. The preparation of the various starting materials used in the schemes is well within the skill of persons versed in the art.

The ureas of formula (I) that comprise this invention are synthesized using several distinct chemical methods. The general transformations for constructing β-aminotetralin-derived ureas involve:

Preparation of suitably substituted β-aminotetralin, which is described in the general schemes below. Tetralone starting materials were either purchased from commercial sources or were prepared using the method reported by Sims (Sims, J. J. et. al. *Tetrahedron Lett.* 1971, 951). Specifically, substituted phenylacetic acids were separately reacted with ethylene gas and a Lewis Acid such as aluminum trichloride to afford the desired corresponding β-tetralone.

An appropriately substituted β-tetralone (II) is reacted with an aryl or heteroaryl aldehyde in the presence of a base such as piperidine, in an inert halohydrocarbon, ethereal or hydrocarbon solvent, such as benzene, from ambient temperature to reflux, to afford the corresponding α-benzylidenyl-β-tetralone or α-heteroarylmethylidenyl-β-tetralone (III). The β-tetralone (III) is dissolved in an inert hydrocarbon, ethereal, ester or alcohol solvent, such as methanol, and reacted with hydrogen gas at a pressure from ambient pressure to 100 p.s.i. in the presence of a suitable catalyst such as palladium on carbon. The reaction is performed at a temperature from ambient temperature to reflux, to yield the desired α-substituted-β-tetralone (IV) (Scheme 1).

An alternative method for the preparation of α-substituted-β-tetralones (IV) involves the reaction of an appropriately substituted β-tetralone (II) with a base such as pyrrolidine in an inert halohydrocarbon solvent such as dichloromethane or hydrocarbon solvent such as benzene, under Dean-Stark conditions (removal of water) or in an alcohol solvent such as methanol, from ambient temperature to reflux, to afford enamine (V). Alkylation of enamine (V) is accomplished by reaction with a benzylic, heterocyclicalkanyl or an allylic halide in an inert solvent such as acetonitrile, at a temperature from ambient temperature to reflux, to afford the α-substituted-β-iminium salt (VI). Hydrolysis of the salt (VI) to produce the desired α-substituted-β-tetralone product (IV) is accomplished by reaction of (VI) with water and an inorganic or organic acid such as hydrochloric or glacial acetic acid in an inert hydrocarbon, ethereal, alcohol or halohydrocarbon solvent, or a mixture thereof, such as methanol and dichloromethane (Scheme 1).

an inorganic acid, such as trifluoroacetic acid or hydrochloric acid, for example (Scheme 2).

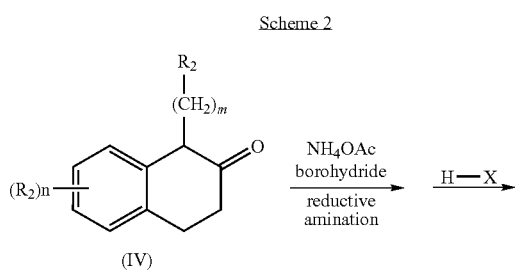

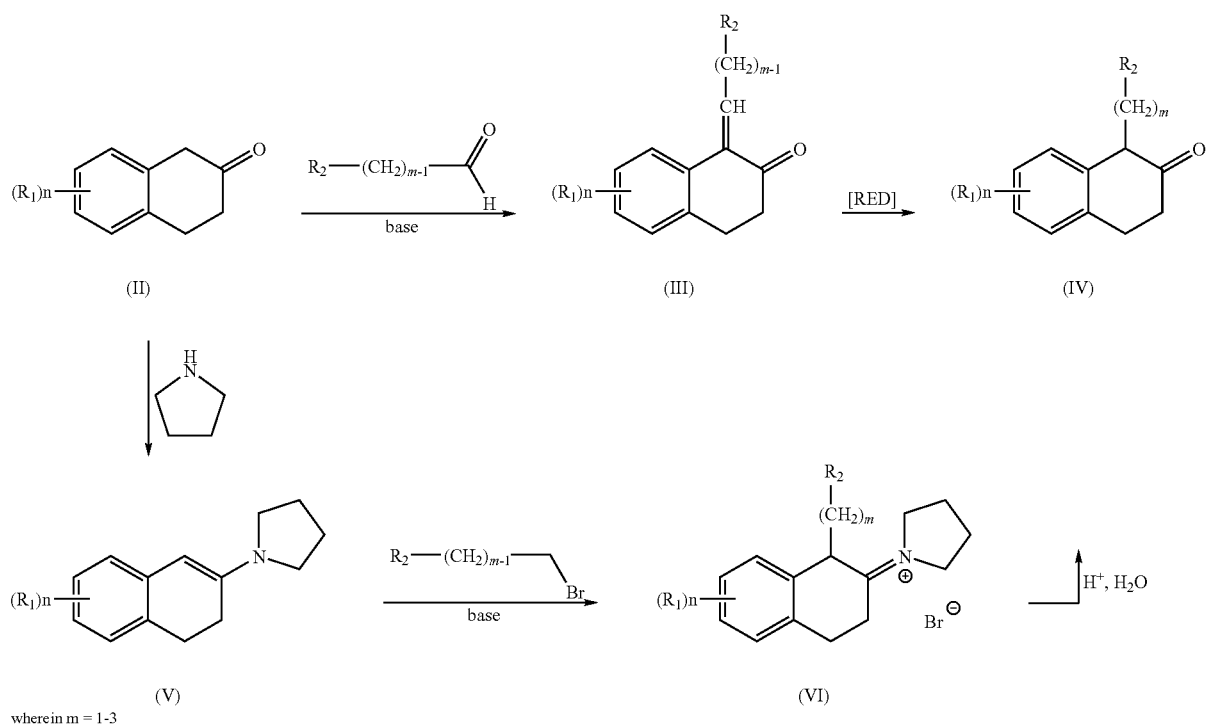

wherein m = 1-3

The α-substituted-β-tetralones (IV) are converted to the corresponding aminotetralins via reaction with an ammonium salt such as ammonium acetate in the presence of a reducing agent such as sodium cyanoborohydride, for example, in an inert halohydrocarbon, hydrocarbon, ethereal or alcohol solvent such as methanol to produce the cis-aminotetralin (VII). In some cases, the trans-aminotetralin (VIII) is also formed as a minor product; both sets of diastereomers are part of this invention. The aminotetralins (VII) can also be isolated as acid addition salts by treatment with an organic or

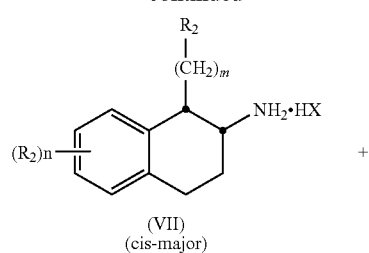

-continued

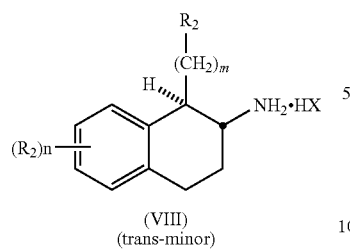

(VIII)
(trans-minor)

wherein HX is the acid

Compounds in which m=0 are prepared from an appropriately substituted aminotetralin (VII; m=0) starting from 1-tetralones using the synthetic sequence shown in Scheme 2a.

Scheme 2a

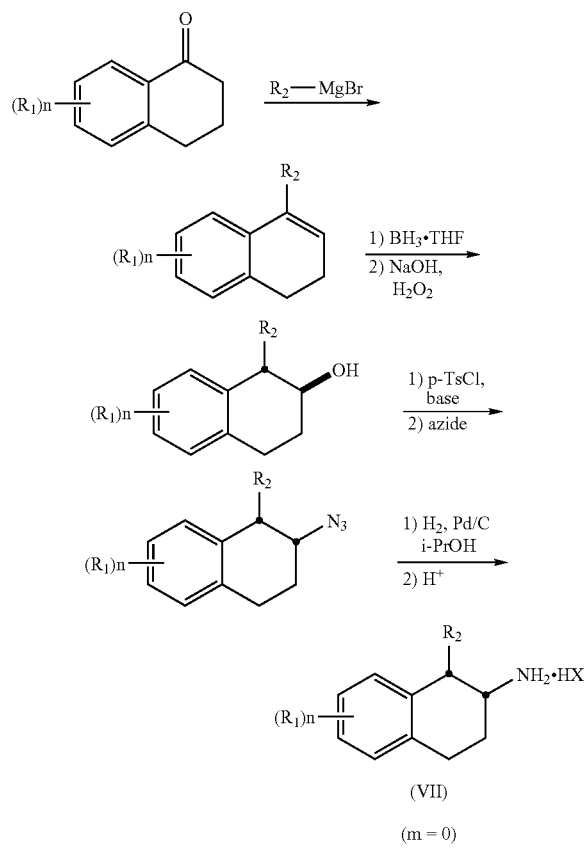

(VII)
(m = 0)

Aminotetralin (VII) can be used in subsequent reactions as the corresponding free base or as an acid addition salt. The use of acid addition salts requires an additive, such as an organic base like triethylamine or an inorganic base such as hydroxide, to neutralize the acid and liberate the reactive nucleophilic amine center. This common practice is well known to those skilled in the art.

Aminotetralin VII is reacted with isocyanate or isothiocyanate, in an appropriate inert solvent, with or without an added base, to form ureas (IX) or thioureas (X), shown in Scheme 3.

Scheme 3

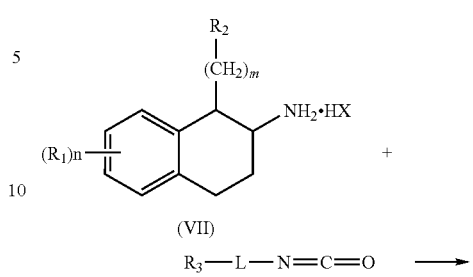

In addition to isocyanates and isothiocyanates, other carbamylating or thiocarbamylating agents may be used and this is well known to those skilled in the art. Thus an appropriate amine, such as an aminoisoquinoline, aminonaphthol or aminoquinoline, is reacted with a chloroformate, such as phenyl chloroformate in an inert solvent, with or without added base, to afford the corresponding phenylcarbamates. Separately these carbamates are reacted with aminotetralin (VII) in a polar solvent such as dimethylsulfoxide, with or without added base, from room temperature to approximately 150 C, to produce the aminotetralin-derived ureas (IX) (Scheme 4).

Scheme 4

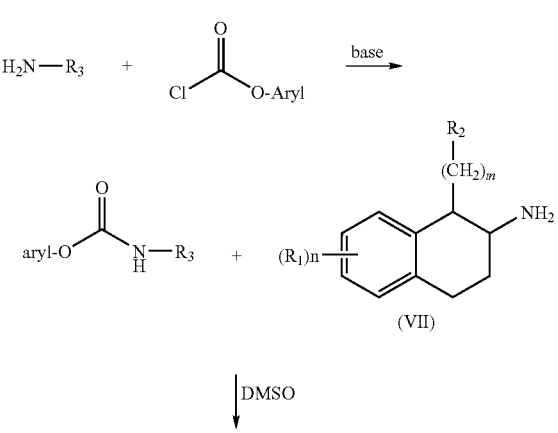

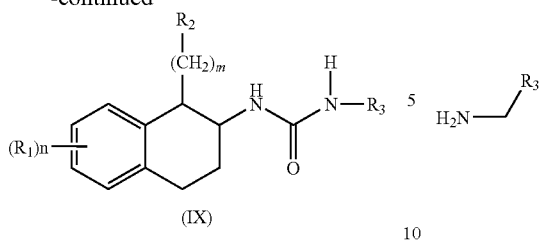

(IX)

The use of chlorothionoformates in the scheme above produces the analogous aminotetralin-derived thioureas (X).

Isocyanates and isothiocyanates are also prepared by reacting an amine with phosgene or thiophosgene in the presence of a base. Benzylamines such as 4-alkanyloxy-3-methoxy-benzylamine is reacted with thiophosgene or a thiophosgene equivalent, in the presence of a base, such as an organic amine, to produce the corresponding thiocyanate. Subsequent reaction with aminotetralin (VII) produces the corresponding aminotetralin-derived homovanillic thioureas (Scheme 5). Protecting group manipulations may be used to mask and subsequently liberate the phenolic OH group and this practice is well known to those skilled in the art.

Scheme 5

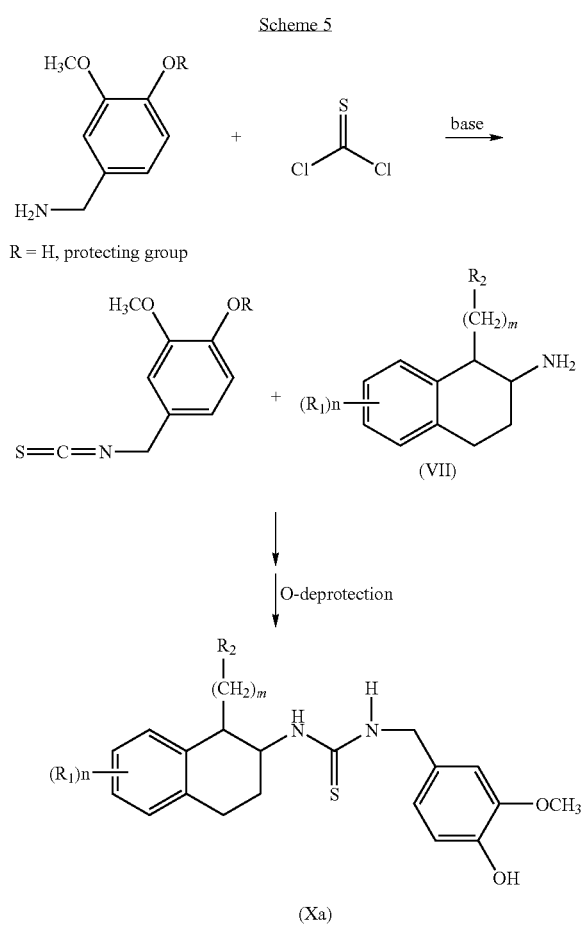

(Xa)

The use of (heteroaryl)alkanylamines, such as pyridylmethylamine, produces the corresponding aminotetralin-derived ureas in which $R_3$=heteroaryl (Scheme 6). Thiocarbamylation with aminotetralin, as described above, gives the analogous thioureas.

Scheme 6

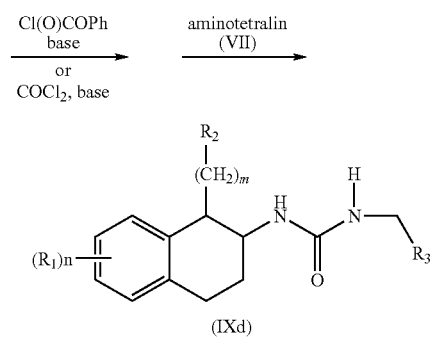

(IXd)

Aminotetralin-derived ureas and thioureas with linking groups (L) of varying length are produced via homologation of aryl- or heteroaryl-carboxaldehydes or carboxylic acids. This practice is well known in the literature and encompasses a wide variety of chemical transformations, several of which are described below to illustrate the strategy but are not intended to be inclusive.

Isoquinoline is reacted with N-(hydroxymethyl)trifluoro-acetamide in acid followed by reduction to afford isoquinolin-5-yl-methylamine. Carbamylation using aminotetralin as described above, produces aminotetralin-derived ureas in which L=$CH_2$ (methylene) (Scheme 7).

Scheme 7

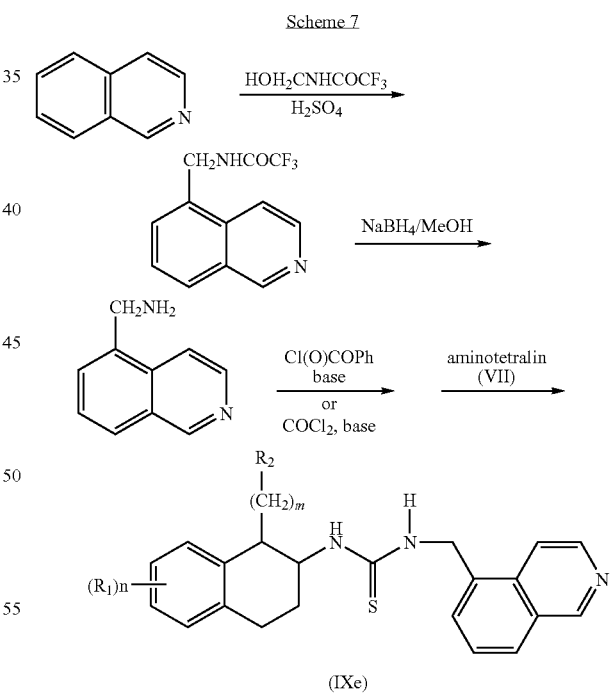

(IXe)

Aminonaphthalene is subjected to a Sandmeyer reaction, namely diazotization followed by reaction with copper cyanide at high temperature to produce the cyanonaphthalene. Reduction affords naphthalen-2-yl-methylamine which is subjected to carbamylation using aminotetralin (VII), as described above, to produce aminotetralin-derived urea in which L=$CH_2$ (methylene) (Scheme 8).

Scheme 8

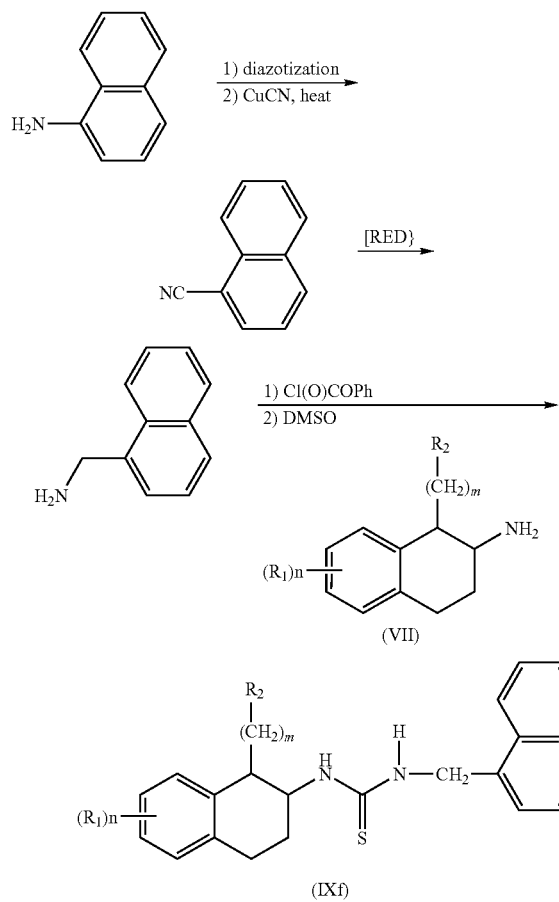

Reaction of aryl- and heteroaryl-carboxaldehydes with toluenesulfonyl methylisocyanide in the presence of base, with subsequent hydrolysis affords the corresponding homologated nitrile. Reduction produces the homologated amine which is subjected to carbamylation with aminotetralin as described above to yield aminotetralin-derived ureas in which L=$CH_2CH_2$ (Scheme 9).

Scheme 9

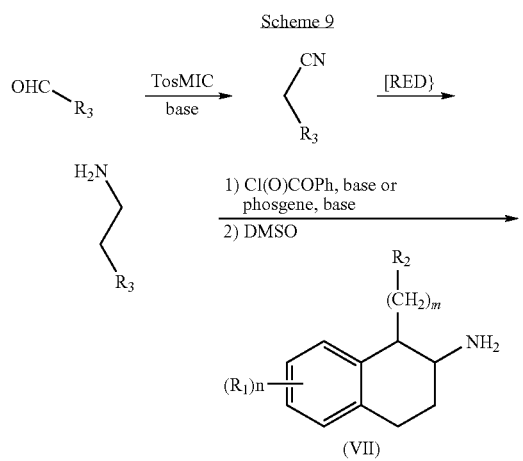

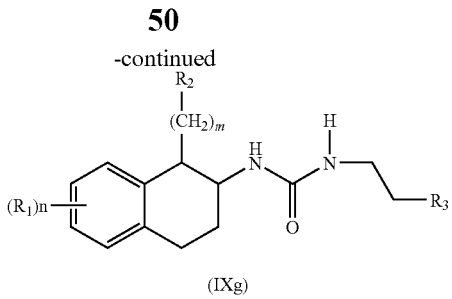

Heteroaryl- and aryl-carboxaldehydes are modified using Wittig conditions to give the α,β-unsaturated nitrile which is reduced to the amine and subsequent carbamylated as described above to yield aminotetralin-derived ureas in which L=$CH_2CH_2CH_2$ (Scheme 10).

Scheme 10

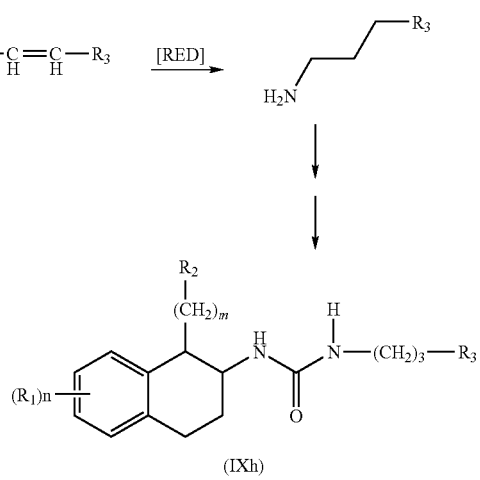

Homologation of heteroaryl- and aryl-carboxylic acids is also accomplished using chemistry known as the Arndt-Eistert synthesis, a procedure that converts carboxylic acids to the next higher homolog using a three step synthesis. In the first transformation, the carboxylic acid starting material is converted to its acyl chloride, using thionyl chloride, oxalyl chloride or another appropriate chlorinating agent. In the second step, the acyl chloride is converted to a diazoketone via reaction with diazomethane or a suitable equivalent. In the final transformation, the diazoketone is oxidized to the homologous acid using an oxidant such as silver oxide. The carboxylic acid group is then converted to an isocyanate through the intermediacy of the acyl azide (Curtius rearrangement) which is carried on to aminotetralin-derived ureas and thioureas using the chemistry described above. Alternatively, the carboxylic acid is reacted with hydrazoic acid (or equivalent) under acid catalysis followed by thermal decomposition to the amine (Schmidt reaction), which is carried on to aminotetralin-derived ureas and thioureas using the chemistry described above.

This chemistry and related variations are well known to those skilled in the art.

Protecting group manipulations may be needed at various stages of the syntheses depending upon substituents and functional groups that are present on the reactants.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and cyclohexane are typical hydrocarbon solvents and dichloromethane and dichloroethane are representative halogenhydrocarbon solvents. In those cases wherein the product is isolated as the acid addition salt the free base may be obtained by techniques known to those skilled in the art. In those cases in which the product is isolated as an acid addition salt, the salt may contain one or more equivalents of the acid.

Representative compounds of the present invention can be synthesized in accordance with the general synthetic methods described above and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

EXAMPLE 1

1-(1-Benzyl-6-methoxy-1,2,3,4-tetrahydronaphthalene-2-yl)-3-isoquinolin-5-yl-urea Compound 33

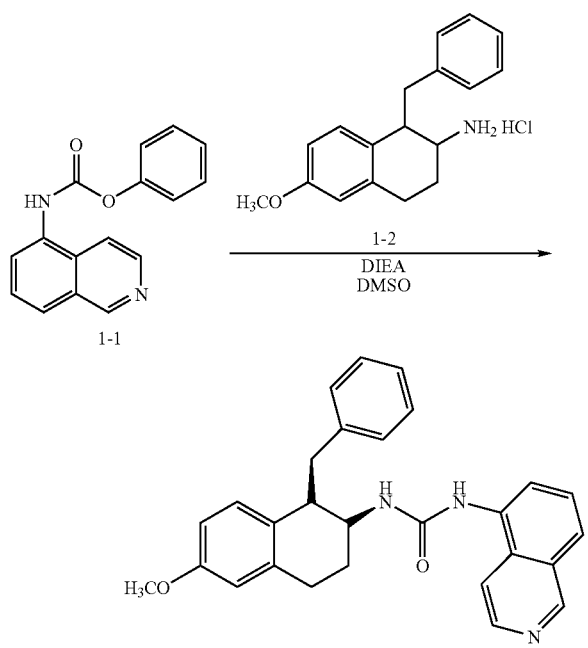

Isoquinolin-5-yl-carbamic acid phenyl ester 1-1 (0.004 mole, 1.06 g) was dissolved in 15 mL of dimethylsulfoxide. Diisopropylethyl amine (0.0044 mole, 0.57 g, 0.8 mL) was added followed by addition of 1-benzyl-6-methoxy-1,2,3,4-tetrahydro-naphthalen-2-ylamine hydrochloride 1-2 (0.0044 mole, 1.33 g). The reaction mixture was stirred at room temperature for 16 hours. The reaction mixture was then poured into 50 mL of water containing 10 mL of 1N sodium hydroxide. The precipitated solid was collected by filtration. This solid was chromatographed on silica gel eluting with methylene chloride, 3% methanol. Subsequently the product was further purified by recrystallization from ethyl acetate. The title compound 33 (1-(1-benzyl-6-methoxy-1,2,3,4-tetrahydro-naphthalen-2-yl)-3-isoquinolin-5-yl-urea) was obtained as an off-white solid (1.05 g, 0.0024 mole). MS (MH+): 438; $^1$H NMR (CDCl$_3$): δ 1.7-1.8 (m, 2H), 2.6-2.9 (m, 4H), 3.6 (s, 3H), 4.1 (m, 1H), 5.8 (d, 1H), 6.4-6.4 (m, 3H), 6.95 (d, 2H), 7.1 (m, 3H), 7.3 (t, 1H), 7.4-7.5 (m, 2H), 8.2 (d, 2H), 9.0 (s, 1H).

EXAMPLE 2

1-(1-Benzyl-6-fluoro-1,2,3,4-tetrahydronaphthalene-2-yl)-3-isoquinolin-5-yl-urea Compound 38

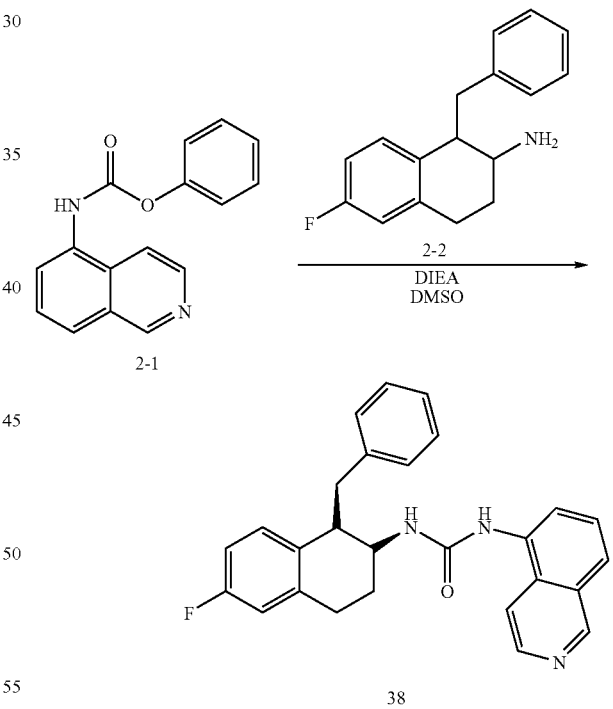

Isoquinolin-5-yl-carbamic acid phenyl ester 2-1 (0.005 mole, 1.32 g) was dissolved in 15 mL of DMSO (dimethylsulfoxide) followed by the addition of the aminotetralin 2-2, 1-benzyl-6-fluoro-1,2,3,4-tetrahydro-naphthalen-2-ylamine (0.0044 mole, 1.12 g). The reaction mixture was then stirred at room temperature for 16 hours. The reaction mixture was poured into 50 mL of water containing 10 mL of 1N NaOH (sodium hydroxide). The precipitated solid was collected by filtration. This solid was chromatographed on silica gel eluting with methylene chloride, 3% methanol. Subsequently the product was further purified by recrystallization from ethyl acetate. The title compound 38, (1-(1-benzyl-6-fluoro-1,2,3,4-tetrahydro-naphthalen-2-yl)-3-isoquinolin-5-yl-urea) was obtained as an off-white solid (1.25 g, 0.00295 mole). MS (MH+): 426; $^1$H NMR (MeOH): δ 1.35 (m, 1H), 1.9 (m, 1H), 2.1-2.2 (m, 1H), 2.9-3.1 (m, 4H) 3.45 (m, 1H), 4.1-4.2 (m, 1H), 6.7 (t, 1H), 6.8-6.9 (m, 2H), 7.1-7.3 (m, 5H), 7.85 (t, 1H), 8.1 (d, 1H), 8.25 (d, 1H), 8.35 (d, 1H), 8.6 (d, 1H).

EXAMPLE 3

1-(1-cyclopropylmethyl-6-fluoro-1,2,3,4-tetrahydronaphthalen-2-yl)-3-isoquinolin-5-yl-urea Compound 71

1-Cyclopropylmethyl-6-fluoro-1,2,3,4-tetrahydro-naphthalen-2-ylamine hydrochloride (127 mg, 0.49 mmol), isoquinolin-5-yl-carbamic acid phenyl ester (150 mg, 0.49 mmol), and diisopropylethylamine (193 mg, 1.47 mmol) were combined and stirred at ambient temperature in DMSO (3 mL) overnight. The product was purified by directly injecting the crude reaction onto a reverse phase prep-HPLC (10-90% water:acetonitrile gradient). The appropriate fractions were lyophilized to yield 1-(1-cyclopropylmethyl-6-fluoro-1,2,3,4-tetrahydro-naphthalen-2-yl)-3-isoquinolin-5-yl-urea 71 (68 mg, 0.14 mmol). MS (MH$^+$) 390; $^1$H NMR (CD$_3$OD) δ 0.08-0.87 (m, 2H), 1.60-1.65 (m, 2H), 2.03 (m, 1H), 2.97 (m, 2H), 3.14 (m, 1H), 4.36 (m, 1H), 6.87 (m, 2H), 7.27 (m, 1H), 7.93 (t, 1H, J=2.6 Hz), 8.14 (d, 1H, J=2.7 Hz), 8.32 (d, 1H, J=2.2 Hz), 8.47 (d, 1H, J=2.6 Hz), 8.53 (d, 1H, J=2.2 Hz), 9.63 (s, 1H). HPLC R$_t$=3.63 min (10-90% water:acetonitrile gradient, 100% pure).

EXAMPLE 4

1-(1-Benzyl-6-fluoro-1,2,3,4-tetrahydronaphthalene-2-yl)-3-isoquinolin-5-ylmethyl-urea Compound 60

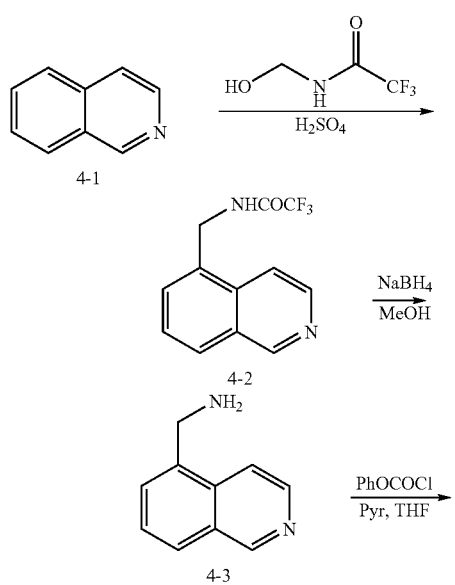

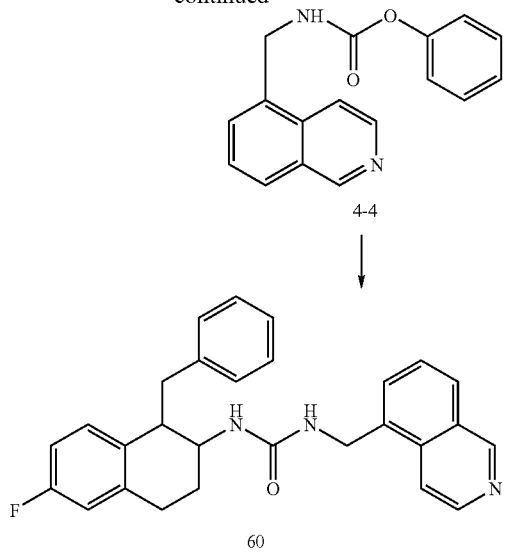

Isoquinoline 4-1 (0.01 mole, 1.29 g) was dissolved in 50 mL of concentrated H$_2$SO$_4$ (sulfuric acid) which had been cooled to 0° C. in an ice-water bath. The N-hydroxymethyl trifluoroacetamide was then added in portions. The reaction mixture was stirred at 0° C. for 15 minutes and then allowed to warm to room temperature and stirred for 16 hours. The clear light brown reaction mixture was poured onto 200 g of ice then NH$_4$OH (ammonium hydroxide) was added until the reaction mixture was basic to pH paper. The aqueous mixture was extracted with 100 mL of CH$_2$Cl$_2$ (methylene chloride). The organic layer was separated and washed with 2×100 mL of brine, dried over Na$_2$SO$_4$ (sodium sulfate) and evaporated in vacuo. The residue was chromatographed on silica gel eluting with 60/40 hexane/ethyl acetate to yield the trifluoroacetamide 4-2 product as a white crystalline solid (0.008 mole, 2.03g). MS (MH+): 255; $^1$H NMR (CDCl$_3$): δ 5.0 (s, 2H), 7.6 (t, 1H), 7.8 (d, 1H), 7.95 (d, 1H), 8.1 (d, 1H), 8.5 (d, 1H), 9.2 (s, 1H).

The trifluoroacetamide 4-2 from step A (0.006 mole, 1.53 g) was dissolved in 50 mL of methanol. Sodium borohydride (0.02 mole, 0.8 g) was then added and the reaction mixture was stirred at room temperature for 2 hours. Thin layer chromatography (silica gel, 50/50 hexane/ethyl acetate) showed the reaction to be nearly complete. An additional amount of sodium borohydride was added (0.01 mole, 0.4 g) and stirring was continued for another 1 hour. The reaction mixture was evaporated in vacuo. The residue was taken up in 50 mL of CH$_2$Cl$_2$ and then washed with 2×50 mL of brine, dried over Na$_2$SO$_4$ and evaporated in vacuo to yield the amine product 4-3 as a clear oil (0.005 mole, 0.79 g). MS (MH+): 159; $^1$H NMR (CDCl$_3$): δ 4.3 (s, 2H), 7.5 (t, 1H), 7.7 (d, 1H), 7.8 (d, 1H), 7.9 (d, 1H), 8.5 (d, 1H), 9.2 (s, 1H).

The amine 4-3 from step B (0.005 mole, 0.79 g) was dissolved in 20 mL of tetrahydrofuran (THF). Pyridine (0.0055 mole, 0.44g, 0.44 mL) was added followed by the careful addition of phenylchloroformate (0.0055 mole, 0.86 g, 0.69 mL). The reaction mixture immediately turned yellow and turbid. Stirring at room temperature was continued for 2 hours. The reaction mixture was evaporated in vacuo. The residue was taken up in 50 mL of dichloromethane, washed with 2×100 mL saturated sodium bicarbonate then 2×100mL of water. The organic layer was dried over sodium sulfate and evaporated in vacuo to give a thick slightly yellow oil. This oil was triturated with diethylether and then treated with 1M HCl/diethylether to give the carbamate hydrochloride product 4-4 as an off-white solid. MS (MH+): 279; $^1$H NMR (MeOH): δ 4.6 (s, 2H), 6.8 (m, 1H), 7.1-7.4 (m, 4H), 7.9 (t, 2H), 8.1 (d, 1H), 8.5 (d, 1H), 8.8 (d, 1H), 9.8 (s, 1H).

The carbamate hydrochloride 4-4 from step C (0.0005 mole, 0.139 g) was dissolved in 2 mL of dimethylsulfoxide. Diisopropylethyl amine (0.0011 mole, 0.142 g, 0.19 mL) was added followed by addition of 1-benzyl-6-methoxy-1,2,3,4-tetrahydro-naphthalen-2-ylamine hydrochloride (0.00055 mole, 0.297 g). The reaction mixture was stirred at room temperature for 4 hours. The reaction mixture was then poured into 20 mL of water containing 5 mL of 1N sodium hydroxide and stirred at room temperature for 15 minutes. The precipitated solid was collected by filtration. This cream colored powder was recrystallized from ethyl acetate/hexane to afford the title product 60, 1-(1-benzyl-fluoro-1,2,3,4-tetrahydro-naphthalen-2-yl)-3-isoquinolin-5-yl-methyl urea as a white chalky powder (0.000015 mole, 0.065 g). MS (MH+): 440; $^1$H NMR (CDCl$_3$): δ 1.8-2.0 (m, 2H), 2.8-3.0 (m, 4H), 4.1 (m 1H), 4.35 (d, 1H), 4.5 (m, 1H), 4.8 (d, 2H), 6.6-6.8 (m, 4H), 7.1-7.3 (m, 4H), 7.5 (t, 1H), 7.6 (d, 1H), 7.8 (d 1H), 7.9 (d, 1H), 8.6 (d, 1H), 9.2 (s, 1H).

EXAMPLE 5

1-(1-Benzyl-6-fluoro-1,2,3,4-tetrahydronaphthalene-2-yl)-3-(7-hydroxy-naphthalen-1-yl)-urea Compound 67

8-Amino-naphthalen-2-ol (74 mg, 0.46 mmol) was added to a solution of 1-benzyl-2-isocyanato-6-methoxy-1,2,3,4-tetrahydro-naphthalene (136 mg, 0.46 mmol) in acetonitrile (2 mL). The reaction was microwaved for 5 min at 100° C. The solvent was stripped off and the residue chromatographed on a silica column using chloroform as eluant to yield title compound 68 (95 mg, 45%) MS (MH$^+$) 453; $^1$H NMR (CD$_3$OD) δ 1.87 (m, 1H), 2.02 (m, 1H), 2.89-2.93 (m, 4H), 3.38 (m, 1H), 3.73 (s, 3H), 4.05 (m, 1H), 6.52 (d, 1H, J=3 Hz), 6.65 (m, 2H), 7.09 (d, 3H, J=2.4 Hz), 7.14 (d, 1H, J=2.2 Hz), 7.21 (d, 2H, J=2.3 Hz), 7.26 (d, 2H, J=3.0 Hz), 7.52-7.58 (m, 2H), 7.72 (d, 1H, J=2.9 Hz). HPLC R$_t$=4.73 min (10-90% water:acetonitrile gradient, 100% pure).

EXAMPLE 6

1-(1-Benzyl-6-methoxy-1,2,3,4-tetrahydro-naphthalen-2-yl)-3-(4-hydroxy-3-methoxy-benzyl)-thiourea Compound 3

Sodium hydride (60% in oil, 2.81 g, 10 mmol) was added to a solution of 4-hydroxy-3-methoxy-benzonitrile (10 g, 67 mmol) in DMF (100 mL) at 0° C. Mixture was allowed to stir at ambient temperature for 30 min. Bromomethylmethyl ether (6.4 mL, 70 mmol) was added to the resultant solution, and the solution was stirred at rt for 2 h. The solution was poured into ice water (~400 mL). The product, 3-Methoxy-4-methoxymethoxy-benzonitrile, was collected by filtration, washed generously with water, and allowed to air dry to give the product as a colorless solid 11.75 g (91%). The purity of the product was estimated to be (95% by HPLC and H NMR, and the product was used without further purification in the subsequent step). $^1$H NMR (CDCl$_3$): δ 3.51 (s, 3H), 3.91 (s, 3H), 5.23 (s, 2H), 7.12 (d, J=1.8 Hz, 1H), 7.20 (d, J=8.4 Hz, 1H) and 7.25 (d of d, J=8.4 & 1.8 Hz, 1H).

A solution of 3-methoxy-4-methoxymethoxy-benzonitrile (9.1 g, 47.1 mmol) in THF (75 mL) was slowly added, via an addition funnel, to a solution of LAH in THF (1.0 M, 100 mL, 100 mmol) cooled on an ice bath. The resultant solution was heated to reflux for 4 h. The solution was cooled on an ice bath. Sequential addition of water (3.5 mL), 15% aqueous sodium hydroxide (7 mL) and water (10 mL) was carefully done via an addition funnel. The inorganics were removed by filtration, and washed generously with THF. The combined organic solutions were dried over sodium sulfate, and the solvent was evaporated under vacuum to give the product, 5.3 g (57%). The product was used without purification in the subsequent step. $^1$H NMR (CDCl$_3$): δ 1.58 (br s, 1H), 3.51 (s, 3H), 3.82 (s, 2H), 3.89 (s, 3H), 5.21 (s, 2H), 6.82 (d of d, J=8.4 & 1.8 Hz, 1H), 6.90 (d, J=1.8 Hz) and 7.10 (d, J=8.1 Hz, 1H). MS: m/z 198 (M+H)$^+$.

A solution of 3-methoxy-4-methoxymethoxybenzylamine (5.3 g, 26.9 mmol) in ethyl acetate (50 mL) was added, via an addition funnel) to a solution of thiophosgene (2.15 mL, 28.2 mmol) and triethylamine (7.87 mL, 56.5 mmol) in ethyl acetate (30 mL) at 0° C. The resultant solution was stirred at ambient temperature overnight. The solution was washed with saturated aqueous sodium bicarbonate and dried over sodium sulfate. The solvent was evaporated in vacuo, and the residue was purified by flash chromatography on silica gel eluted with ethyl acetate/hexanes (1/9 to 3/7) to give the product, 4-isothiocyanatomethyl-2-methoxy-1-methoxymethoxy-benzene, as a waxy tan solid, 4.9 g (76%). $^1$H NMR (CDCl$_3$): δ 3.51 (s, 3H), 3.91 (s, 3H), 4.64 (s, 2H), 5.23 (s, 2H), 6.83 (m, 2H) and 7.14 (d, J=8 Hz).

A solution of cis-1-benzyl-6-methoxy-1,2,3,4-tetrahydro-naphthalen-2-ylamine hydrochloride (0.306 g, 1.01 mmol), diisopropylethylamine (0.264 mL, 1.51 mmol) and 4-isothiocyanatomethyl-2-methoxy-1-methoxymethoxy-benzene (0.253 g, 1.06 mmol) in acetonitrile (10 mL) was stirred at ambient temperature overnight. The solvent was evaporated in vacuo, and the residue was purified by reverse phase preparative HPLC, on a C18 column eluted with a gradient of 40 to 90% acetonitrile in water with 0.1% TFA, to give the product, 1-(1-benzyl-6-methoxy-1,2,3,4-tetrahydro-naphthalen-2-yl)-3-(3-methoxy-4-methoxymethoxy-benzyl)-thiourea, 0.21 g (41%). $^1$H NMR (CDCl$_3$): δ 1.64 (br s, 1H), 1.85 (m, 1H), 2.04 (m, 1H), 2.63 (m, 1H), 2.82 (m, 2H), 2.98 (m, 1H), 3.33 (m, 1H), 3.49 (s, 3H), 3.78 (s, 3H), 3.84 (s, 3H), 4.32 (br s, 2H), 5.19 (s, 2H), 5.7 (br s, 1H), 6.0 (br s, 1H), 6.64 (m, 3H), 6.80 (s, 1H), 6.91 (d, J=8.4 Hz, 1H), 7.03 (d, J=8.2 Hz, 1H) and 7.11 to 7.28 (m, 5H). MS: m/z 507 (M+H)$^+$.

A solution of 1-(1-benzyl-6-methoxy-1,2,3,4-tetrahydro-naphthalen-2-yl)-3-(3-methoxy-4-methoxymethoxy-benzyl)-thiourea (0.21 g, 0.42 mmol) in isopropanol/acetonitrile (10 mL/10 mL) was treated with concentrated hydrochloric acid (1 mL) and stirred at ambient temperature for 30 min. The solvent was evaporated under a stream of nitrogen, and the residue was partitioned between dichloromethane and water. The organic layer was collected and the solvent was evaporated. The product was purified by flash chromatography, on silica gel eluted with ethyl acetate/hexanes (1/2) to give the title product, compound 3, as a colorless solid, 0.184 g (95%). $^1$H NMR (CDCl$_3$): δ 1.83 (m, 1H), 2.05 (m, 1H), 2.67 (m, 1H), 2.81 (m, 2H), 3.03 (br s, 1H), 3.78 (s, 3H), 3.84 (s, 3H), 4.25 (br s, 2H), 5.61 (s, 2H), 6.59 to 6.68m, 3H), 6.74

(s, 1H), 6.80 (d, J=8 Hz, 1H), 6.94 (d, J=8.5 Hz, 1H) and 7.12 to 7.29 (m, 5H). MS: m/z 463 (M+H)+.

EXAMPLE 7

1-(1-Benzyl-6-fluoro-1,2,3,4-tetrahydro-naphthalen-2-yl)-3-(2-oxy-isoquinolin-5-yl)-urea Compound 85

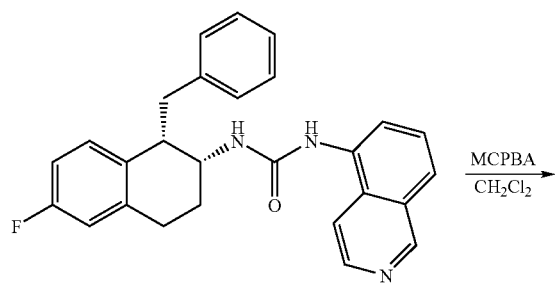

7-1

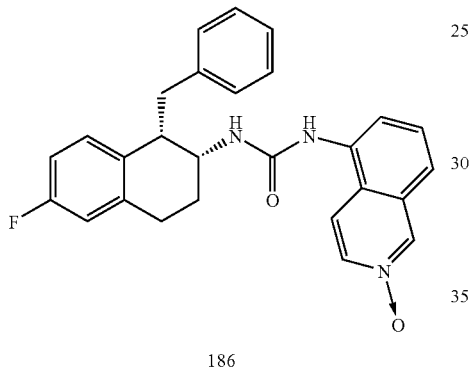

186

The aminotetralin urea 1 (0.150 g, 0.00035 mol) was dissolved in 5 mL of dichloromethane. The solid m-chloroperbenzoic acid (0.066 g, 0.00039 mol) was added and the reaction mixture was stirred at room temperature for 16 hours. Thin layer chromatography (silica gel, CH$_2$Cl$_2$/5% MeOH) indicated the presence of starting material. An additional portion of MCPBA was added (0.050 g) and stirring at room temperature was continued for another 4 hours. At the end of this period, the reaction was complete was indicated by TLC. Saturated sodium bicarbonate (25 mL) was cautiously added to the reaction mixture and the organic layer was separated. The organic layer was washed with 25 mL of brine, dried over Na$_2$SO$_4$ and evaporated in vacuo. The residue was purified by flash chromatography on silica gel eluting with CH$_2$Cl$_2$/4% MeOH. The product 2 was obtained as a light brown powder (0.120 g, 0.00027 mol). $^1$H NMR (CD$_3$OD): δ 1.8-2.1 (m, 2H), 2.9-3.1 (m, 4H), 3.6 (m, 1H), 4.2 (m, 1H), 6.6-6.9 (m, 3H), 7.1-7.3 (m, 5H), 7.6-7.8 (m, 2H), 8.0 (bd, 1H), 8.2 (bt, 2H), 8.9 (s, 1H); MS (M+): 442.

EXAMPLE 8

1-(1-Benzyl-6-fluoro-1,2,3,4-tetrahydro-naphthalen-2-yl)-3-(1-chloro-isoquinolin-5-yl)-urea Compound 79

(1-Chloro-isoquinolin-5-yl)-carbamic acid phenyl ester (150 mgs, 0.5 mmol), 1-Benzyl-6-fluoro-1,2,3,4-tetrahydro-naphthalen-2-ylamine hydrochloride (146 mgs, 0.5 mmol), and sodium bicarbonate (42 mgs, 0.5 mmol) were combined and stirred for one hour in DMSO (4ml) at ambient temperature. The product was purified by directly injecting the crude reaction onto a reverse phase prep-HPLC (10-90% water:acetonitrile gradient). The appropriate fractions were lyophilized to yield 1-(1-Benzyl-6-fluoro-1,2,3,4-tetrahydro-naphthalen-2-yl)-3-(1-chloro-isoquinolin-5-yl)-urea (64 mgs, 28%) MS (MH+) 459; $^1$H NMR (CD$_3$OD) δ 1.93-2.06 (m, 1H), 2.09-2.13 (m, 1H), 2.91-3.07 (m, 4H), 3.40-3.42 (m, 1H), 4.07-4.10 (s, 1H), 6.69-6.78 (m, 1H), 6.80-6.89 (m, 2H), 7.12-7.26 (m, 5H), 7.72 (t, 1H, J=8.2 Hz), 7.83 (d, 1H, J=6.1 Hz), 8.19 (d, 1H, J=8.6 Hz), 8.17-8.24 (m, 2H). HPLC R$_t$=4.04 min (50-90% water:acetonitrile gradient, 100% pure).

EXAMPLE 9

1-(1-Benzyl-6-fluoro-1,2,3,4-tetrahydro-naphthalen-2-yl)-3-(1-methyl-isoquinolin-5-yl)-urea Compound 80

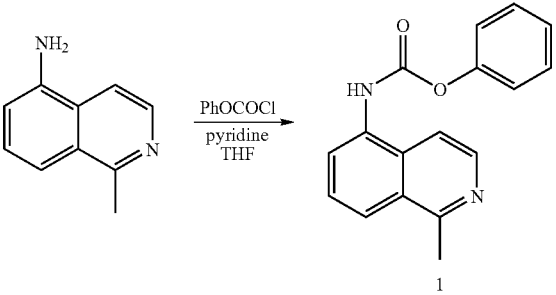

1

A. 1-Methyl-5-aminoisoquinoline (*J. Med Chem.*, 1968, 11,700), (0.01 mole, 1.58 g) was dissolved in 20 mL of tetrahydrofuran (THF). Pyridine (0.011 mole, 0.88 g, 0.88 mL) was added followed by the careful addition of phenylchloroformate (0.011 mole, 1.72 g, 1.4 mL). The reaction mixture immediately turned yellow and turbid. Stirring at room temperature was continued for 4 hours. The reaction mixture was evaporated in vacuo. The residue was taken up in 50 mL of dichloromethane, washed with 2×100 mL saturated sodium bicarbonate then 2×100mL of water. The organic layer was dried over sodium sulfate and evaporated in vacuo to give a thick dark yellow-brown oil. This oil was triturated with diethylether to give the carbamate product 1 as a yellowish-brown solid.

$^1$H NMR (CDCl$_3$): δ 3.0 (bs, 3H), 7.2 (m, 3H), 7.3-7.4 (m, 2H), 7.5-7.6 (m, 2H), 7.8 (bs, 1H), 8.2 (bs, 1H), 8.4 (bt, 1H).

MS (MH+): 279

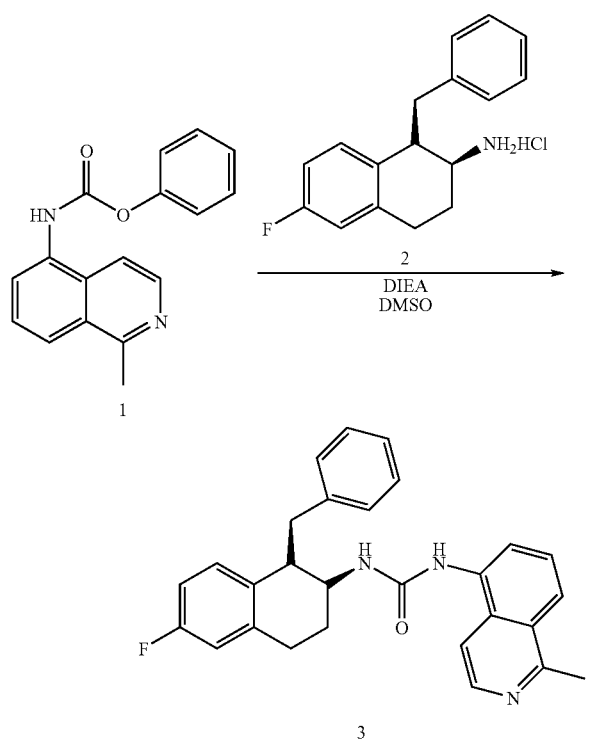

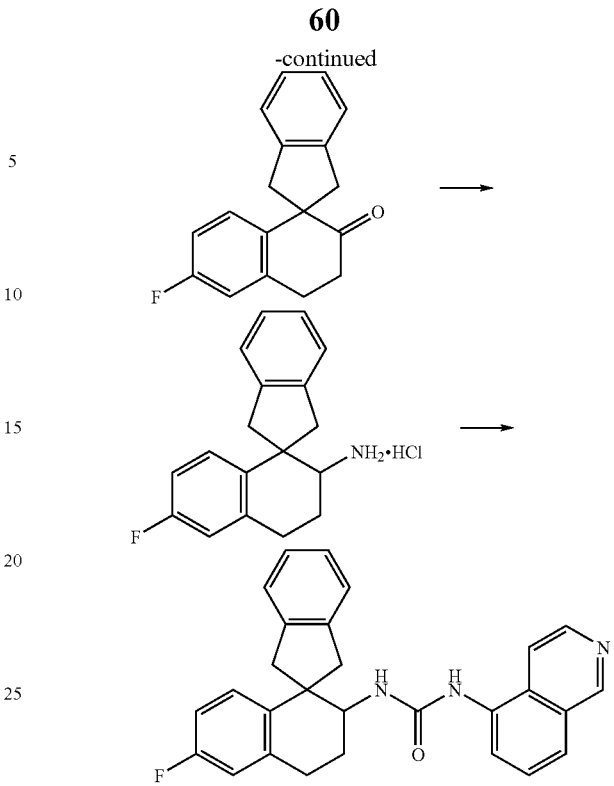

B. 1-Methyl-isoquinolin-5-yl-carbamic acid phenyl ester 1 obtained in step A (0.001 mole, 0.278 g) was dissolved in 5 mL of dimethylsulfoxide. Diisopropylethyl amine (0.0011 mole, 0.14 g, 0.2 mL) was added followed by the addition of 1-benzyl-6-fluoro-1,2,3,4-tetrahydro-naphthalen-2-ylamine hydrochloride 2 (0.0011 mole, 0.321 g). The reaction mixture was stirred at room temperature for 16 hours. The reaction mixture was then poured into 20 mL of water containing 5 mL of 1N sodium hydroxide. The precipitated solid was collected by filtration. This solid was chromatographed on silica gel eluting with a gradient of methylene chloride/3-10% methanol. Subsequently the product was further purified by recrystallization from ethyl acetate. The title compound 3 was obtained as an off-white solid (0.272 g, 0.0006 mole).

$^1$H NMR (CDCl$_3$): δ 1.8-1.9 (m, 2H), 2.7-2.8 (m, 4H), 2.95 (s, 3H), 3.2-3.2 (m, 1H), 4.1-4.2 (m, 1H), 5.1 (d, 1H), 6.4-6.6 (m, 2H), 6.8 (d, 1H), 6.9 (s, 1H), 7.0 (d, 1H), 7.1-7.2 (m, 2H), 7.4-7.5 (m, 2H), 7.7 (d, 1H), 7.9 (d, 1H), 8.3 (d, 1H).

MS (MH+): 440

EXAMPLE 10

Spiro{indan-2,1'-(1',2',3',4'-tetrahydronaphthalene)-2'-yl}-3-isoquinolin-5-yl-urea Compound 122

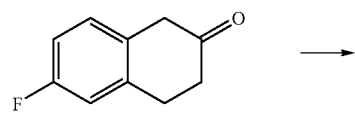

A. 6-Fluoro-3,4-dihydro-1H-naphthalen-2-one (2.472 g, 15.06 mmol) was dissolved in 75 mL THF and cooled on an ice bath with stirring under nitrogen. o-Xylene dibromide (4.378 g, 16.59 mmol) was added to the cooled tetralone solution. Separately potassium tert-butoxide (3.73 g, 33.2 mmol) was slurried in a combination of 75 mL THF and 10 mL tBuOH. The KOtBu slurry was added to the reaction mixture over a period of 15 minutes. The reaction was stirred on the ice bath for one hour then at room temperature for an additional hour after which time the entire reaction mixture was filtered over a pad of celite. The filtrate was evaporated in vacuo to give a residue which was taken up in 100 mL diethyl ether, washed twice with 50 mL 1N HCl and once with 50 mL brine. The organics were dried with MgSO$_4$, filtered and evaporated in vacuo to give the crude product which was purified by chromatography over silica gel eluting with 0-10% EtOAc in hexanes. Evaporation of the proper fractions yielded the product as an off-white solid (3.09 g, 11.6 mmol).

$^1$H NMR (CDCl$_3$): δ 7.33-7.17 (m, 4H), 7.07 (q, 1H), 6.93 (dd, 1H), 6.82 (dt, 1H), 3.81 (d, 2H), 3.19 (m, 4H), 2.79 (t, 2H).

B. The spirotetralone from step A (3.06 g, 11.5 mmol) was dissolved in 150 mL MeOH along with NH$_4$OAc (13.57 g, 176.1 mmol) and NaCNBH$_3$ (3.7 g, 59 mmol). The mixture was kept under a nitrogen atmosphere and heated to reflux for 3 hours. The reaction was concentrated in vacuo, mixed with 100 mL water and basified with 25 mL 50% NaOH. The basified mixture was extracted three times with 50 mL methylene chloride. The combined organics were washed once with 50 ml brine, dried with Na$_2$SO$_4$, filtered and concentrated in vacuo to give the crude free base. The free base was then dissolved in diethyl ether, acidified with ethereal HCl and evaporated in vacuo. The solid residue was triturated with 50 mL hot EtOAc, filtered and dried to yield the product HCl salt as a white powder (2.867 g, 9.44 mmol). MS: M+H$^+$ =268.1; $^1$H NMR (d6-DMSO): δ 8.22 (br s, 3H), 7.33 (d, 1H), 7.24 (m, 3H), 7.01 (d, 1H), 6.87 (d, 2H), 3.71 (m, 1H), 3.52 (d, 1H), 3.38 (d, 1H), 3.11 (d, 1H), 2.97 (m, 3H), 2.15 (m, 2H).

C. The spirotetralin salt from step B (0.304 g, 1.00 mmol) was dissolved in 6 mL DMSO along with iPr₂NEt (0.38 mL, 2.2 mmol) and 5-aminoisoquinoline phenylcarbamate (0.308 g, 1.02 mmol). The reaction was stirred overnight then poured into 100 mL water. The solid which formed was collected by filtration, rinsed with water then triturated first with diethyl ether and finally with hexanes to give the product urea as a tan powder (0.287 g, 0.66 mmol). MS: M+H$^+$=438.4; $^1$H NMR (d6-DMSO): δ 9.27 (s, 1H), 8.67 (s, 1H), 8.52 (d, 1H), 8.38 (d, 1H), 7.89 (d, 1H), 7.72 (d, 1H), 7.61 (t, 1H), 7.32 (d, 1H), 7.70 (m, 3H), 7.04 (dd, 1H), 7.00-6.76 (m, 3H), 4.26 (m, 1H), 3.39 (m, 2H), 3.19 (d, 1H), 3.05-2.88 (m, 3H), 2.18-1.92 (m, 2H).

EXAMPLE 11

Experimental Protocol for Resolution

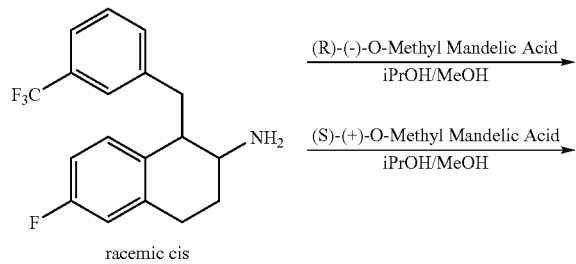
racemic cis

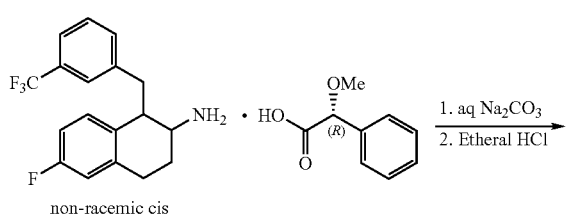
non-racemic cis

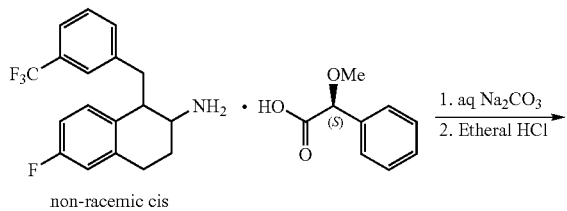
non-racemic cis

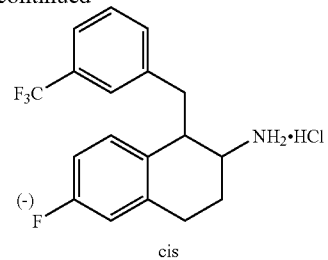
cis

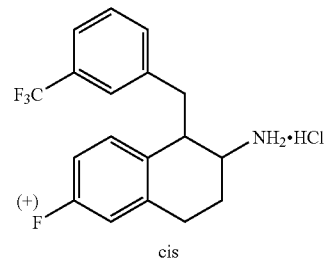
cis

A. 6-F-α-(3-trifluoromethylbenzyl)-β-aminotetralin (1.931 g, 5.97 mmol) was dissolved in 50 mL 1:1 iPrOH/MeOH. (R)-(−)—O-Methyl mandelic acid (0.992 g, 5.97 mmol) was added and the mixture was heated to reflux. An additional 170 mL 1:1 iPrOH/MeOH was added to bring the total volume of solvent to 220 mL and make a clear solution. The solution was then allowed to sit and cool overnight. The resulting crystalline material was collected by filtration, rinsed with a small amount of 1:1 iPrOH/MeOH and dried. This batch of crystals was re-crystallized as before from 125 mL 1:1 iPrOH/MeOH. After filtration and drying, 625 mg of the salt of the aminotetralin with (R)-(−)—O-methyl mandelic acid (1.28 mmol) were obtained.

B. The combined mother liquors, filtrates, and rinsates from above were evaporated under vacuum. The residue was partitioned between 200 mL Et₂O and 100 mL 10% Na₂CO₃ solution. The organics were separated, washed again with 100 mL 10% Na₂CO₃ and then with 100 mL brine. The organics were dried over Na₂SO₄, treated with charcoal, filtered and evaporated in vacuo to give the recovered aminotetralin (1.399 g, 4.33 mmol). To this was added (S)-(+)—O-methyl mandelic acid (0.719 g, 4.33 mmol) and 190 mL 1:1 iPrOH/MeOH and the mixture was heated to reflux to give a clear solution. The solution was then allowed to sit and cool overnight. The resulting crystalline material was collected by filtration, rinsed with a small amount of 1:1 iPrOH/MeOH and dried. This batch of crystals was re-crystallized as before from 140 mL 1:1 iPrOH/MeOH. After filtration and drying, 759 mg of the salt of the aminotetralin with (S)-(+)—O-methyl mandelic acid (1.55 mmol) were obtained.

C. Each of the mandelate salts thus prepared was separately suspended in 100 mL Et₂O, washed with 50 mL 10% Na₂CO₃ then with 50 mL brine. The organics were then dried with Na₂SO₄, filtered and evaporated in vacuo. The residue was dissolved in MeOH and excess ethereal HCl was added. The mixture was evaporated in vacuo and the resulting solids were triturated with hexanes, filtered and dried under vacuum.

The HCl salt derived from the aminotetralin resolved with (R)-(−)—O-methyl mandelic acid (0.422 g, 1.17 mmol): [α]$_D$=−159.0° (c=1, MeOH).

The HCl salt derived from the aminotetralin resolved with (S)-(+)—O-methyl mandelic acid (0.506 g, 1.41 mmol): [α]$_D$=+159.1° (c=1, MeOH).

The $^1$H NMR spectra of the hydrochloride salts were identical: $^1$H NMR (d6-DMSO): 8.64 (br s, 3H), 7.59 (d, 1H), 7.52 (t, 1H), 7.42 (m, 2H), 6.99 (dd, 1H), 6.63 (dt, 1H), 5.91 (dd, 1H), 3.59 (m, 1H), 3.34-3.19 (m, 2H), 3.08 (m, 1H), 2.92 (m, 1H), 2.59 (d, 1H), 2.08 (m, 2H). MS: M+H$^+$=324.1

D. Other resolutions were performed in a similar manner to yield the results as shown in the table below.

| Racemic Amine | Resolving Acid | Solvent | $[\alpha]_D$ of the HCl Salts (c = 1, MeOH) |
|---|---|---|---|
| 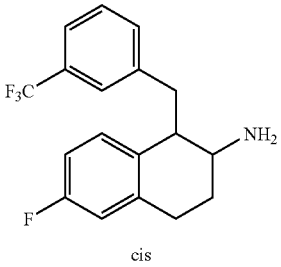 [SMILES: NC1CCc2cc(F)ccc2C1Cc1cccc(C(F)(F)F)c1] cis | 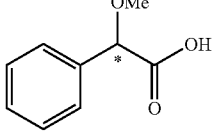 | 1:1 iPrOH:MeOH | +159.1°/−159.0° |
| 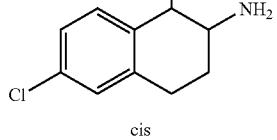 cis | 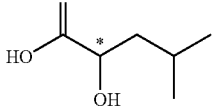 | iPrOH | +213.0°/−216.6° |
| 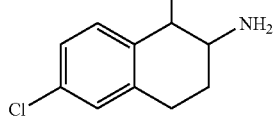 trans | 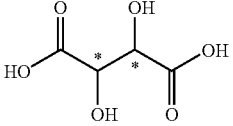 | 14-67:1 EtOH:H₂O | +70.7°/−71.4° |

Using the procedures of the Examples above and the appropriate reagents, starting materials and purification methods known to those skilled in the art, other compounds of the present invention may be prepared including, but not limited to:

TABLE 1

Mass Spectral Data for Selected Compounds

| No. | Substituents on Formula (Ia) | MW (calc) | Parent Peak (obs) |
|---|---|---|---|
| 3 | $R_1$ is 6-OMe, $R_2$ is Ph, m is 1, L is —$CH_2$—, $R_3$ is (3-OMe-4-OH)Ph, and X is S; (cis) | 462.6 | 463.1 |
| 4 | $R_1$ is H, $R_2$ is 3-Pyridinyl, m is 1, L is —$CH_2$—, $R_3$ is (3-OMe-4-(Methoxymethyleneoxy)Ph, and X is S; (cis) | 477.6 | 477.8 |
| 5 | $R_1$ is H, $R_2$ is 3-Pyridinyl, m is 1, L is —$CH_2$—, $R_3$ is (3-OMe-4-OH)Ph, and X is S; (cis) | | |
| 6 | $R_1$ is 6-OMe, $R_2$ is 3-Pyridinyl, m is 1, L is —$CH_2$—, $R_3$ is (3-OMe-4-OH)Ph, and X is S; (cis) | 463.6 | 464.1 |
| 7 | $R_1$ is 6-OMe, $R_2$ is —CH=$CH_2$, m is 1, L is —$CH_2$—, $R_3$ is (3-OMe-4-(Methoxymethyleneoxy)Ph, and X is S; (cis) | 456.6 | 457.1 |
| 8 | $R_1$ is 6-OMe, $R_2$ is 4-Imidazolyl, m is 1, L is —$CH_2$—, $R_3$ is (3-OMe-4-OH)Ph, and X is S; | 452.6 | 453.1 |

TABLE 1-continued

Mass Spectral Data for Selected Compounds

| No. | Substituents on Formula (Ia) | MW (calc) | Parent Peak (obs) |
|---|---|---|---|
| 9 | $R_1$ is 6-OMe, $R_2$ is Ph, m is 1, L is —$CH_2$—, $R_3$ is (3,4-methylenedioxy)Ph, and X is O; | 444.5 | 445.1 |
| 10 | $R_1$ is 6-OMe, $R_2$ is Ph, m is 1, L is —$CH_2$—, $R_3$ is (3,4-diOMe)Ph, and X is O; | 460.6 | 461.1 |
| 11 | $R_1$ is 6-OMe, $R_2$ is Ph, m is 1, L is —$CH_2$—, $R_3$ is (4-tBu)Ph, and X is O; | 456.6 | 457.2 |
| 12 | $R_1$ is 6-OMe, $R_2$ is Ph, m is 1, L is —$CH_2CH_2$—, $R_3$ is (4-Cl)Ph, and X is O; | 449.0 | 449.1 |
| 13 | $R_1$ is 6-OMe, $R_2$ is Ph, m is 1, L is —$CH_2CH_2$—, $R_3$ is (3,4-diOMe)Ph, and X is O; | 474.6 | 475.1 |
| 14 | $R_1$ is 6-OMe, $R_2$ is Ph, m is 1, L is —$CH_2$—, $R_3$ is (3,4-methylenedioxy)Ph, and X is S; | 460.6 | 461.1 |
| 15 | $R_1$ is 6-OMe, $R_2$ is Ph, m is 1, L is —$CH_2$—, $R_3$ is (3,4-diOMe)Ph, and X is S; | 476.6 | 477.1 |
| 16 | $R_1$ is 6-OMe, $R_2$ is Ph, m is 1, L is —$CH_2$—, $R_3$ is (4-tBu)Ph, and X is S; | 472.7 | 473.1 |
| 17 | $R_1$ is 6-OMe, $R_2$ is Ph, m is 1, L is —$CH_2CH_2$—, $R_3$ is (4-Cl)Ph, and X is S; | 465.1 | 465.0 |
| 18 | $R_1$ is 6-OMe, $R_2$ is Ph, m is 1, L is —$CH_2CH_2$—, $R_3$ is (3,4-diOMe)Ph, and X is S; | 490.7 | 491.1 |
| 19 | $R_1$ is 6-OMe, $R_2$ is Ph, m is 1, L is —$CH_2$—, $R_3$ is (3-OMe-4-OH)Ph, and X is O; | 446.5 | 447.1 |
| 21 | $R_1$ is H, $R_2$ is Ph, m is 1, L is —$CH_2$—, $R_3$ is (3-OMe-4-(Methoxymethyleneoxy)Ph, and X is S; (cis) | 476.6 | 476.7 |
| 23 | $R_1$ is H, $R_2$ is Ph, m is 1, L is —$CH_2$—, $R_3$ is (3-OMe-4-OH)Ph, and X is S; (cis) | 432.6 | 433.1 |
| 24 | $R_1$ is 6-OMe, $R_2$ is Ph, m is 1, L is —$CH_2$—, $R_3$ is (4-N(Me)($C_5H_{11}$))Ph, and X is O; | 499.7 | 500.3 |
| 25 | $R_1$ is 6-OMe, $R_2$ is Ph, m is 1, L is —$CH_2$—, $R_3$ is (4-[N(Me)(cyclohexyl)])Ph, and X is O; | 511.7 | 512.3 |
| 26 | $R_1$ is 6-F, $R_2$ is Ph, m is 1, L is —$CH_2$—, $R_3$ is (3,4-diOMe)Ph, and X is S; (cis) | 450.6 | 451.1 |
| 27 | $R_1$ is 6-OMe, $R_2$ is Ph, m is 1, L is —$CH_2$—, $R_3$ is (4-$CF_3$)Ph, and X is O; | 468.5 | 469.3 |
| 28 | $R_1$ is 6-OMe, $R_2$ is Ph, m is 1, L is —$CH_2$—, $R_3$ is (3,4-diCl)Ph, and X is O; | 469.4 | 469.1 |
| 29 | $R_1$ is 6-OMe, $R_2$ is Ph, m is 1, L is —$CH_2CH_2$—, $R_3$ is (3,4-diCl)Ph, and X is O; | 483.4 | 483.7 |
| 30 | $R_1$ is 6-OMe, $R_2$ is Ph, m is 1, L is —$CH_2$—, $R_3$ is (4-$CF_3$)Ph, and X is S; | 484.6 | 485.6 |
| 31 | $R_1$ is 6-OMe, $R_2$ is Ph, m is 1, L is —$CH_2$—, $R_3$ is (3,4-diCl)Ph, and X is S; | 485.5 | 485.0 |
| 32 | $R_1$ is 6-OMe, $R_2$ is Ph, m is 1, L is —$CH_2CH_2$—, $R_3$ is (3,4-diCl)Ph, and X is S; | 499.5 | 499.0 |
| 33 | $R_1$ is 6-OMe, $R_2$ is Ph, m is 1, L is a direct bond, $R_3$ is 5-isoquinolinyl, and X is O; | 437.5 | 438.4 |
| 34 | $R_1$ is 6-OMe, $R_2$ is Ph, m is 1, L is a direct bond, $R_3$ is 3-quinolinyl, and X is O; | 437.5 | 438.7 |
| 35 | $R_1$ is 6-OMe, $R_2$ is Ph, m is 1, L is a direct bond, $R_3$ is 8-(2-naphtholyl), and X is O; | 452.5 | 453.1 |
| 36 | $R_1$ is H, $R_2$ is H, m is 0, L is a direct bond, $R_3$ is 5-isoquinolinyl, and X is O; | 317.4 | 359.1 (MeCN) |
| 37 | $R_1$ is 6-F, $R_2$ is H, m is 0, L is a direct bond, $R_3$ is 5-isoquinolinyl, and X is O; | 335.4 | 336.2 |
| 38a | $R_1$ is 6-F, $R_2$ is Ph, m is 1, L is a direct bond, $R_3$ is 5-isoquinolinyl, and X is O; (racemate) | 425.5 | 426.3 |
| 38b | $R_1$ is 6-F, $R_2$ is Ph, m is 1, L is a direct bond, $R_3$ is 5-isoquinolinyl, and X is O; (enantiomer 1) | 425.5 | 426 |
| 38c | $R_1$ is 6-F, $R_2$ is Ph, m is 1, L is a direct bond, $R_3$ is 5-isoquinolinyl, and X is O; (enantiomer 2) | 425.5 | 426 |
| 39 | $R_1$ is 6-Br, $R_2$ is Ph, m is 1, L is a direct bond, $R_3$ is 5-isoquinolinyl, and X is O; (cis) | 486.4 | 485.9 |
| 40 | $R_1$ is 6,7-diOMe, $R_2$ is Ph, m is 1, L is a direct bond, $R_3$ is 5-isoquinolinyl, and X is O; (cis) | 467.6 | 468.2 |
| 41 | $R_1$ is 7-Cl, $R_2$ is Ph, m is 1, L is a direct bond, $R_3$ is 5-isoquinolinyl, and X is O; (cis) | 441.9 | 442.0 |
| 42 | $R_1$ is 5-Cl, $R_2$ is Ph, m is 1, L is a direct bond, $R_3$ is 5-isoquinolinyl, and X is O; (cis) | 441.9 | 441.9 |
| 43 | $R_1$ is H, $R_2$ is Ph, m is 1, L is a direct bond, $R_3$ is 5-isoquinolinyl, and X is O; | 407.5 | 408.2 |
| 44 | $R_1$ is 6-OMe, $R_2$ is (3-Cl)Ph, m is 1, L is a direct bond, $R_3$ is 5-isoquinolinyl, and X is O; (cis) | 472.0 | 472.3 |

TABLE 1-continued

Mass Spectral Data for Selected Compounds

| No. | Substituents on Formula (Ia) | MW (calc) | Parent Peak (obs) |
|---|---|---|---|
| 45 | $R_1$ is 6-OMe, $R_2$ is 3-Pyridinyl, m is 1, L is a direct bond, $R_3$ is 5-isoquinolinyl, and X is O; (cis) | 438.5 | 439.0 |
| 46 | $R_1$ is 6-OMe, $R_2$ is (3-Cl)Ph, m is 1, L is a direct bond, $R_3$ is 5-isoquinolinyl, and X is O; (trans) | 472.0 | 471.9 |
| 47 | $R_1$ is 6-OMe, $R_2$ is 3-Pyridinyl, m is 1, L is a direct bond, $R_3$ is 5-isoquinolinyl, and X is O; (trans) | 438.5 | 438.8 |
| 48 | $R_1$ is 6,7-diOMe, $R_2$ is Ph, m is 1, L is a direct bond, $R_3$ is 5-isoquinolinyl, and X is O; (trans) | 467.6 | 468.2 |
| 49 | $R_1$ is 6-OMe, $R_2$ is (2-Cl)Ph, m is 1, L is a direct bond, $R_3$ is 5-isoquinolinyl, and X is O; (cis) | 472.0 | 473.3 |
| 50 | $R_1$ is 6-OMe, $R_2$ is (4-Cl)Ph, m is 1, L is a direct bond, $R_3$ is 5-isoquinolinyl, and X is O; (cis) | 472.0 | 472.3 |
| 51 | $R_1$ is 6-OMe, $R_2$ is H, m is 0, L is a direct bond, $R_3$ is 5-isoquinolinyl, and X is O; | 347.4 | 348.6 |
| 52 | $R_1$ is 6-OMe, $R_2$ is (2-Cl)Ph, m is 1, L is a direct bond, $R_3$ is 5-isoquinolinyl, and X is O; (trans) | 472.0 | 472.2 |
| 53 | $R_1$ is 6-OMe, $R_2$ is (2-CF$_3$)Ph, m is 1, L is a direct bond, $R_3$ is 5-isoquinolinyl, and X is O; | 505.5 | 506.4 |
| 54 | $R_1$ is 6-OMe, $R_2$ is (3-CF$_3$)Ph, m is 1, L is a direct bond, $R_3$ is 5-isoquinolinyl, and X is O; | 505.5 | 506.4 |
| 55 | $R_1$ is 6-OMe, $R_2$ is (4-CF$_3$)Ph, m is 1, L is a direct bond, $R_3$ is 5-isoquinolinyl, and X is O; | 505.5 | 506.3 |
| 56 | $R_1$ is 6-OH, $R_2$ is Ph, m is 1, L is a direct bond, $R_3$ is 5-isoquinolinyl, and X is O; | 423.5 | 424.2 |
| 57 | $R_1$ is H, $R_2$ is —CH=CH$_2$, m is 1, L is a direct bond, $R_3$ is 5-isoquinolinyl, and X is O; | 357.4 | 358.2 |
| 58 | $R_1$ is 6-Br, $R_2$ is H, m is 0, L is a direct bond, $R_3$ is 5-isoquinolinyl, and X is O; | 396.3 | 397.9 |
| 59 | $R_1$ is 6-Cl, $R_2$ is H, m is 0, L is a direct bond, $R_3$ is 5-isoquinolinyl, and X is O; | 351.8 | 351.9 |
| 60 | $R_1$ is 6-F, $R_2$ is Ph, m is 1, L is —CH$_2$—, $R_3$ is 5-isoquinolinyl, and X is O; | 439.5 | 440.2 |
| 61 | $R_1$ is 7-Cl, $R_2$ is H, m is 0, L is a direct bond, $R_3$ is 5-isoquinolinyl, and X is O; | 351.8 | 351.9 |
| 62 | $R_1$ is 8-Cl, $R_2$ is Ph, m is 1, L is a direct bond, $R_3$ is 5-isoquinolinyl, and X is O; | 441.9 | 441.9 |
| 63 | $R_1$ is 6-OMe, $R_2$ is (4-CN)Ph, m is 1, L is a direct bond, $R_3$ is 5-isoquinolinyl, and X is O; | 462.6 | 463.2 |
| 64 | $R_1$ is 6-OMe, $R_2$ is (4-Br)Ph, m is 1, L is a direct bond, $R_3$ is 5-isoquinolinyl, and X is O; | 516.4 | 517.9 |
| 65 | $R_1$ is 6-Cl, $R_2$ is CN, m is 1, L is a direct bond, $R_3$ is 5-isoquinolinyl, and X is O; (cis) | 390.0 | 390.9 |
| 66 | $R_1$ is 6,7-diF, $R_2$ is Ph, m is 1, L is a direct bond, $R_3$ is 5-isoquinolinyl, and X is O; | 443.5 | 443.9 |
| 67 | $R_1$ is 6-F, $R_2$ is Ph, m is 1, L is a direct bond, $R_3$ is 8-(2-naphtholyl), and X is O; | 440.5 | 441.1 |
| 68 | $R_1$ is 6-OMe, $R_2$ is —CH=CH$_2$, m is 1, L is a direct bond, $R_3$ is 5-isoquinolinyl, and X is O; | 387.5 | 388.4 |
| 69 | $R_1$ is 6-F, $R_2$ is —CH=CH$_2$, m is 1, L is a direct bond, $R_3$ is 5-isoquinolinyl, and X is O; | 375.4 | 376.4 |
| 70 | $R_1$ is 6-OMe, $R_2$ is (4-OMe)Ph, m is 1, L is a direct bond, $R_3$ is 5-isoquinolinyl, and X is O; (trans) | 467.6 | 468.2 |
| 71 | $R_1$ is 6-F, $R_2$ is Cyclopropyl, m is 1, L is a direct bond, $R_3$ is 5-isoquinolinyl, and X is O; | 389.5 | 390.5 |
| 72 | $R_1$ is 6-OMe, $R_2$ is (4-OMe)Ph, m is 1, L is a direct bond, $R_3$ is 5-isoquinolinyl, and X is O; (cis) | 467.6 | 468.2 |
| 73 | $R_1$ is 6-OMe, $R_2$ is (2-OMe)Ph, m is 1, L is a direct bond, $R_3$ is 5-isoquinolinyl, and X is O; | 467.6 | 468.2 |
| 74 | $R_1$ is 6-OMe, $R_2$ is (4-Benzyloxy)Ph, m is 1, L is a direct bond, $R_3$ is 5-isoquinolinyl, and X is O; | 543.4 | 544.1 |
| 75 | $R_1$ is 6-OMe, $R_2$ is Ph, m is 1, L is —CH$_2$—, $R_3$ is 4-Pyridinyl, and X is O; | | |
| 76 | $R_1$ is 6-F, $R_2$ is 2-Thienyl, m is 1, L is a direct bond, $R_3$ is 5-isoquinolinyl, and X is O; | 431.5 | 432.0 |
| 77 | $R_1$ is 6-OMe, $R_2$ is (2,6-diF)Ph, m is 1, L is a direct bond, $R_3$ is 5-isoquinolinyl, and X is O; | 473.5 | 474.4 |
| 81a | $R_1$ is 6-F, $R_2$ is Ph, m is 1, L is a direct bond, $R_3$ is 3-Me-5-isoquinolinyl, and X is O; (cis) (enantiomer 1) | 439.5 | 440 |
| 81b | $R_1$ is 6-F, $R_2$ is Ph, m is 1, L is a direct bond, $R_3$ is 3-Me-5-isoquinolinyl, and X is O; (cis) (enantiomer 2) | 439.5 | 440 |
| 85a | $R_1$ is 6-F, $R_2$ is Ph, m is 1, L is a direct bond, $R_3$ is 5-isoquinolinyl-N-oxide, and X is O; (cis) (enantiomer 1) | 441.5 | 442 |

TABLE 1-continued

Mass Spectral Data for Selected Compounds

| No. | Substituents on Formula (Ia) | MW (calc) | Parent Peak (obs) |
|---|---|---|---|
| 85b | $R_1$ is 6-F, $R_2$ is Ph, m is 1, L is a direct bond, $R_3$ is 5-isoquinolinyl-N-oxide, and X is O; (cis) (enantiomer 2) | 441.5 | 442 |
| 86 | $R_1$ is 6-Cl, $R_2$ is Ph, m is 1, L is a direct bond, $R_3$ is 5-isoquinolinyl, and X is O; | 442 | 442 |
| 87 | $R_1$ is 6-OCH$_3$, $R_2$ is Ph, m is 1, L is a direct bond, $R_3$ is 5-isoquinolinyl, and X is O; (cis) (enantiomer 2) | 437.5 | 438.2 |
| 88 | $R_1$ is 6-F, $R_2$ is 3-furanyl, m is 1, L is a direct bond, $R_3$ is 5-isoquinolinyl, and X is O; (cis) | 415.5 | 416.4 |
| 89 | $R_1$ is 6-OCH$_3$, $R_2$ is 3-thienyl, m is 1, L is a direct bond, $R_3$ is 5-isoquinolinyl, and X is O | 443.6 | 444.4 |
| 90 | $R_1$ is 6-OCH$_3$, $R_2$ is 2,4 di-F Ph, m is 1, L is a direct bond, $R_3$ is 5-isoquinolinyl, and X is O; (cis) | 473.5 | 474.4 |
| 91 | $R_1$ is 6-OCH$_3$, $R_2$ is 2,4 di-F Ph, m is 1, L is a direct bond, $R_3$ is 5-isoquinolinyl, and X is O; (trans) | 473.5 | 474.5 |
| 92 | $R_1$ is 6-OCH$_3$, $R_2$ is Ph, m is 1, L is a direct bond, $R_3$ is 5-isoquinolinyl, and X is O; (cis) (enantiomer 1) | 437.5 | 438.1 |
| 93 | $R_1$ is 6-F, $R_2$ is Ph, m is 1, L is a direct bond, $R_3$ is 5-isoquinolinyl, and X is O; (cis) (enantiomer 1) | 425.5 | 426.4 |
| 94 | $R_1$ is 6-F, $R_2$ is Ph, m is 1, L is a direct bond, $R_3$ is 5-isoquinolinyl, and X is O; (cis) (enantiomer 2) | 425.5 | 426.6 |
| 95 | $R_1$ is 6-Cl, $R_2$ is Ph, m is 1, L is a direct bond, $R_3$ is 5-isoquinolinyl, and X is O; (cis) | 442.0 | 442.5 |
| 96 | $R_1$ is 6-F, $R_2$ is Ph, m is 1, L is a direct bond, $R_3$ is 5-isoquinolinyl-N-oxide, and X is O; (cis) (enantiomer 1) | 441.5 | 442.7 |
| 97 | $R_1$ is 6-F, $R_2$ is Ph, m is 1, L is a direct bond, $R_3$ is 5-isoquinolinyl-N-oxide, and X is O; (cis) (enantiomer 2) | 441.5 | 442.8 |
| 98 | $R_1$ is 6-F, $R_2$ is Ph, m is 1, L is a direct bond, $R_3$ is 4-Cl-5-isoquinolinyl, and X is O; (cis) | 460.0 | 460 |
| 99 | $R_1$ is 6-F, $R_2$ is Ph, m is 1, L is a direct bond, $R_3$ is 4-Cl-5-isoquinolinyl, and X is O; (cis) | 460.0 | 460 |
| 100 | $R_1$ is 6-F, $R_2$ is Ph, m is 1, L is a direct bond, $R_3$ is 3-methyl-5-isoquinolinyl, and X is O; (cis) (enantiomer 1) | 439.5 | 440.3 |
| 101 | $R_1$ is 6-F, $R_2$ is Ph, m is 1, L is a direct bond, $R_3$ is 3-methyl-5-isoquinolinyl, and X is O; (cis) (enantiomer 2) | 439.5 | 440.3 |
| 102 | $R_1$ is 6-F, $R_2$ is Ph, m is 1, L is a direct bond, $R_3$ is 1-methyl-5-isoquinolinyl, and X is O; (cis) (enantiomer 1) | 439.5 | 440.5 |
| 103 | $R_1$ is 6-F, $R_2$ is Ph, m is 1, L is a direct bond, $R_3$ is 1-methyl-5-isoquinolinyl, and X is O; (cis) (enantiomer 2) | 439.5 | 440.5 |
| 104 | $R_1$ is 6-F, $R_2$ is Ph, m is 1, L is a direct bond, $R_3$ is 1-Cl-5-isoquinolinyl, and X is O; (cis) (enantiomer 1) | 459.96 | 459.6 |
| 105 | $R_1$ is 6-F, $R_2$ is Ph, m is 1, L is a direct bond, $R_3$ is 1-Cl-5-isoquinolinyl, and X is O; (cis) (enantiomer 2) | 460.0 | 459.9 |
| 106 | $R_1$ is 6-Cl, $R_2$ is Ph, m is 1, L is a direct bond, $R_3$ is 5-isoquinolinyl-N-oxide, and X is O; (cis) | 457.9 | 459.0 |
| 107 | $R_1$ is 6-F, $R_2$ is 4-CF$_3$ Ph, m is 1, L is a direct bond, $R_3$ is 5-isoquinolinyl, and X is O; (cis) | 493.5 | 494.5 |
| 108 | $R_1$ is 6-F, $R_2$ is Ph, m is 1, L is a direct bond, $R_3$ is 1,3-diCl-5-isoquinolinyl, and X is O; (cis) | 494.4 | 494 |
| 109 | $R_1$ is 6-F, $R_2$ is Ph, m is 1, L is a direct bond, $R_3$ is 1,3-diCl-5-isoquinolinyl, and X is O; (cis) | 494.4 | 494 |
| 110 | $R_1$ is 6-F, $R_2$ is 3-CF$_3$ Ph, m is 1, L is a direct bond, $R_3$ is 5-isoquinolinyl, and X is O; (±cis) | 493.5 | 494.6 |
| 111 | $R_1$ is 6-F, $R_2$ is Ph, m is 1, L is a direct bond, $R_3$ is 8-Cl-5-isoquinolinyl, and X is O; (cis | 460.0 | 460 |
| 112 | $R_1$ is 6-F, $R_2$ is Ph, m is 1, L is a direct bond, $R_3$ is 1-piperidinyl-5-isoquinolinyl, and X is O; (cis) | 508.6 | 509 |
| 113 | $R_1$ is 6-F, $R_2$ is Ph, m is 1, L is a direct bond, $R_3$ is 1-OCH$_3$-5-isoquinolinyl, and X is O; (cis) | 455.5 | 456 |
| 114 | $R_1$ is 6-F, $R_2$ is Ph, m is 1, L is a direct bond, $R_3$ is 1-F-5-isoquinolinyl, and X is O; (cis) | 443.5 | 444 |
| 115 | $R_1$ is 6-F, $R_2$ is Ph, m is 1, L is a direct bond, $R_3$ is 1-N,N-dimethyl-5-isoquinolinyl, and X is O; (cis) | 468.6 | 469 |
| 116 | $R_1$ is 6-Cl, $R_2$ is nil, m is nil, $R_3$ is 1-CH$_3$-5-isoquinolinyl, and X is O | 365.9 | 366.0 |
| 117 | $R_1$ is 6-Cl, $R_2$ is nil, m is nil, $R_3$ is 1-Cl-5-isoquinolinyl, and X is O | 386.3 | 386.1 |

TABLE 1-continued

Mass Spectral Data for Selected Compounds

| No. | Substituents on Formula (Ia) | MW (calc) | Parent Peak (obs) |
|---|---|---|---|
| 118 | $R_1$ is 6-F, $R_2$ is 3-$CF_3$ Ph, m is 1, L is a direct bond, $R_3$ is 5-isoquinolinyl, and X is O; (cis)(enantiomer 1) | 493.5 | 494.6 |
| 119 | $R_1$ is 6-F, $R_2$ is 3-$CF_3$ Ph, m is 1, L is a direct bond, $R_3$ is 5-isoquinolinyl, and X is O; (cis)(enantiomer 2) | 493.5 | 494.6 |
| 120 | $R_1$ is 6-F, $R_2$ is 3-$CF_3$ Ph, m is 1, L is a direct bond, $R_3$ is 5-isoquinolinyl-N-oxide, and X is O; (cis) (enantiomer 1) | 509.5 | 510.2 |
| 121 | $R_1$ is 6-F, $R_2$ is 3-$CF_3$ Ph, m is 1, L is a direct bond, $R_3$ is 5-isoquinolinyl-N-oxide, and X is O; (cis) (enantiomer 2) | 509.5 | 510.2 |
| 122 | $R_1$ is 6-F, $R_2$ is spiro-2-indanyl, L is a direct bond, $R_3$ is 5-isoquinolinyl, and X is O | 437.5 | 438.4 |
| 123 | $R_1$ is 6-F, $R_2$ is 4-Cl, 3-$CF_3$ Ph, m is 1, L is a direct bond, $R_3$ is 5-isoquinolinyl, and X is O; (cis) | 527.9 | 528.3 |
| 124 | $R_1$ is 6-Cl, $R_2$ is Ph, m is 1, L is a direct bond, $R_3$ is 1-$CH_3$-5-isoquinolinyl, and X is O; (cis) (enantiomer 1) | 442.0 | 442.2 |
| 125 | $R_1$ is 6-Cl, $R_2$ is Ph, m is 1, L is a direct bond, $R_3$ is 1-$CH_3$-5-isoquinolinyl, and X is O; (cis) (enantiomer 2) | 442.0 | 442.2 |
| 126 | $R_1$ is 6-Cl, $R_2$ is Ph, m is 1, L is a direct bond, $R_3$ is 1-$CH_3$-5-isoquinolinyl, and X is O; (trans) (enantiomer 1) | 442.0 | 442.2 |
| 127 | $R_1$ is 6-Cl, $R_2$ is Ph, m is 1, L is a direct bond, $R_3$ is 1-$CH_3$-5-isoquinolinyl, and X is O; (trans) (enantiomer 2) | 442.0 | 442.2 |

BIOLOGICAL EXAMPLES

EXAMPLE 1

Human or Rat $VR_1$ Binding Assay

Compounds of the present invention were tested for their ability to inhibit the binding of [$^3$H] RTX to hVR1 receptors in a [$^3$H] RTX binding assay as previously described (Zhang, Sui-Po. Improved ligand binding assays for vanilloid receptors. PCT Int. Appl. (2002), 29 pp. CODEN: PIXXD2 WO 0233411 A1 20020425 AN 2002:315209; Grant, Elfrida R.; Dubin, Adrienne E.; Zhang, Sui-Po; Zivin, Robert A.; Zhong, Zhong Simultaneous intracellular calcium and sodium flux imaging in human vanilloid receptor 1 (VR1)-transfected human embryonic kidney cells: a method to resolve ionic dependence of VR1-mediated cell death. Journal of Pharmacology and Experimental Therapeutics (2002), 300(1), 9-17.)

HEK293 cells were transfected with human VR1 vanilloid receptors and washed with Hank's Balanced Salt Solution, dissociated with cell dissociation buffer (Sigma), and then centrifuged at 1000×g for 5 min. Cell pellets were homogenized in cold 20 mM HEPES buffer, pH 7.4, containing 5.8 mM NaCl, 320 mM sucrose, 2 mM $MgCl_2$, 0.75 $CaCl_2$ and 5 mM KCl and centrifuged at 1000×g for 15 min. The resultant supernate was then centrifuged at 40000×g for 15 min. The pelleted membranes were kept in an −80° C. freezer.

Approximately 120 μg protein/ml from membranes were incubated with indicated concentrations of [$^3$H] RTX in 0.5 ml of the HEPES buffer (pH 7.4) containing 0.25 mg/mL fatty acid-free bovine serum albumin at 37° C. for 60 min. The reaction mixture was then cooled to 4° C., 0.1 mg $\alpha_1$-acid glycoprotein added to each sample and incubated at 4° C. for 15 min. The samples were centrifuged at 18500×g for 15 min. The tip of the microcentrifuge tube containing the pellet was cut off. Bound radioactivity was quantified by scintillation counting. Non-specific binding was tested in the presence of 200 nM unlabeled RTX.

Alternatively, a binding assay using rat tissue was used. Rat spinal cord was homogenized twice with a Polytron and centrifuged at 3000 rpm for 10 min in HEPES buffer containing 20 mM HEPES, pH 7.4, NaCl 5.8 mM, sucrose 320 mM, $MgCl_2$ 2 mM, $CaCl_2$ 0.75 mM and KCl 5 mM. The supernatant was then centrifuged at 18,000 rpm for 20 min. The pellet was saved in a tube and 10 ml assay buffer was added into the tube. The pellet and buffer were mixed with a Polytron. The assay contained 120 μg/ml membrane protein and 0.3-0.6 nM [$^3$H]-RTX (NEN, Boston) in a total volume of 0.5 ml HEPES buffer. Following-incubation for 60 min at 37 C, the samples were cooled down on ice, and 100 mg of α-acid glycoprotein were added into the samples. After centrifugation at 13,000 rpm for 15 min, the supernatant was aspirated and the tips of tubes were cut off and placed into 6 ml vials. Data were calculated according to the equation: % inhibition=(total binding-binding)*100/(total binding−non specific binding). Ki value values were calculated using a Prism program.

EXAMPLE 2

Human $VR_1$ Functional Assay

The functional activity of the test compounds was determined by measuring changes in intracellular calcium concentration using a $Ca^{++}$-sensitive fluorescent dye and FLIPR™ technology. Increases in $Ca^{++}$ concentration were readily detected upon challenge with capsaicin.

HEK293 Cells expressing human VR1 were grown on poly-D-lysine coated 96 well black-walled plates (BD 354640) and 2 days later loaded with Fluo-3/AM for 1 hour and subsequently tested for agonist-induced increases in intracellular $Ca^{2+}$ levels using FLIPR™ technology. Cells were challenged with test compounds (at varying concentrations) and intracellular $Ca^{++}$ was measured for 3 min prior to the addition of capsaicin to all wells to achieve a final concentration of 0.015 µM eliciting ~80% maximal response. $EC_{50}$ or $IC_{50}$ values were determined from dose-response studies.

TABLE 2

Vanilloid In vitro assay data

| Compound No. | hVR1 $K_i$ (nM) | Rat VR1 Ki (nm) | $IC_{50}$ or $EC_{50}$ (nM) |
|---|---|---|---|
| 1 | 2530 | NT | 780 |
| 2 | 31600 | NT | NT |
| 3 | 98.9 | NT | 12 |
| 4 | NT | NT | 460 |
| 5 | NT | NT | 120 |
| 6 | >10000 | NT | 260 |
| 7 | NT | NT | 2400 |
| 8 | >10000 | NT | 10000 |
| 9 | >10000 | NT | 3000 |
| 10 | 13000 | NT | 690 |
| 11 | NT | NT | 10000 |
| 12 | NT | NT | >30000 |
| 13 | 3600 | NT | >30000 |
| 14 | >10000 | NT | 10000 |
| 15 | 3110 | NT | 440 |
| 16 | NT | NT | >30000 |
| 17 | NT | NT | >30000 |
| 18 | NT | NT | >30000 |
| 19 | 258 | NT | 92 |
| 20 | 5520 | NT | 10000 |
| 21 | 520 | NT | 520 |
| 23 | 98.2 | NT | 64 |
| 24 | NT | NT | >30000 |
| 25 | 70900 | NT | 10000 |
| 26 | 28.2 | NT | 69 |
| 27 | NT | NT | >30000 |
| 28 | NT | NT | >30000 |
| 29 | NT | NT | >30000 |
| 30 | NT | NT | >30000 |
| 31 | NT | NT | >30000 |
| 32 | NT | NT | >30000 |
| 33 | 3.37 | NT | 25 |
| 34 | NT | NT | >30000 |
| 35 | 9.64 | NT | 60 |
| 36 | 45.6 | NT | 41 |
| 37 | 24.9 | NT | 16 |
| 38a | 1.76 | NT | 12 |
| 38b | 0.72 | NT | NT |
| 38c | 3.59 | NT | NT |
| 39 | 0.89 | NT | 14 |
| 40 | 29.6 | NT | 195 |
| 41 | 4.58 | NT | 86 |
| 42 | 1.94 | NT | 16 |
| 43 | 3.66 | NT | 20 |
| 44 | 1.96 | NT | 13 |
| 45 | 1540 | NT | 511 |
| 46 | 8.81 | NT | 540 |
| 47 | 1030 | NT | 3000 |
| 48 | 19.3 | NT | 230 |
| 49 | 2.66 | NT | 130 |
| 50 | 1.8 | NT | 80 |
| 51 | 24 | NT | 72 |
| 52 | 12.3 | NT | 250 |
| 53 | 0.48 | NT | 4.8 |
| 54 | 2.04 | NT | 5.1 |
| 55 | 1.55 | NT | 2.3 |
| 56 | 277 | NT | 200 |
| 57 | 15.4 | NT | 120 |
| 58 | 2.62 | NT | 13 |
| 59 | 2.6 | NT | 9 |
| 60 | 4.99 | NT | 14 |
| 61 | 3.42 | NT | 5.7 |
| 62 | 7.59 | NT | 22 |
| 63 | 16.5 | NT | 21 |
| 64 | 1.28 | NT | 22 |
| 65 | NT | NT | 1000 |
| 66 | 1.82 | NT | 26 |
| 67 | 1.44 | NT | 390 |
| 68 | 21.3 | NT | 97 |
| 69 | 2.19 | NT | 100 |
| 70 | 5.55 | NT | 460 |
| 71 | 0.84 | NT | 350 |
| 72 | 7.52 | NT | 36 |
| 73 | 53.4 | NT | 110 |
| 74 | 11.3 | NT | 480 |
| 75 | NT | NT | 730 |
| 76 | 3.81 | NT | 140 |
| 77 | 6.26 | NT | 490 |
| 79a | 10.8 | NT | NT |
| 79b | 32.3 | NT | NT |
| 80a | 5.32 | NT | NT |
| 80b | 25.1 | NT | NT |
| 81a | 1.12 | NT | NT |
| 81b | 5.25 | NT | NT |
| 82 | 103 | NT | NT |
| 83 | 15.5 | NT | NT |
| 84a | 2700 | NT | NT |
| 84b | 2730 | NT | NT |
| 85a | 45.4 | NT | NT |
| 85b | 50.2 | NT | NT |
| 86 | 1.7 | NT | NT |
| 87 | NT | 53.7 | NT |
| 88 | 15.5 | 1270 | NT |
| 89 | NT | 1080 | NT |
| 90 | NT | 259 | NT |
| 91 | NT | 1480 | NT |
| 92 | NT | 7080 | NT |
| 93 | 3.59 | 517 | NT |
| 94 | 0.719 | 131 | NT |
| 95 | 1.7 | 217 | NT |
| 96 | 50.2 | NT | NT |
| 97 | 45.4 | NT | NT |
| 98 | 2730 | 100000 | NT |
| 99 | 2700 | 100000 | NT |
| 100 | 5.25 | 781 | NT |
| 101 | 1.12 | 53.1 | NT |
| 102 | 25.1 | 100000 | NT |
| 103 | 5.32 | 101 | NT |
| 104 | 32.3 | 100000 | NT |
| 105 | 10.8 | 4922 | NT |
| 106 | 8.6 | 2840 | NT |
| 107 | 0.93 | 28.7 | NT |
| 108 | 186 | NT | NT |
| 109 | 29.2 | 100000 | NT |
| 110 | 0.531 | 185 | NT |
| 111 | NT | 100000 | NT |
| 112 | NT | 100000 | NT |
| 113 | NT | 100000 | NT |
| 114 | NT | 100000 | NT |
| 115 | NT | 100000 | NT |
| 116 | NT | 100000 | NT |
| 117 | NT | 100000 | NT |
| 118 | 2.16 | 169 | NT |
| 119 | 0.5 | 152 | NT |
| 120 | 95.7 | 10000 | NT |
| 121 | 5.75 | 88.5 | NT |
| 122 | 73 | 1700 | NT |
| 123 | NT | NT | NT |
| 124 | NT | NT | NT |
| 125 | NT | NT | NT |
| 126 | NT | NT | NT |
| 127 | NT | NT | NT |

EXAMPLE 3

Broadly Stimulated Recombinant Human VR1 and Rat VR1 Functional Assays

When nociceptors are exposed to tissue damaging stimuli, VR1 receptors are activated by a plethora of stimuli. In an effort to identify potent and efficacious antagonists at human and rat VR1 that were active under conditions simulating aspects of in vivo inflammation functional assays were developed using FLIPR to determine antagonist activity against endogenous activators and stimuli likely to be present in inflammation. Cell lines were constructed that stably expressed recombinant rat VR1 (rVR1/HEK293). Cells were exposed to various stimuli at their $EC_{80}$, with the exception of the low pH and DTT stimuli.

Low pH (pH 5.9 (rat) or pH 6.5 (human). Cells were challenged for 5 min with low pH solution which produced an increase in intracellular $Ca^{2+}$ which was subsequently reduced by exposure to antagonists. After 3 min, other stimuli (a phorbol ester to induce phosphorylation, capsaicin, anandamide, redox agents) were applied to the cells to determine the potency of antagonists to block those stimuli in an acidic environment. Cells were maintained in low pH in all steps subsequent to the calcium dye loading step.

Phoshorylation by PKC. Previous studies have suggested that phorbol esters activate VR1 via PKC phosphorylation [Premkumar, 2000 #697; Vellani, 2001 #739]. These studies were corroborated and further studies were performed to confirm that the phorbol ester effect was not due to direct effects on the channel. The role of PKC was shown pharmacologically: phorbol-12-myristate-3-acetate (PMA) and other phorbol esters active at PKC (but not the inactive 4α-phorbol) caused an increase in intracellular $Ca^{2+}$ that was mediated by VR1. The rank order potency for the panel of phorbol esters was similar to their rank order potency to block PKC. The PKC inhibitors bisindolylmaleimide (BIM) and staurosporin blocked the PMA induced increase in $Ca^{2+}$. The $EC_{50}$ for PMA at either rat or human recombinant VR1 was 90 nM. Cells were challenged with 300 nM PMA (~$EC_{80}$) after 3 min in the indicated antagonist. The active phorbol ester effect was blocked by RR and CPZ and required extracellular $Ca^{2+}$. CPZ was more potent at the recombinant human compared to the rat receptor.

Anandamide. Anandamide is a brain-derived cannabinoid ligand that acts as a near full agonist at VR1 at low μM concentrations [Smart, 2000 #507]. The $EC_{50}$ of anandamide at recombinant rat and human receptors was 5 μM and 3 μM, respectively. The $IC_{50}$ was determined near the $EC_{80}$ of anandamide (10 μM).

Reactive oxygen species: Disturbances in the regulatory activities of free radicals may play a role in inflammation [Winrow, 1993]. Reactive oxygen species (ROS) such as $H_2O_2$ are formed in inflamed joints. $H_2O_2$ directly activates VR1: the increase in intracellular $Ca^{2+}$ is in part blocked by VR1 antagonists and the response is dependent on extracellular $Ca^{2+}$. The influx of $Ca^{2+}$ through VR1 may contribute to the known effects of ROS on signal transduction (e.g., phosphorylation of proteins) and downstream regulation of gene transcription. The $EC_{80}$ for $H_2O_2$-induced $Ca^{2+}$ flux in VR1/HEK cells was 0.015% $H_2O_2$ and this concentration was used to determine the $IC_{50}$ of VR1 antagonists.

Reducing agents: The reducing agent DTT also directly activates VR1 [Vyklicky, 2002]. Cells were challenged with 5-10 mM DTT to stimulate VR1 after 3 min incubation in compound.

Compound 33 potently blocked the activation of human recombinant VR1 elicited by the agonists shown in Table 3. The increase in intracellular $Ca^{2+}$ caused by acidic solutions, anandamide the PKC activator PMA, and H2O2 was completely abolished by Compound 33 in a dose dependent manner after 3 min incubation in antagonist (Table 3). The $IC_{50}$ values obtained in assays with low pH, anandamide and PMA stimuli were similar to the $IC_{50}$ values obtained against capsaicin-induced responses. Thus, Compound 33 is a potent antagonist against a panel of activators at the recombinant human receptor, with a more favorable pharmacological profile than the two most well studied antagonists, capsazepine and ruthenium red.

TABLE 3

Antagonism of recombinant human VR1 activated by a panel of stimuli in a $Ca^{2+}$ influx in vitro assay ($IC_{50}$ in nM)

| Compound | Low pH (nM) | Anandamide (nM) | PKC phosphorylation (nM) | PKC phosphorylation at low pH (nM) | $H_2O_2$ reactive oxygen species (nM) |
|---|---|---|---|---|---|
| 33 | 23, 40 | 41 | | 70 | 39 |
| Capsazepine (CPZ) | 110 | | 160 | 370 | |
| Ruthenium Red (RR) | 500 | | 500 | | |

The reference compounds used in these studies were the previously characterized VR1 antagonists capsazepine (CPZ) and ruthenium red. CPZ, previously the most potent antagonist at human VR1, shows similar potency (100-300 nM) at the human recombinant receptor to inhibit $Ca^{2+}$ activity induced by these stimuli (FIG. 1, left set of panels). For FIG. 1, human (left) and rat (right) vanilloid 1 receptor expressed in HEK 293 cells was stimulated by a number of different stimuli known to activate VR1. FIG. 1 shows the $IC_{50}$ values of the competitive vanilloid antagonist capsazepine for inhibition of the calcium flux induced by each of these activators. Note the similar potency of the compound at the human receptor stimulated by various stimuli, but the lower potency of the compound as an inhibitor of rat VR1.

Figure 2:
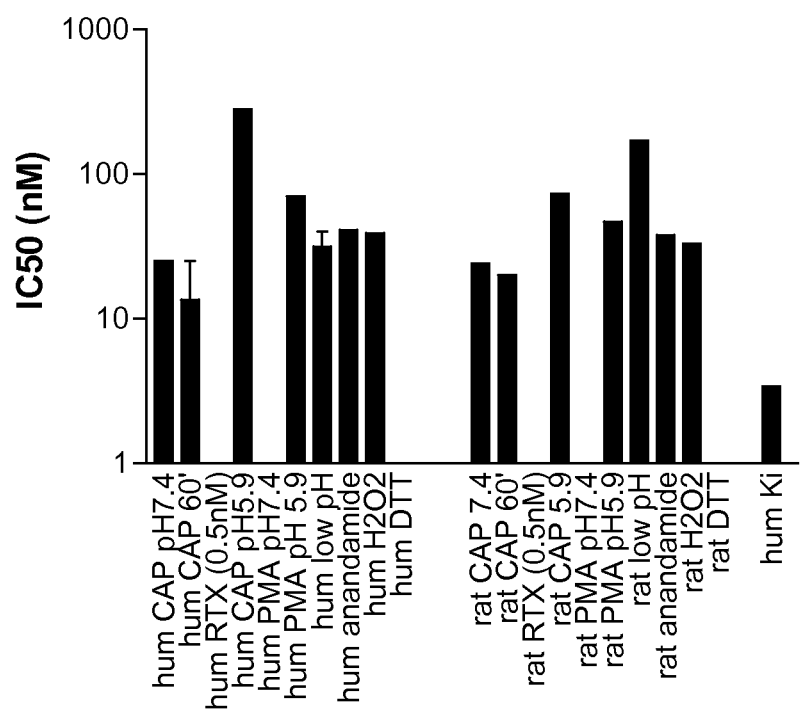
FIG. 2 shows the $IC_{50}$ values for inhibition by a compound of the invention of the calcium flux induced by a number of different stimuli known to activate VR1.

In FIG. 2, the human (left) and rat (right) vanilloid 1 receptor expressed in HEK 293 cells was stimulated by a number of different stimuli known to activate VR1. The $IC_{50}$ values for inhibition by example #33 of the calcium flux induced by each of these activators is seen in FIG. 2.

CPZ has been shown to have significantly lower potency at the rat receptor (recombinant and native receptors; [McIntyre, 2001]). Since many of our animal models were in rat, we cloned the rat VR1 and expressed it stably in HEK293 cells. We performed assays similar to those described for the human recombinant receptor with the exception that a lower pH was required in the $Ca^{2+}$ influx assay at the rat recombinant receptor.

As expected based on data from the literature, the CPZ profile revealed low potency against heat-induced responses at the recombinant rat receptor [Nagy, 1999]. With the exception of the pore blocker RR, antagonists tended to have a lower potency at the rat compared to the human recombinant receptor. Importantly, Compound 33 potently and completely blocks rat recombinant VR1 activated by acidic solution, anandamide, and $H_2O_2$, and PMA at acidic pH (Table 4).

TABLE 4

Antagonism of recombinant rat VR1 activated by a panel of stimuli in the $Ca^{2+}$ influx in vitro assay ($IC_{50}$ in nM)

| Compound | Low pH (nM) | Anandamide (nM) | PKC phosphorylation (nM) | PKC phosphorylation at low pH (nM) | $H_2O_2$ (NM) |
|---|---|---|---|---|---|
| Cmpd 33 | 170 | 38 | | 47 | 33 |
| Capazepine (CPZ) | 5000 | 1300 | 10000 | 10000 | |
| Ruthenium Red (RR) | | 1860 | 300 | | |

Compound 33 potently blocked the activation of rat recombinant VR1 elicited by the agonists shown in Table 4. The increase in intracellular $Ca^{2+}$ caused by acidic solutions, anandamide the PKC activator PMA at low pH, and $H_2O_2$ was completely abolished by Compound 33 in a dose dependent manner after 3 min incubation in antagonist (Table 4). The $IC_{50}$ values obtained in assays with low pH, anandamide and PMA stimuli were similar to the $IC_{50}$ values obtained against capsaicin-induced responses with the possible exception of the blockade of the low pH response. Thus, Compound 33 is a potent antagonist against a panel of activators at the recombinant rat receptor, with a more favorable pharmacological profile than the two most well studied antagonists, capsazepine and ruthenium red.

EXAMPLE 4

Electrophysiologic Functional Assay Using Dissociated Rat DRG Cells

Compounds 42, 95, 101, 105 and 106 were tested for their activity on VR1 expressed endogenously on small rat dorsal root ganglion (DRG) neurons. DRG neurons from normal rats were dissociated (see methods in Chaplan et al., 2003) and whole cell currents mediated by VR1 were recorded using the whole cell patch clamp technique. The estimated potency of the compounds were determined either 1) by measuring the shift in the capsaicin-induced dose response in the presence of compound or 2) by calculating the percent of capsaicin-induced current responses in the presence of compound under conditions of limited capsaicin-induced desensitization (i.e., using 0 $Ca^{2+}$-containing saline solutions). Under these conditions, repeated application of capsaicin produced similar current responses when 3 min recovery/washout periods were allowed. Briefly in the first method, if a cell was responsive to 300 nM capsaicin (~$EC_{20}$), compound was applied to the cell at 100 or 300 or 1000 nM to determine if the compound had intrinsic agonist activity and allow a 4-5 min incubation period prior to testing with capsaicin in the presence of compound. After 4-5 min exposure to compound, 1 μM capsaicin was applied in the presence of the same concentration of compound and incubated another 2-3 min. This was followed by application of 10 μM CAP in the presence of compound. Control cumulative capsaicin dose response curves (filled squares) were obtained from a cell (the approximate $EC_{50}$ in this cumulative dose response assay was ~1 μM CAP; 10 μM causes a maximal response). Vehicle caused no shift in the capsaicin concentration dependence (not shown). The ability of 1 and 10 μM CAP to cause an increased current after exposure to a compound of the invention was compared to controls.

In the second method, a nociceptor was challenged with 0.3 uM capsaicin while taking measurements of whole cell current using voltage ramp protocols. After washout of the capsaicin, cells were exposed to the compound for 4-5 min and subsequently challenged with 1 uM capsaicin (approximately the ED80 at the native receptor in this experiments) in the continued presence of compound. The current elicited near −100 mV was measured during the first and second capsaicin exposure. The percent of the response elicited by 0.3 uM capsaicin obtained during the exposure to 1 uM capsaicin/compound was calculated. After washout, the cell was challenged with 10 uM capsaicin in the presence of compound and subsequently washed again and challenged with capsaicin without compound.

TABLE 5

VR1 antagonists inhibit capsaicin-induced currents in dissociated rat DRG neurons

| Compound | Compound concentration (uM) | % of the initial CAP response in presence of 1 uM CAP | % of the initial CAP response in presence of 10 uM CAP |
|---|---|---|---|
| 42 | 0.3 | 0 | |
| 95 | 0.03 | 78 | 1073 |
| | 0.1 | 21 | 200 |
| | 0.1 | 4 | 12 |
| 101 | 0.03 | 14 | 54 |
| | 0.1 | 0 | 0 |
| 105 | 1 | 0 | 23 |
| | | 8 | 160 |
| 106 | 1 | 2 | 11 |
| vehicle | | 330 | |
| | | 115 | 180 |
| | | 171 | 204 |

All compounds inhibited the response to 1 uM capsaicin. The inhibition was dose dependent (compounds 95 and 101). The response to 10 uM capsaicin in the presence of compound was larger than the response to 1 uM capsaicin/compound with the exception of the cell challenged with 0.1 uM 101 which revealed no capsaicin induced current until the compound was washed out and capsaicin alone was applied to the cell. These results indicate that Compounds 95 and 101 appeared to shift the capsaicin dose response to the right in a dose dependent manner. PKB' values could not be determined because it is not known whether the blockade could not be surmounted by higher concentrations of capsaicin. Tested compounds had no detectable, reproducible effect on whole cell voltage-activated currents in the DRG neurons studied.

EXAMPLE 5

Carrageenan Paw-Induced Thermal Hyperalgesia

Each rat was placed on a heated surface (51° C.) in order to measure the time necessary to elicit a response, and an initial (baseline) response time to a thermal stimuli was recorded for each animal. A response is defined as any shaking, licking, or tucking of the treated paw or jumping. Animals not treated with a test compound respond in approximately 20 seconds. The maximal exposure time permitted is 60 seconds to prevent tissue damage. Rats were injected with an irritant (e.g., 1% carrageenan solution in 0.9% saline) subcutaneously into the sub-plantar tissue of the left hind paw to stimulate an acute inflammatory reaction.

Two hours later, the response time of the animal to the thermal stimulus was evaluated and compared to the animal's baseline response time. This shorter response time was recorded as percent hyperalgesia (% H). A cut-off value for % H (usually 75%) was used during analysis to ensure that the animals were hyperalgesic. Animals were then dosed with test drug or vehicle.

At some time(s) later (typically 45 and 90 minutes), the response time of the animal to the thermal stimulus was again evaluated. For each time point, a percent reversal of hyperalgesia (% R) was calculated using the following formula: % R=(Drug Latency−Carrageenan latency)/(Baseline latency−Carrageenan latency). $ED_{50}$ values were calculated from % R obtained at several drug doses.

| Cmpd No | CgHP $ED_{50}$ (mg/kg, po) |
|---|---|
| 33 | 0.276 |
| 57 | 0.354 |
| 4 | 0.804 |
| 17 | 19.958 |

TABLE 6

Percent Recovery at 1 mg/ml or $ED_{50}$ value (mg/kg, p.o.), each at 90 min.

| Compound | % Recovery | $ED_{50}$ (mg/kg, p.o.) |
|---|---|---|
| 106 | | 0.027 |
| 105 | | 0.394 |
| 107 | | 0.92 |
| 110 | 64.3 | |
| 120 | 83.0 | |
| 121 | 80.1 | |
| 124 | 55.2 | |
| 125 | 63.9 | |
| 126 | 46.0 | |
| 127 | 41.3 | |

EXAMPLE 6

Evaluation of Action on Isolated Guinea Pig Bronchial Rings

Aminotetralin VR1 antagonists were tested for their potency to block capsaicin-induced guinea pig bronchial ring contraction in a standard in vitro organ bath assay [Tucker, 2001]. Two mm rings of bronchial tissue obtained from male guinea pigs (325 g) were suspended in normal Krebs solution between two wire hooks under an initial loading tension of 1 gram. The saline was maintained in a 5% $CO_2$ and 95% $O_2$ atmosphere at 37° C. in the presence of indomethacin (5 μM). A sub-maximal dose of 5-Methylfurmethide (5Mef, 1 μM) was added to each tissue to determine responsiveness using an isometric force transducer. After washout, tissues were exposed to compounds or vehicle for 30 min, treated with thiorphan (10 μM, 5% $Na_2CO_3$), and primed using KCl in increasing linear concentrations from 1 mM at 1 mM intervals until a slight increase in muscle tone was induced (~1% of 5Mef response). A concentration-response curve was then constructed using capsaicin (10 nM-10 μM) increasing in 0.5 log unit increments. The dose response curve was calculated as % max of the 5-Mef response and estimated $pA_2$ were determined [Tucker, 2001]).

Both Compound 38a (FIG. 3) and Compound 105 (FIG. 4) inhibited capsaicin-evoked bronchial ring contraction with an estimated $pA_2$ of 8.0 and 6.2, respectively (Table 7). The potent antagonism of capsaicin-induced bronchial ring contraction indicated that these compounds may be effective inhibitors of cough and bronchial spasm mediated by VR1.

Figure 3:
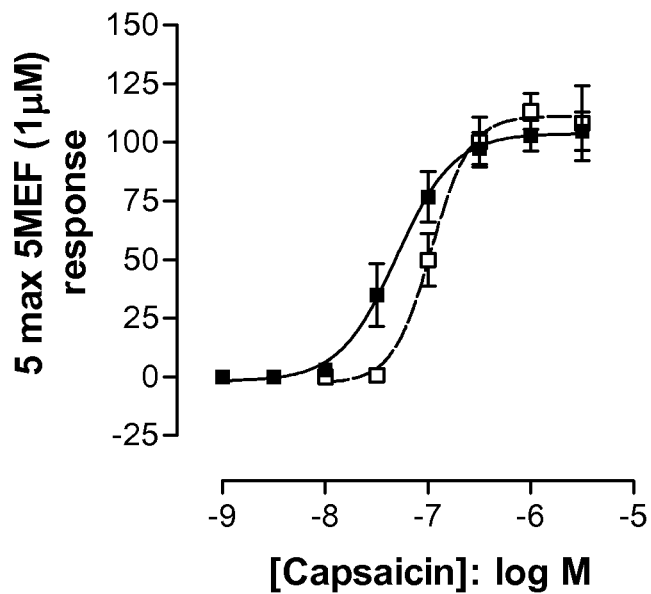
FIG. 3 shows inhibition by a compound of the invention of capsaicin-induced contraction of guinea pig bronchial rings in an isolated tissue assay.

In FIG. 3, inhibition of capsaicin-induced contraction of guinea pig bronchial rings is shown for an isolated tissue assay. The closed symbols represent the capsaicin-only concentration-response relationship, whereas the open symbols represent the capsaicin plus example number 105 concentration-response. The inhibition appears as a shift to the right of the concentration-response curve, resulting in a $pA_2$ (±SEM) value of 6.2±0.11.

Figure 4:
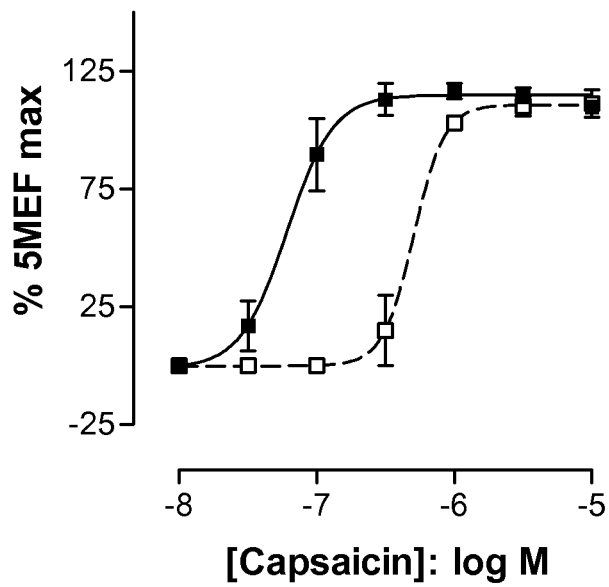
FIG. 4 shows inhibition by another compound of the invention of capsaicin-induced contraction of guinea pig bronchial rings in an isolated tissue assay.

In FIG. 4, inhibition of capsaicin-induced contraction of guinea pig bronchial rings is shown for an isolated tissue assay. The closed symbols represent the capsaicin-only concentration-response relationship, whereas the open symbols represent the capsaicin plus example number 38a concentration-response. The inhibition appears as a shift to the right of the concentration-response curve, resulting in a $pA_2$ (±SEM) value of 8.0±0.02.

TABLE 7

VR1 antagonist blocked capsaicin-induced guinea pig bronchial ring contraction in a competitive manner.

| Compound | Estimated $pA_2$ |
|---|---|
| 33 | 8.0 +/− 0.02 |
| 105 (1000 nM) | 6.2 +/− 0.11 |

EXAMPLE 7

Antitussive Efficacy of VR1 Antagonists

The antitussive activity of intraperitoneally (IP) administered compound is assessed at a single dose level against capsaicin-induced cough responses as compared to positive and vehicle controls. Thirty-six male Dunkin-Hartley guinea pigs (295-590 g, mean=425 g) are randomly allocated to one of three groups (n=12 guinea pigs per group). The blinding code is not revealed to the experimenter until coughs from all animals are tallied. Guinea pigs are dosed IP at −60 min with vehicle (15% Solutol in 5% dextrose solution); the positive control codeine (25 mg/kg), or test compound (20 mg/kg in 15% Solutol in 5% dextrose solution). Individual guinea pigs are placed in an exposure chamber with an airflow of 3 L/min at −10 min to acclimatize. At ±0 min, cough responses are induced by exposure to capsaicin aerosol (15 μM) generated by an ultrasonic nebulizer at a nebulization rate of 0.6 ml/min for 4 min. Coughs are counted throughout the 4 min capsaicin exposure and for a further 11 min. The mean±SEM number of capsaicin-induced cough responses recorded in vehicle pre-treated guinea pigs was 3.0±0.5. This level of response was reduced significantly to 0.58±0.15 coughs in codeine pre-treated guinea pigs (P<0.001) and is reduced in compound pre-treated guinea pigs. ANOVA statistical analysis was used to determine the level of significance.

The antitussive properties of test compounds are assessed in a citric acid-induced cough model as compared to positive and vehicle controls. Evaluation of a given compound in this paradigm is as follows: Six male Dunkin-Hartley guinea pigs (approximately 300-600 g) are randomly assigned to each treatment group. Guinea pigs are intra-peritoneally (IP) injected with vehicle, test compound, or positive control (codeine 25 mg/kg) 60 minutes prior to citric acid exposure. Individual guinea pigs are placed in an exposure chamber with an airflow of 3 L/min at −10 min to acclimatize. At ±0 min, cough responses are induced by exposure to nebulized citric acid. Coughs elicited during the 10-minute aerosol of citric acid and additional 5-minute observation period are recorded and analysed for onset of cough, and cough number and frequency. To eliminate bias, pre-treatments are randomised and the experiments are done blinded. The blinding code is not revealed to the experimenter until coughs from all animals are tallied.

EXAMPLE 8

Rodent Colitis Model

5% Dextran Sulfate Sodium administered in the drinking water of mice or rats for 7 days results in an acute colitis with some morphological changes that are similar to human ulcerative colitis. Among those changes are colon shortening, accumulation of neutrophils and other inflammatory cells, decreases in colon weight, decreases in body weight, tissue damage in the colon, and loss of stool consistency.

Each animal is dosed daily in the morning and late afternoon for BID dosing. Treatment with vehicle or test compound begins on day 0, immediately after initial body weights are taken, and ends on day 6. Water bottles are removed and replaced by graduated water bottles containing 5% DSS in indicated groups. Tap water remains on control groups only. Sufficient DSS drinking water is placed in graduated water bottles and refilled each day to monitor daily output. Animals are weighed daily from day 0 to 7, and animal condition and the consistency of stools recorded. Following sacrifice of the animal on day 7, the colon is surgically removed from the distal rectum (anus) to the cecal-colonic juncture and the colon length and weight measured. Colon slices may be obtained for histological evaluation. An active drug should decrease or eliminate disruption of the epithelium and colonic folds, dense inflammatory cell infiltrates, mucosal sloughing, etc. In life observations include monitoring for signs of gross toxicity and/or behavioral changes, gross evaluation of the skin and fur, motor activity and any behavioral patterns with special attention to tremors, convulsions and diarrhea. Water consumption and body weights are measured daily. Scores include ratings for colon weight loss, stool consistency, colon damage, and colon shortening, and are used to assemble a Disease Activity Score. An increase in myeloperoxidase activity occurs in this model and is evaluated separately.

EXAMPLE 9

Uterine Pain Assessment

Female adult virgin Sprague Dawley rats (190-290 g) are used. Rats are anesthetized with pentobarbital (50 mg/kg IP). One uterine horn is approached via a small ventral midline laparotomy and tightly ligated at its caudal end near the cervix with 3.0 silk suture to prevent leakage of mustard oil through the cervix and vagina. Using a 22G needle 0.1-0.2 ml of 10% mustard oil (Aldrich Chemical Co., Milwaukee Wis. USA; dissolved in mineral oil) or an equivalent volume of saline in sham control rats, are injected into the uterine lumen. The abdominal incision is then closed and the rats allowed to recover from anesthesia. Rats are then transferred to individual Plexiglas cages in a quiet environment (12/12 h light-dark cycle) with food and water ad libitum for nonstop videotape recording for the duration of the experiment. Compounds or vehicle is administered by the intended route before (therapeutic) or after (prophylactic) acquisition of hyperalgesia. The recording system consists of a camera connected to a videotape recorder with a wide range of recording and reading speeds to allow for detailed analysis of the movements of the rats. During the dark phase an infrared light is used to permit continuous filming. Animal behavior is analyzed post-hoc using a scoring system to count abnormal behaviors. Six characteristic abnormal behaviors are expected in uterine inflammation rats: (1) hunching (2) hump-backed position (3) repeated licking of the lower abdomen/ipsilateral flank (4) repeated waves of contraction of the ipsilateral oblique musculature with inward turning of the ipsilateral hind limb (5) stretching of the body (6) squashing of the lower abdomen against the cage floor. The effect of administered compounds on the intensity and frequency of pain related behaviors is quantitatively assessed.

EXAMPLE 10

Models of Itch, Contact Dermatitis, Eczema and Other Manifestations of Dermal Allergy, Hypersensitivity and/or Inflammation Vanilloid receptor modulators are tested in an animal model of contact dermatitis or itch, according to previously documented and validated methods, including but not limited to those described by Saint-Mezard et al. (2003), Gonzalez et al. (2001), Wille et al. (1998), Weisshaar et al. (1999) and Thomsen et al. (2002). In models of contact dermatitis, testing is conducted in mouse, guinea pig or human in response to a single (primary allergic dermatitis) or repeated (sensitized allergic dermatitis) topical or photomechanical exposure of the skin to one or more haptens selected from 12-myristate-13 acetate, picryl chloride, oxazolone, capsaicin, arachidonic acid, lactic acid, trans-retinoic acid or sodium lauryl sulfate. For increased sensitivity, animals are sensitized by pre-exposure to certain agents selected from dinitrochlorobenzene, para-phenylenediamine or oxazolone. For prophylactic or therapeutic testing, a vanilloid receptor modulator or vehicle control is administered to the test subjects by the enteral or parenteral route prior to or following hapten challenge. Significant differences in skin inflammation (erythema, edema, hyperthermia, etc.) for the test compound-treated subjects compared with vehicle-treated subjects demonstrate anti-allergy activity. The following additional dependent measures are also collected and compared: skin and/or lymph node levels of CF8+ T cells, interleukin-1 alpha and beta, tumor necrosis factor alpha, interferon gamma, nitric oxide, inducible nitric oxide synthase and keratinocyte apoptosis, Fas expression and/or inflammatory mediator secretion.

In models of itch, testing is conducted in mouse, rat, guinea pig or human in response to the sub- or intra-dermal injection or iontophoresis of pruritogens select4ed from serotonin, compound 48/80, leukotriene B4, arachidonic acid, prostaglandin E2, histamine, substance P, neurokinin A, neurokinin B, trypsin, hydroxyethylstarch or platelet-activating factor singly or in combination with mosquito bite or injection of salivary gland extract therefrom. In some cases, animals are inflamed by pre-exposure to certain agents, including but not limited to sodium lauryl sulfate. For prophylactic or therapeutic testing, a vanilloid receptor modulator or vehicle control is administered to the test subjects by the enteral or parenteral route prior to or following pruritogen challenge. Cumulative scratching behavior and/or number of scratches per unit time are measured. Significant differences in scratching behavior for the test compound-treated subjects compared with vehicle-treated subjects demonstrate anti-pruritic activity. The following additional dependent measures are collected and compared: skin inflammation (erythema, edema, hyperthermia, etc.), surface area of the wheal and flare, hyperalgesia, allodynia, plasma protein extravasation, inflammatory mediator release and serum immunoglobulin levels.

EXAMPLE 11

Models of Rhinitis and Other Manifestations of Nasal Hypersensitivity and/or Inflammation Vanilloid receptor modulators are tested in an animal model of rhinitis, according to previously documented and validated methods, including but not limited to those described by Hirayama et al. (2003), Tiniakov et al. (2003) and Magyar et al. (2002). Testing is conducted in mouse, guinea pig, dog or human in response to intranasal challenge with one or more irritants selected from bradykinin, histamine, pollens, dextran sulfate, 2,4-tolylene diisocyanate, *Bordetella bronchiseptica*, *Pasteurella multodica* or acetic acid. For increased sensitivity, animals may be sensitized by pre-exposure to ragweed or ovalbumin. For prophylactic or therapeutic testing, a vanilloid receptor modulator or vehicle control is administered to the test subjects by the enteral or parenteral route prior to or following irritant challenge. The relevant dependent measures collected are plasma extravasation of the nasal mucosa, nasal eosinophilia or neutrophilia, nasal mucosal or nasal cavity lavage fluid levels of IL-5, interferon gamma, histamine or IgE, serum immunoglobulin levels, rhinorrhea, cumulative time spent sneezing or number of sneezes per unit time, nasal airway volume, peak inspiratory flow and resistance, intranasal pressure and nasal lesions. Significant differences in one or more of these measures for the test compound-treated subjects compared with vehicle-treated subjects demonstrate anti-rhinitis activity.

EXAMPLE 12

Models of Anxiety, Panic Disorder and Other Non-Adaptive Stressful or Phobic Responses Vanilloid receptor modulators are tested in an animal model of anxiety, according to previously documented and validated methods, including but not limited to those reviewed by Imaizumi and Onodera (2000). Testing is conducted in mouse or rat and consists of methods to measure avoidance of aversive environmental stimuli selected from the Geller-type or Vogel-type anticonflict tests, the light/dark test, the hole-board test, the elevated plus-maze and the elevated T-maze. Prior to environmental exposure the test subject receives the prophylactic administration one or more times of a vanilloid receptor modulator, or vehicle control, by the enteral or parenteral route. The cumulative time or number of times spent engaged in the aversive behavior is measured. Significant differences in one or more of these measures for the test compound-treated subjects compared with vehicle-treated subjects are taken as evidence of anxiolytic activity.

The invention claimed is:
1. A compound of Formula (I):

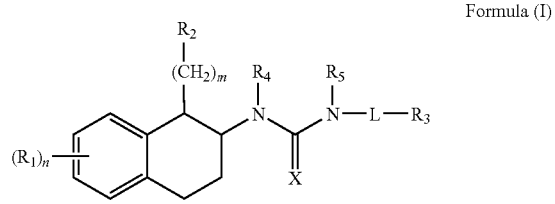

Formula (I)

wherein:
R$_1$ is a substituent independently selected from the group consisting of C$_{1-8}$alkanyl optionally independently substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cycloalkanylamino; cyano; carboxy; C$_{1-7}$alkanyloxycarbonyl; C$_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; (C$_{1-8}$alkanylamino)carbonyl; (arylamino)carbonyl and aryl(C$_{1-8}$alkanyl)carbonyl;
n is an integer from 1 to 3;
m is an integer from 0 to 3;
R$_2$ is independently selected from the group consisting of hydrogen; hydroxy; C$_{1-8}$alkanyl; C$_{2-8}$alkenyl; C$_{1-8}$alkylidenyl; C$_{1-8}$alkylidynyl; fluoro; chloro; C$_{3-8}$cycloalkanyl; phenyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; naphthyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; phenoxy optionally substituted with one to three substituents independently selected from the group consisting of halogen, hydroxy, C$_{1-8}$alkanyl, C$_{1-8}$alkanyloxy, fluorinated alkanyl, cyano and nitro; and heteroaryl optionally substituted with one to three substituents independently selected from the group consisting of C$_{1-6}$alkanyl and halogen wherein said heteroaryl is pyridyl, pyrimidyl, furyl, thienyl or imidazolyl; pyrrolidino; and piperidino;
L is a direct bond, C$_{1-8}$alkandiyl, C$_{2-8}$alkendiyl, C$_{2-8}$alkyndiyl, or C$_{3-8}$cycloalkandiyl;
R$_3$ is selected from the group consisting of phenyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; naphthyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; and heteroaryl optionally substituted with one to three substituents independently selected from the group consisting of C$_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide pyrimidyl, furyl, thienyl or imidazolyl;

R$_4$ is selected from the group consisting of hydrogen and C$_{1-8}$alkanyl;

R$_5$ is selected from the group consisting of hydrogen and C$_{1-8}$alkanyl;

X is selected from the group consisting of O and S; and an enantiomer, a diastereomer, a tautomer, or a pharmaceutically acceptable salt thereof.

2. A compound of Formula (I):

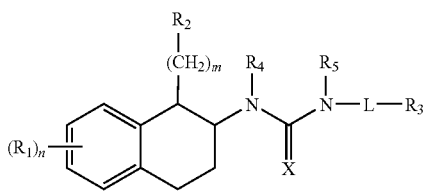

Formula (I)

wherein:

R$_1$ is a substituent independently selected from the group consisting of C$_{1-8}$alkanyl optionally independently substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cycloalkanylamino; cyano; carboxy; C$_{1-7}$alkanyloxycarbonyl; C$_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; (C$_{1-8}$ alkanylamino)carbonyl; (arylamino)carbonyl and aryl(C$_{1-8}$alkanyl)carbonyl;

n is an integer from 1 to 3;

m is an integer from 0 to 3;

R$_2$ is independently selected from the group consisting of hydrogen; C$_{2-8}$alkenyl; C$_{1-8}$alkylidenyl; C$_{1-8}$alkylidynyl; C$_{3-8}$cycloalkanyl; phenyl optionally substituted with one to three substituents independently selected from the group consisting of fluoro, chloro, bromo, hydroxy, C$_{1-8}$alkanyl, C$_{1-8}$alkanyloxy, phenyl (C$_{1-8}$)alkanyloxy, fluorinated alkanyl; naphthyl optionally substituted with one to three substituents independently selected from the group consisting of fluoro, chloro, bromo, hydroxy, C$_{1-8}$alkanyl, C$_{1-8}$alkanyloxy, phenyl(C$_{1-8}$)alkanyloxy, fluorinated alkanyl; and a heteroaryl optionally substituted with one to three substituents independently selected from the group consisting of C$_{1-6}$alkanyl and halogen wherein said heteroaryl is pyridyl, pyrimidyl, furyl, thienyl or imidazolyl;

L is a direct bond, C$_{1-8}$alkandiyl, C$_{2-8}$alkendiyl, C$_{2-8}$alkyndiyl, or C$_{3-8}$cycloalkandiyl;

R$_3$ is selected from the group consisting of phenyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; naphthyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; and heteroaryl optionally substituted with one to three substituents independently selected from the group consisting of C$_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide pyrimidyl, furyl, thienyl or imidazolyl;

R$_4$ is selected from the group consisting of hydrogen and C$_{1-8}$alkanyl;

R$_5$ is selected from the group consisting of hydrogen and C$_{1-8}$alkanyl;

X is selected from the group consisting of O and S; and an enantiomer, a diastereomer, a tautomer, or a pharmaceutically acceptable salt thereof.

3. The compound of claim 2 wherein L is a direct bond or C$_{1-8}$alkandiyl.

4. The compound of claim 2 wherein R$_3$ is selected from the group consisting of naphthyl substituted with hydroxyl; quinolinyl optionally substituted with one or more substituents selected from the group consisting of methyl and chloro; quinolinyl-N-oxide; isoquinolinyl optionally substituted with one or more substituents selected from the group consisting of methyl and chloro; and isoquinolinyl-N-oxide.

5. A compound of Formula (I):

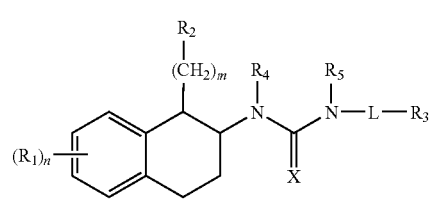

Formula (I)

wherein:

R$_1$ is a substituent independently selected from the group consisting of C$_{1-8}$alkanyl optionally independently substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cyclo alkanylamino; cyano; carboxy; C$_{1-7}$alkanyloxycarbonyl; C$_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; (C$_{1-8}$alkanylamino)carbonyl; (arylamino)carbonyl and aryl(C$_{1-8}$alkanyl)carbonyl;

n is an integer from 1 to 3;

m is an integer from 0 to 3;

R$_2$ is independently selected from the group consisting of hydrogen; C$_{2-8}$alkenyl; C$_{1-8}$alkylidenyl; C$_{1-8}$alkylidynyl; C$_{3-8}$cycloalkanyl; phenyl optionally substituted with one to three substituents independently selected from the group consisting of fluoro, chloro, bromo, C$_{1-8}$alkanyloxy, phenyl(C$_{1-8}$)alkanyloxy and fluorinated alkanyl; naphthyl optionally substituted with one to three substituents independently selected from the group consisting of fluoro, chloro, bromo, C$_{1-8}$alkanyloxy, phenyl(C$_{1-8}$)alkanyloxy and fluorinated alkanyl; pyridyl; pyrimidyl; furyl; thienyl and imidazolyl;

L is a direct bond, C$_{1-8}$alkandiyl, C$_{2-8}$alkendiyl, C$_{2-8}$alkyndiyl, or C$_{3-8}$cycloalkandiyl;

R$_3$ is selected from the group consisting of phenyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; naphthyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; and heteroaryl optionally substituted with one to three substituents independently selected from the group consisting of C$_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

R$_4$ is selected from the group consisting of hydrogen and C$_{1-8}$alkanyl;

R$_5$ is elected from the group consisting of hydrogen and C$_{1-8}$alkanyl;

X is selected from the group consisting of O and S; and an enantiomer, a diastereomer, a tautomer, or a pharmaceutically acceptable salt thereof.

6. The compound of claim 5 wherein L is a direct bond or C$_{1-8}$alkandiyl.

7. The compound of claim 5 wherein R$_3$ is selected from the group consisting of naphthyl substituted with hydroxyl; quinolinyl optionally substituted with one or more substituents selected from the group consisting of methyl and chloro; quinolinyl-N-oxide; isoquinolinyl optionally substituted with one or more substituents selected from the group consisting of methyl and chloro and isoquinolinyl-N-oxide.

8. A compound of Formula (I):

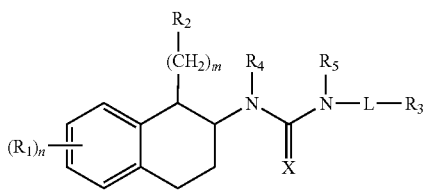

Formula (I)

wherein:

R$_1$ is a substituent independently selected from the group consisting of C$_{1-8}$alkanyl independently substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cycloalkanylamino; cyano; carboxy; C$_{1-7}$alkanyloxycarbonyl; C$_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; (C$_{1-8}$alkanylamino)carbonyl; (arylamino)carbonyl and aryl(C$_{1-8}$alkanyl)carbonyl;

n is an integer from 1 to 3;

m is an integer from 0 to 3;

R$_2$ is independently selected from the group consisting of C$_{2-8}$alkenyl; C$_{1-8}$alkylidenyl; C$_{1-8}$alkylidynyl; C$_{3-8}$cycloalkanyl; phenyl optionally substituted with one to three substituents independently selected from the group consisting of fluoro, chloro, bromo, and fluorinated alkanyl;

L is a direct bond, C$_{1-8}$alkandiyl, C$_{2-8}$alkendiyl, C$_{2-8}$alkyndiyl, or C$_{3-8}$cycloalkandiyl;

R$_3$ is selected from the group consisting of phenyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; naphthyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; and heteroaryl substituted with one to three substituents independently selected from the group consisting of C$_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

R$_4$ is selected from the group consisting of hydrogen and C$_{1-8}$alkanyl;

R$_5$ is selected from the group consisting of hydrogen and C$_{1-8}$alkanyl;

X is selected from the group consisting of O and S; and an enantiomer, a diastereomer, a tautomer, or a pharmaceutically acceptable salt thereof.

9. The compound of claim 8 wherein L is a direct bond or C$_{1-8}$alkandiyl.

10. The compound of claim 8 wherein R$_3$ is selected from the group consisting of naphthyl substituted with hydroxyl; quinolinyl optionally substituted with one or more substituents selected from the group consisting of methyl and chloro; quinolinyl-N-oxide; isoquinolinyl optionally substituted with one or more substituents selected from the group consisting of methyl and chloro and isoquinolinyl-N-oxide.

11. A compound of Formula (I):

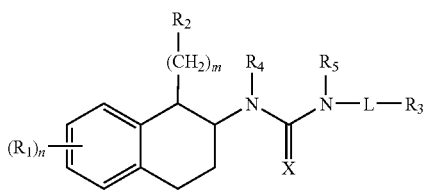

Formula (I)

wherein:
R$_1$ is a substituent independently selected from the group consisting of C$_{1-8}$alkanyl independently substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cycloalkanylamino; cyano; carboxy; C$_{1-7}$alkanyloxycarbonyl; C$_{1-7}$alkanylcarbonyloxy; formyl; carbamoyl; phenyl substituted with one to three substituents independently selected from the group consisting of halogen, hydroxyl, nitro, amino and cyano; aroyl; carbamoyl; amidino; (C$_{1-8}$alkanylamino)carbonyl; (arylamino)carbonyl and aryl(C$_{1-8}$alkanyl)carbonyl;
n is 1;
m is an integer from 0 to 3;
R$_2$ is independently selected from the group consisting of hydrogen; hydroxy; C$_{1-8}$alkanyl; C$_{2-8}$alkenyl; C$_{1-8}$alkylidenyl; C$_{1-8}$alkylidynyl; fluoro; chloro; C$_{3-8}$cycloalkanyl; phenyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; naphthyl optionally substituted with one to three substituents independently selected from the group consisting of halogen, hydroxy, C$_{1-8}$alkanyl, C$_{1-8}$alkanyloxy, phenyl(C$_{1-8}$) alkanyloxy, fluorinated alkanyl, cyano, nitro, amino, C$_{1-8}$alkanylamino, and C$_{1-8}$dialkanylamino; phenoxy optionally substituted with one to three substituents independently selected from the group consisting of halogen, hydroxy, C$_{1-8}$alkanyl, C$_{1-8}$alkanyloxy, fluorinated alkanyl, cyano and nitro; and heteroaryl optionally substituted with one to three substituents independently selected from the group consisting of C$_{1-6}$alkanyl and halogen wherein said heteroaryl is pyridyl, pyrimidyl, furyl, thienyl or imidazolyl; pyrrolidino; and piperidino;
L is a direct bond, C$_{1-8}$alkandiyl, C$_{2-8}$alkendiyl, C$_{2-8}$alkyndiyl, or C$_{3-8}$cycloalkandiyl;
R$_3$ is selected from the group consisting of phenyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; naphthyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; and heteroaryl optionally substituted with one to three substituents independently selected from the group consisting of C$_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;
R$_4$ is selected from the group consisting of hydrogen and C$_{1-8}$alkanyl;
R$_5$ is selected from the group consisting of hydrogen and C$_{1-8}$alkanyl;
X is selected from the group consisting of O and S; and
an enantiomer, a diastereomer, a tautomer, or a pharmaceutically acceptable salt thereof.

12. The compound of claim 11 wherein R$_2$ is independently selected from the group consisting of hydrogen; C$_{2-8}$alkenyl; C$_{1-8}$alkylidenyl; C$_{1-8}$alkylidynyl; C$_{3-8}$cycloalkanyl; phenyl optionally substituted with one to three substituents independently selected from the group consisting of fluoro, chloro, bromo, hydroxy, C$_{1-8}$alkanyl, C$_{1-8}$alkanyloxy, phenyl(C$_{1-8}$) alkanyloxy, and fluorinated alkanyl; naphthyl optionally substituted with one to three substituents independently selected from the group consisting of fluoro, chloro, bromo, hydroxy, C$_{1-8}$alkanyl, C$_{1-8}$alkanyloxy, phenyl(C$_{1-8}$)alkanyloxy, and fluorinated alkanyl; and a heteroaryl optionally substituted with one to three substituents independently selected from the group consisting of C$_{1-6}$alkanyl and halogen wherein said heteroaryl is pyridyl, pyrimidyl, furyl, thienyl or imidazolyl.

13. The compound of claim 11 wherein L is a direct bond or C$_{1-8}$alkandiyl.

14. The compound of claim 11 wherein R$_3$ is selected from the group consisting of naphthyl substituted with hydroxyl; quinolinyl optionally substituted with one or more substituents selected from the group consisting of methyl and chloro; quinolinyl-N-oxide; isoquinolinyl optionally substituted with one or more substituents selected from the group consisting of methyl and chloro and isoquinolinyl-N-oxide.

15. A compound of Formula (I):

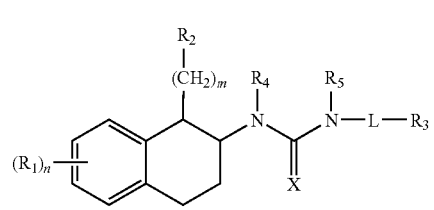

Formula (I)

wherein:
R$_1$ is a substituent independently selected from the group consisting of C$_{1-8}$alkanyl optionally independently substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cyclo alkanylamino; cyano; carboxy; C$_{1-7}$alkanyloxycarbonyl; C$_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is an integer from 0 to 1;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and an enantiomer, a diastereomer, a tautomer, or a pharmaceutically acceptable salt thereof.

16. The compound of claim 15 wherein $R_2$ is independently selected from the group consisting of hydrogen; $C_{2-8}$alkenyl; $C_{1-8}$alkylidenyl; $C_{1-8}$alkylidynyl; $C_{3-8}$cycloalkanyl; phenyl optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl; naphthyl optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl; and a heteroaryl optionally substituted with one to three substituents independently selected from the group consisting of $C_{1-6}$alkanyl and halogen wherein said heteroaryl is pyridyl, pyrimidyl, furyl, thienyl or imidazolyl.

17. The compound of claim 15 wherein L is a direct bond or $C_{1-8}$alkandiyl.

18. The compound of claim 15 wherein $R_3$ is selected from the group consisting of naphthyl substituted with hydroxyl; quinolinyl optionally substituted with one or more substituents selected from the group consisting of methyl and chloro; quinolinyl-N-oxide; isoquinolinyl optionally substituted with one or more substituents selected from the group consisting of methyl and chloro and isoquinolinyl-N-oxide.

19. A compound of Formula (I):

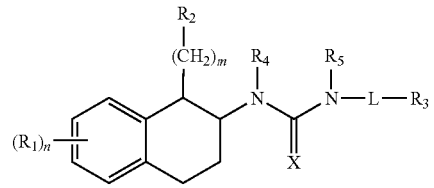

Formula (I)

wherein:

$R_1$ is a substituent independently selected from the group consisting of $C_{1-8}$alkanyl optionally independently substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$ alkanylamino)carbonyl; (arylamino)carbonyl and aryl($C_{1-8}$alkanyl)carbonyl;

n is an integer from 1 to 3;

m is 1;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and an enantiomer, a diastereomer, a tautomer, or a pharmaceutically acceptable salt thereof.

20. The compound of claim 19 wherein $R_2$ is independently selected from the group consisting of hydrogen; $C_{2-8}$alkenyl; $C_{3-8}$cycloalkanyl; phenyl optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl; naphthyl optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl; and a heteroaryl optionally substituted with one to three substituents independently selected from the group consisting of $C_{1-6}$alkanyl and halogen wherein said heteroaryl is pyridyl, pyrimidyl, furyl, thienyl or imidazolyl.

21. The compound of claim 19 wherein L is a direct bond or $C_{1-8}$alkandiyl.

22. The compound of claim 19 wherein $R_3$ is selected from the group consisting of naphthyl substituted with hydroxyl; quinolinyl optionally substituted with one or more substituents selected from the group consisting of methyl and chloro; quinolinyl-N-oxide; isoquinolinyl optionally substituted with one or more substituents selected from the group consisting of methyl and chloro and isoquinolinyl-N-oxide.

23. A compound of Formula (I):

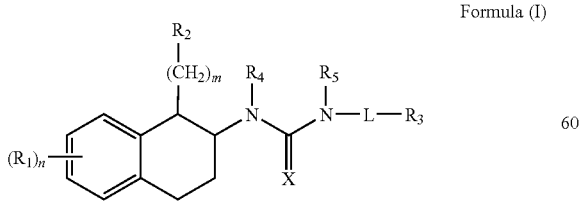

Formula (I)

wherein:

$R_1$ is a substituent independently selected from the group consisting of $C_{1-8}$alkanyl optionally independently substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is an integer from 0 to 3;

$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$) alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond or $C_{1-8}$alkandiyl;

$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;

$R_5$ is selected from the group consisting of hydrogen and $C_{1-8}$alkanyl;

X is selected from the group consisting of O and S; and an enantiomer, a diastereomer, a tautomer, or a pharmaceutically acceptable salt thereof.

24. The compound of claim 23 wherein $R_2$ is independently selected from the group consisting of hydrogen; $C_{2-8}$alkenyl; $C_{1-8}$alkylidenyl; $C_{1-8}$alkylidynyl; $C_{3-8}$cycloalkanyl; phenyl optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl; naphthyl optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl; and a heteroaryl optionally substituted with one to three substituents independently selected from the group consisting of $C_{1-6}$alkanyl and halogen wherein said heteroaryl is pyridyl, pyrimidyl, furyl, thienyl or imidazolyl.

25. The compound of claim 23 wherein $R_3$ is selected from the group consisting of naphthyl substituted with hydroxyl; quinolinyl optionally substituted with one or more substituents selected from the group consisting of methyl and chloro; quinolinyl-N-oxide; isoquinolinyl optionally substituted with one or more substituents selected from the group consisting of methyl and chloro and isoquinolinyl-N-oxide.

26. A compound of Formula (I):

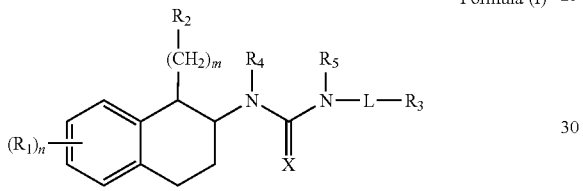

Formula (I)

wherein:
$R_1$ is a substituent independently selected from the group consisting of $C_{1-8}$alkanyl optionally independently substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$ alkanylamino)carbonyl; (arylamino)carbonyl and aryl($C_{1-8}$alkanyl)carbonyl;

n is an integer from 1 to 3;
m is an integer from 0 to 3;
$R_2$ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond;
$R_3$ is selected from the group consisting of phenyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; naphthyl optionally substituted with one to three substituents independently selected from the group consisting of $C_{1-8}$alkanyl, halogen, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, halogen, nitro, amino and cyano wherein said heteroaryl is quinolinyl-N-oxide, isoquinolinyl, isoquinolinyl-N-oxide, pyridyl, pyridyl-N-oxide, pyrimidyl, furyl, thienyl or imidazolyl;

$R_4$ is selected from the group consisting of hydrogen and $C_{1-8}$alkanyl;
$R_5$ is selected from the group consisting of hydrogen and $C_{1-8}$alkanyl;
X is selected from the group consisting of O and S; and
an enantiomer, a diastereomer, a tautomer, or a pharmaceutically acceptable salt thereof.

27. The compound of claim 26 wherein $R_2$ is independently selected from the group consisting of hydrogen; $C_{2-8}$alkenyl; $C_{1-8}$alkylidenyl; $C_{1-8}$alkylidynyl; $C_{3-8}$cycloalkanyl; phenyl optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl; naphthyl optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl; and a heteroaryl optionally substituted with one to three substituents independently selected from the group consisting of $C_{1-6}$alkanyl and halogen wherein said heteroaryl is pyridyl, pyrimidyl, furyl, thienyl or imidazolyl.

28. The compound of claim 26 wherein $R_3$ is selected from the group consisting of naphthyl substituted with hydroxyl; quinolinyl optionally substituted with one or more substituents selected from the group consisting of methyl and chloro; quinolinyl-N-oxide; isoquinolinyl optionally substituted with one or more substituents selected from the group consisting of methyl and chloro and isoquinolinyl-N-oxide.

29. A compound comprising a compound of Formula (I):

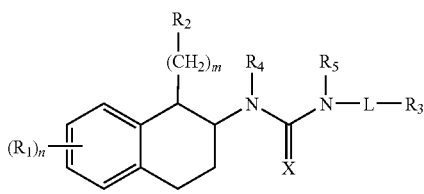

Formula (I)

wherein:
R₁ is a substituent independently selected from the group consisting of $C_{1-8}$alkanyl optionally independently substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$alkanylamino)carbonyl; (arylamino)carbonyl and aryl($C_{1-8}$alkanyl)carbonyl;

n is an integer from 1 to 3;

m is an integer from 0 to 3;

R₂ is independently selected from the group consisting of hydrogen; hydroxy; $C_{1-8}$alkanyl; $C_{2-8}$alkenyl; $C_{1-8}$alkylidenyl; $C_{1-8}$alkylidynyl; fluoro; chloro; $C_{3-8}$cycloalkanyl; phenyl optionally substituted with one to three substituents independently selected from the group consisting of halogen, hydroxy, $C_{1-8}$alkanyl, $C_{1-8}$alkanyloxy, phenyl($C_{1-8}$)alkanyloxy, fluorinated alkanyl, cyano, nitro, amino, $C_{1-8}$alkanylamino, and $C_{1-8}$dialkanylamino; naphthyl optionally substituted with one to three substituents independently selected from the group consisting of halogen, hydroxy, $C_{1-8}$alkanyl, $C_{1-8}$alkanyloxy, phenyl($C_{1-8}$) alkanyloxy, fluorinated alkanyl, cyano, nitro, amino, $C_{1-8}$alkanylamino, and $C_{1-8}$dialkanylamino; phenoxy optionally substituted with one to three substituents independently selected from the group consisting of halogen, hydroxy, $C_{1-8}$alkanyl, $C_{1-8}$alkanyloxy, fluorinated alkanyl, cyano and nitro; and heteroaryl optionally substituted with one to three substituents independently selected from the group consisting of $C_{1-6}$alkanyl and halogen wherein said heteroaryl is pyridyl, pyrimidyl, furyl, thienyl or imidazolyl; pyrrolidino; and piperidino;

L is a direct bond, $C_{1-8}$alkandiyl, $C_{2-8}$alkendiyl, $C_{2-8}$alkyndiyl, or $C_{3-8}$cycloalkandiyl;

R₃ is selected from the group consisting of phenyl substituted with one to three substituents independently selected from the group consisting of $C_{1-8}$alkanyl, fluoro, chloro, bromo, $C_{1-8}$alkanyloxy, hydroxy, fluorinated alkanyl, nitro, amino, di($C_{1-8}$)alkanylamino, $C_{1-8}$alkanylamino and cyano; naphthyl substituted with one to three substituents independently selected from the group consisting of $C_{1-8}$alkanyl, fluoro, chloro, bromo, $C_{1-8}$alkanyloxy, hydroxy, fluorinated alkanyl, nitro, amino, di($C_{1-8}$)alkanylamino, $C_{1-8}$alkanylamino and cyano; and heteroaryl optionally substituted with one to three substituents independently selected from the group consisting of $C_{1-8}$alkanyl, fluoro and chloro, wherein said heteroaryl is quinolinyl-N-oxide, isoquinolinyl, isoquinolinyl-N-oxide, pyridyl, pyridyl-N-oxide, pyrimidyl, furyl, thienyl or imidazolyl;

R₄ is selected from the group consisting of hydrogen and $C_{1-8}$alkanyl;

R₅ is selected from the group consisting of hydrogen and $C_{1-8}$alkanyl;

X is selected from the group consisting of O and S; and an enantiomer, a diastereomer, a tautomer, or a pharmaceutically acceptable salt thereof.

30. The compound of claim 29 wherein R₂ is independently selected from the group consisting of hydrogen; $C_{2-8}$alkenyl; $C_{1-8}$alkylidenyl; $C_{1-8}$alkylidynyl; $C_{3-8}$cycloalkanyl; phenyl optionally substituted with one to three substituents independently selected from the group consisting of fluoro, chloro, bromo, hydroxy, $C_{1-8}$alkanyl, $C_{1-8}$alkanyloxy, phenyl($C_{1-8}$) alkanyloxy, and fluorinated alkanyl; naphthyl optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl; and a heteroaryl optionally substituted with one to three substituents independently selected from the group consisting of $C_{1-6}$alkanyl and halogen wherein said heteroaryl is pyridyl, pyrimidyl, furyl, thienyl or imidazolyl.

31. The compound of claim 29 wherein L is a direct bond or $C_{1-8}$alkandiyl.

32. A compound of Formula (I):

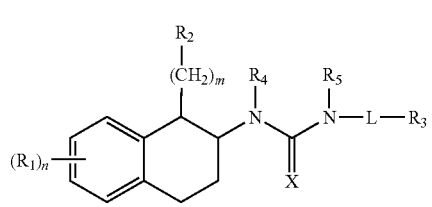

Formula (I)

wherein:
R₁ is a substituent independently selected from the group consisting of $C_{1-8}$alkanyl optionally independently substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; ($C_{1-8}$ alkanylamino)carbonyl; (arylamino)carbonyl and aryl($C_{1-8}$alkanyl)carbonyl;

n is an integer from 1 to 3;

m is an integer from 0 to 3;

R$_2$ is independently selected from the group consisting of hydrogen; hydroxy; C$_{1-8}$alkanyl; C$_{2-8}$alkenyl; C$_{1-8}$alkylidenyl; C$_{1-8}$alkylidynyl; fluoro; chloro; C$_{3-8}$cycloalkanyl; phenyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; naphthyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; phenoxy optionally substituted with one to three substituents independently selected from the group consisting of halogen, hydroxy, C$_{1-8}$alkanyl, C$_{1-8}$alkanyloxy, fluorinated alkanyl, cyano and nitro; and heteroaryl optionally substituted with one to three substituents independently selected from the group consisting of C$_{1-6}$alkanyl and halogen wherein said heteroaryl is pyridyl, pyrimidyl, furyl, thienyl or imidazolyl; pyrrolidino; and piperidino;

L is a direct bond, C$_{1-8}$alkandiyl, C$_{2-8}$alkendiyl, C$_{2-8}$alkyndiyl, or C$_{3-8}$cycloalkandiyl;

R$_3$ is selected from the group consisting of phenyl substituted with one to three substituents independently selected from the group consisting of C$_{1-8}$alkanyloxy and hydroxy; naphthyl substituted with one to three substituents independently selected from the group consisting of C$_{1-8}$alkanyloxy and hydroxy; and heteroaryl optionally substituted with one to three substituents independently selected from the group consisting of C$_{1-8}$alkanyl and chloro wherein said heteroaryl is quinolinyl-N-oxide, isoquinolinyl, isoquinolinyl-N-oxide, pyridyl and pyridyl-N-oxide;

R$_4$ is selected from the group consisting of hydrogen and C$_{1-8}$alkanyl;

R$_5$ is selected from the group consisting of hydrogen and C$_{1-8}$alkanyl;

X is selected from the group consisting of O and S; and an enantiomer, a diastereomer, a tautomer, or a pharmaceutically acceptable salt thereof.

33. The compound of claim 32 wherein R$_2$ is independently selected from the group consisting of hydrogen; C$_{2-8}$alkenyl; C$_{1-8}$alkylidenyl; C$_{1-8}$alkylidynyl C$_{3-8}$cycloalkanyl; phenyl optionally substituted with one to three substituents independently selected from the group consisting of fluoro, chloro, bromo, hydroxy, C$_{1-8}$alkanyl, C$_{1-8}$alkanyloxy, phenyl(C$_{1-8}$)alkanyloxy, and fluorinated alkanyl; naphthyl optionally substituted with one to three substituents independently selected from the group consisting of fluoro, chloro, bromo, hydroxy, C$_{1-8}$alkanyl, C$_{1-8}$alkanyloxy, phenyl(C$_{1-8}$)alkanyloxy, and fluorinated alkanyl; and a heteroaryl optionally substituted with one to three substituents independently selected from the group consisting of C$_{1-6}$alkanyl and halogen wherein said heteroaryl is pyridyl, pyrimidyl, furyl, thienyl or imidazolyl.

34. The compound of claim 32 wherein L is a direct bond or C$_{1-8}$alkandiyl.

35. A compound of Formula (I):

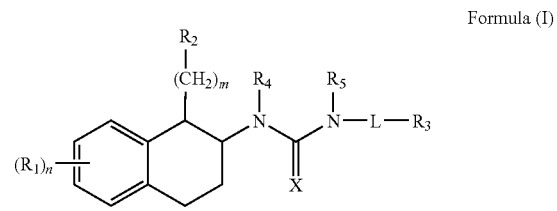

Formula (I)

wherein:

R$_1$ is a substituent independently selected from the group consisting of C$_{1-8}$alkanyl optionally independently substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cycloalkanylamino; cyano; carboxy; C$_{1-7}$alkanyloxycarbonyl; C$_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidinyl; (C$_{1-8}$alkanylamino)carbonyl; (arylamino)carbonyl and aryl(C$_{1-8}$alkanyl)carbonyl;

n is an integer from 1 to 3;

m is an integer from 0 to 3;

R$_2$ is independently selected from the group consisting of hydrogen; hydroxy; C$_{1-8}$alkanyl; C$_{2-8}$alkenyl; C$_{1-8}$alkylidenyl; C$_{1-8}$alkylidynyl; fluoro; chloro; C$_{3-8}$cycloalkanyl; phenyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; naphthyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; phenoxy optionally substituted with one to three substituents independently selected from the group consisting of halogen, hydroxy, C$_{1-8}$alkanyl, C$_{1-8}$alkanyloxy, fluorinated alkanyl, cyano and nitro; and heteroaryl optionally substituted with one to three substituents independently selected from the group consisting of C$_{1-6}$alkanyl and halogen wherein said heteroaryl is pyridyl, pyrimidyl, furyl, thienyl or imidazolyl; pyrrolidino; and piperidino;

L is a direct bond, C$_{1-8}$alkandiyl, C$_{2-8}$alkendiyl, C$_{2-8}$alkyndiyl, or C$_{3-8}$cycloalkandiyl;

R$_3$ is selected from the group consisting of naphthyl substituted with hydroxyl; quinolinyl optionally substituted with one or more substituents selected from the group consisting of methyl and chloro, quinolinyl-N-oxide, isoquinolinyl optionally substituted with one or more substituents selected from the group consisting of methyl and chloro and isoquinolinyl-N-oxide;

R$_4$ is selected from the group consisting of hydrogen and C$_{1-8}$alkanyl;

R$_5$ is selected from the group consisting of hydrogen and C$_{1-8}$alkanyl;

X is selected from the group consisting of O and S; and an enantiomer, a diastereomer, a tautomer, or a pharmaceutically acceptable salt thereof.

36. The compound of claim 35 wherein R$_2$ is independently selected from the group consisting of hydrogen; C$_{2-8}$alkenyl; C$_{1-8}$alkylidenyl; C$_{1-8}$alkylidynyl; C$_{3-8}$cycloalkanyl; phenyl optionally substituted with one to three substituents independently selected from the group consisting of fluoro, chloro, bromo, hydroxy, C$_{1-8}$alkanyl, C$_{1-8}$alkanyloxy, phenyl(C$_{1-8}$)alkanyloxy, and fluorinated alkanyl; naphthyl optionally substituted with one to three substituents independently selected from the group consisting of fluoro, chloro, bromo, hydroxy, C$_{1-8}$alkanyl, C$_{1-8}$alkanyloxy, phenyl(C$_{1-8}$)alkanyloxy, and fluorinated alkanyl; and a heteroaryl optionally substituted with one to three substituents independently selected from the group consisting of C$_{1-6}$alkanyl and halogen wherein said heteroaryl is pyridyl, pyrimidyl, furyl, thienyl or imidazolyl.

37. The compound of claim 35 wherein L is a direct bond or C$_{1-8}$alkandiyl.

38. A compound of Formula (I):

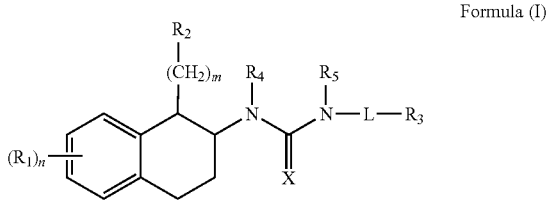

Formula (I)

wherein:

R$_1$ is a substituent independently selected from the group consisting of C$_{1-8}$alkanyl optionally independently substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cycloalkanylamino; cyano; carboxy; C$_{1-7}$alkanyloxycarbonyl; C$_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; (C$_{1-8}$alkanylamino)carbonyl; (arylamino)carbonyl and aryl(C$_{1-8}$alkanyl)carbonyl;

n is an integer from 1 to 3;

m is an integer from 0 to 3;

R$_2$ is independently selected from the group consisting of hydrogen; hydroxy; C$_{1-8}$alkanyl; C$_{2-8}$alkenyl; C$_{1-8}$alkylidenyl; C$_{1-8}$alkylidynyl; fluoro; chloro; C$_{3-8}$cycloalkanyl; phenyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; naphthyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; phenoxy optionally substituted with one to three substituents independently selected from the group consisting of halogen, hydroxy, C$_{1-8}$alkanyl, C$_{1-8}$alkanyloxy, fluorinated alkanyl, cyano and nitro; and heteroaryl optionally substituted with one to three substituents independently selected from the group consisting of C$_{1-6}$alkanyl and halogen wherein said heteroaryl is pyridyl, pyrimidyl, furyl, thienyl or imidazolyl; pyrrolidino; and piperidino;

L is a direct bond, C$_{1-8}$alkandiyl, C$_{2-8}$alkendiyl, C$_{2-8}$alkyndiyl, or C$_{3-8}$cycloalkandiyl;

R$_3$ is 2-hydroxynaphth-8-yl, isoquinolin-5-yl and isoquinolinyl-5-yl-N-oxide;

R$_4$ is selected from the group consisting of hydrogen and C$_{1-8}$alkanyl;

R$_5$ is selected from the group consisting of hydrogen and C$_{1-8}$alkanyl;

X is selected from the group consisting of O and S; and an enantiomer, a diastereomer, a tautomer, or a pharmaceutically acceptable salt thereof.

39. The compound of claim 38 wherein R$_2$ is independently selected from the group consisting of hydrogen; C$_{2-8}$alkenyl; C$_{1-8}$alkylidenyl; C$_{1-8}$alkylidynyl; C$_{3-8}$cycloalkanyl; phenyl optionally substituted with one to three substituents independently selected from the group consisting of fluoro, chloro, bromo, hydroxy, C$_{1-8}$alkanyl, C$_{1-8}$alkanyloxy, phenyl(C$_{1-8}$)alkanyloxy, and fluorinated alkanyl; naphthyl optionally substituted with one to three substituents independently selected from the group consisting of fluoro, chloro, bromo, hydroxy, C$_{1-8}$alkanyl, C$_{1-8}$alkanyloxy, phenyl(C$_{1-8}$)alkanyloxy, and fluorinated alkanyl; and a heteroaryl optionally substituted with one to three substituents independently selected from the group consisting of C$_{1-6}$alkanyl and halogen wherein said heteroaryl is pyridyl, pyrimidyl, furyl, thienyl or imidazolyl.

40. The compound of claim 38 wherein L is a direct bond or C$_{1-8}$alkandiyl.

41. A compound of Formula (I):

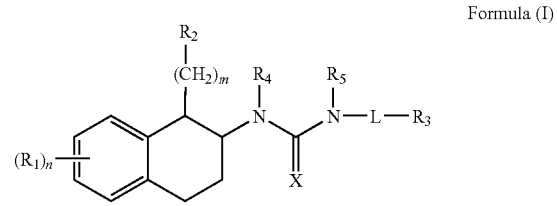

Formula (I)

wherein:

R$_1$ is a substituent independently selected from the group consisting of C$_{1-8}$alkanyl optionally independently substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cycloalkanylamino; cyano; carboxy; C$_{1-7}$alkanyloxycarbonyl; C$_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; (C$_{1-8}$alkanylamino)carbonyl; (arylamino)carbonyl and aryl(C$_{1-8}$alkanyl)carbonyl;

n is an integer from 1 to 3;

m is an integer from 0 to 3;

R$_2$ is independently selected from the group consisting of hydrogen; hydroxy; C$_{1-8}$alkanyl; C$_{2-8}$alkenyl; C$_{1-8}$alkylidenyl; C$_{1-8}$alkylidynyl; fluoro; chloro; C$_{3-8}$cycloalkanyl; phenyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; naphthyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; phenoxy optionally substituted with one to three substituents independently selected from the group consisting of halogen, hydroxy, C$_{1-8}$alkanyl, C$_{1-8}$alkanyloxy, fluorinated alkanyl, cyano and nitro; and heteroaryl optionally substituted with one to three substituents independently selected from the group consisting of C$_{1-6}$alkanyl and halogen wherein said heteroaryl is pyridyl, pyrimidyl, furyl, thienyl or imidazolyl; pyrrolidino; and piperidino;

L is a direct bond, C$_{1-8}$alkandiyl, C$_{2-8}$alkendiyl, C$_{2-8}$alkyndiyl, or C$_{3-8}$cycloalkandiyl;

R$_3$ is selected from the group consisting of phenyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; naphthyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; and heteroaryl optionally substituted with one to three substituents independently selected from the group consisting of C$_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

R$_4$ is hydrogen;

R$_5$ is selected from the group consisting of hydrogen and C$_{1-8}$alkanyl;

X is selected from the group consisting of O and S; and an enantiomer, a diastereomer, a tautomer, or a pharmaceutically acceptable salt thereof.

42. The compound of claim 41 wherein R$_2$ is independently selected from the group consisting of hydrogen; C$_{2-8}$alkenyl; C$_{1-8}$alkylidenyl; C$_{1-8}$alkylidynyl; C$_{3-8}$cycloalkanyl; phenyl optionally substituted with one to three substituents independently selected from the group consisting of fluoro, chloro, bromo, hydroxy, C$_{1-8}$alkanyl, C$_{1-8}$alkanyloxy, phenyl(C$_{1-8}$)alkanyloxy, and fluorinated alkanyl; naphthyl optionally substituted with one to three substituents independently selected from the group consisting of fluoro, chloro, bromo, hydroxy, C$_{1-8}$alkanyl, C$_{1-8}$alkanyloxy, phenyl(C$_{1-8}$)alkanyloxy, and fluorinated alkanyl; and a heteroaryl optionally substituted with one to three substituents independently selected from the group consisting of C$_{1-6}$alkanyl and halogen wherein said heteroaryl is pyridyl, pyrimidyl, furyl, thienyl or imidazolyl.

43. The compound of claim 41 wherein L is a direct bond or C$_{1-8}$alkandiyl.

44. The compound of claim 41 wherein R$_3$ is selected from the group consisting of naphthyl substituted with hydroxyl; quinolinyl optionally substituted with one or more substituents selected from the group consisting of methyl and chloro; quinolinyl-N-oxide; isoquinolinyl optionally substituted with one or more substituents selected from the group consisting of methyl and chloro and isoquinolinyl-N-oxide.

45. A compound of Formula (I):

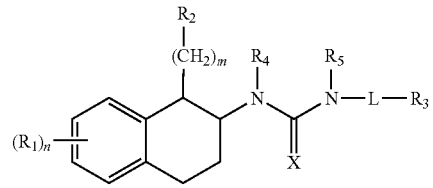

Formula (I)

wherein:

R$_1$ is a substituent independently selected from the group consisting of C$_{1-8}$alkanyl optionally independently substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cycloalkanylamino; cyano; carboxy; C$_{1-7}$alkanyloxycarbonyl; C$_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; (C$_{1-8}$alkanylamino)carbonyl; (arylamino)carbonyl and aryl(C$_{1-8}$alkanyl)carbonyl;

n is an integer from 1 to 3;

m is an integer from 0 to 3;

R$_2$ is independently selected from the group consisting of hydrogen; hydroxy; C$_{1-8}$alkanyl; C$_{2-8}$alkenyl; C$_{1-8}$alkylidenyl; C$_{1-8}$alkylidynyl; fluoro; chloro; C$_{3-8}$cycloalkanyl; phenyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; naphthyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; phenoxy optionally substituted with one to three substituents independently selected from the group consisting of halogen, hydroxy, C$_{1-8}$alkanyl, C$_{1-8}$alkanyloxy, fluorinated alkanyl, cyano and nitro; and heteroaryl optionally substituted with one to three substituents independently selected from the group consisting of C$_{1-6}$alkanyl and halogen wherein said heteroaryl is pyridyl, pyrimidyl, furyl, thienyl or imidazolyl; pyrrolidino; and piperidino;

L is a direct bond, C$_{1-8}$alkandiyl, C$_{2-8}$alkendiyl, C$_{2-8}$alkyndiyl, or C$_{3-8}$cycloalkandiyl;

R$_3$ is selected from the group consisting of phenyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; naphthyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; and heteroaryl optionally substituted with one to three substituents independently selected from the group consisting of C$_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

R$_4$ is selected from the group consisting of hydrogen and C$_{1-8}$alkanyl;

R$_5$ is hydrogen;

X is selected from the group consisting of O and S; and an enantiomer, a diastereomer, a tautomer, or a pharmaceutically acceptable salt thereof.

46. The compound of claim 45 wherein R$_2$ is independently selected from the group consisting of hydrogen; C$_{2-8}$alkenyl; C$_{1-8}$alkylidenyl; C$_{1-8}$alkylidynyl; C$_{3-8}$cycloalkanyl; phenyl optionally substituted with one to three substituents independently selected from the group consisting of fluoro, chloro, bromo, hydroxy, C$_{1-8}$alkanyl, C$_{1-8}$alkanyloxy, phenyl(C$_{1-8}$)alkanyloxy, and fluorinated alkanyl; naphthyl optionally substituted with one to three substituents independently selected from the group consisting of fluoro, chloro, bromo, hydroxy, C$_{1-8}$alkanyl, C$_{1-8}$alkanyloxy, phenyl(C$_{1-8}$)alkanyloxy, and fluorinated alkanyl; and a heteroaryl optionally substituted with one to three substituents independently selected from the group consisting of C$_{1-6}$alkanyl and halogen wherein said heteroaryl is pyridyl, pyrimidyl, furyl, thienyl or imidazolyl.

47. The compound of claim 45 wherein L is a direct bond or C$_{1-8}$alkandiyl.

48. The compound of claim 45 wherein R$_3$ is selected from the group consisting of naphthyl substituted with hydroxyl; quinolinyl optionally substituted with one or more substituents selected from the group consisting of methyl and chloro; quinolinyl-N-oxide; isoquinolinyl optionally substituted with one or more substituents selected from the group consisting of methyl and chloro and isoquinolinyl-N-oxide.

49. A compound of Formula (I):

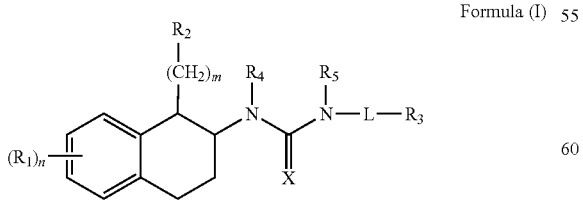

Formula (I)

wherein:

R$_1$ is a substituent independently selected from the group consisting of C$_{1-8}$alkanyl optionally independently substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cycloalkanylamino; cyano; carboxy; C$_{1-7}$alkanyloxycarbonyl; C$_{1-7}$alkanylcarbonyloxy; formyl; carbamoyl; phenyl optionally substituted with one to three substituents independently selected from the group consisting of halogen, hydroxyl, nitro, amino and cyano; aroyl; carbamoyl; amidino; (C$_{1-8}$alkanylamino)carbonyl; (arylamino)carbonyl and aryl(C$_{1-8}$alkanyl)carbonyl;

n is an integer from 1 to 3;

m is an integer from 0 to 3;

R$_2$ is independently selected from the group consisting of hydrogen; hydroxy; C$_{1-8}$alkanyl; C$_{2-8}$alkenyl; C$_{1-8}$alkylidenyl; C$_{1-8}$alkylidynyl; fluoro; chloro; C$_{3-8}$cycloalkanyl; phenyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; naphthyl optionally substituted with one to three substituents independently selected from the group consisting of halogen, hydroxy, C$_{1-8}$alkanyl, C$_{1-8}$alkanyloxy, phenyl(C$_{1-8}$)alkanyloxy, fluorinated alkanyl, cyano, nitro, amino, C$_{1-8}$alkanylamino, and C$_{1-8}$dialkanylamino; phenoxy optionally substituted with one to three substituents independently selected from the group consisting of halogen, hydroxy, C$_{1-8}$alkanyl, C$_{1-8}$alkanyloxy, fluorinated alkanyl, cyano and nitro; and heteroaryl optionally substituted with one to three substituents independently selected from the group consisting of C$_{1-6}$alkanyl and halogen wherein said heteroaryl is pyridyl, pyrimidyl, furyl, thienyl or imidazolyl; pyrrolidino; and piperidino;

L is a direct bond, C$_{1-8}$alkandiyl, C$_{2-8}$alkendiyl, C$_{2-8}$alkyndiyl, or C$_{3-8}$cycloalkandiyl;

R$_3$ is selected from the group consisting of phenyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; naphthyl optionally substituted with one to three substituents independently selected from the group consisting of C$_{1-8}$alkanyl, halogen, C$_{1-8}$alkanyloxy, hydroxy, fluorinated alkanyl, nitro, amino, di(C$_{1-8}$)alkanylamino, C$_{1-8}$alkanylamino and cyano; and heteroaryl optionally substituted with one to three substituents independently selected from the group consisting of C$_{1-8}$alkanyl, halogen, nitro, amino and cyano wherein said heteroaryl is quinolinyl, quinolinyl-N-oxide, isoquinolinyl, isoquinolinyl-N-oxide, pyridyl, pyridyl-N-oxide, pyrimidyl, furyl, thienyl or imidazolyl;

R$_4$ is selected from the group consisting of hydrogen and C$_{1-8}$alkanyl;

R$_5$ is selected from the group consisting of hydrogen and C$_{1-8}$alkanyl;

X is O; and an enantiomer, a diastereomer, a tautomer, or a pharmaceutically acceptable salt thereof.

50. The compound of claim 49 wherein $R_2$ is independently selected from the group consisting of hydrogen; $C_{2-8}$alkenyl; $C_{1-8}$alkylidenyl; $C_{1-8}$alkylidynyl; $C_{3-8}$cycloalkanyl; phenyl optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl; naphthyl optionally substituted with one to three substituents independently selected from the group consisting of fluoro, chloro, bromo, hydroxy, $C_{1-8}$alkanyl, $C_{1-8}$alkanyloxy, phenyl($C_{1-8}$)alkanyloxy, and fluorinated alkanyl; and a heteroaryl optionally substituted with one to three substituents independently selected from the group consisting of $C_{1-6}$alkanyl and halogen wherein said heteroaryl is pyridyl, pyrimidyl, furyl, thienyl or imidazolyl.

51. The compound of claim 49 wherein L is a direct bond or $C_{1-8}$alkandiyl.

52. The compound of claim 49 wherein $R_3$ is selected from the group consisting of naphthyl substituted with hydroxyl; quinolinyl optionally substituted with one or more substituents selected from the group consisting of methyl and chloro; quinolinyl-N-oxide; isoquinolinyl optionally substituted with one or more substituents selected from the group consisting of methyl and chloro and isoquinolinyl-N-oxide.

* * * * *